United States Patent
Nguyen et al.

(10) Patent No.: US 12,428,485 B2
(45) Date of Patent: Sep. 30, 2025

(54) COMPOSITIONS AND METHODS TO BLOCK AND BIND CCR2 TO MODULATE CELLULAR FUNCTION

(71) Applicant: The Research Foundation for The State University of New York, Amherst, NY (US)

(72) Inventors: Juliane Nguyen, Buffalo, NY (US); Michael Deci, Buffalo, NY (US)

(73) Assignee: The Research Foundation for The State University of New York, Amherst, NY (US)

(*) Notice: Subject to any disclaimer, the term of this patent is extended or adjusted under 35 U.S.C. 154(b) by 993 days.

(21) Appl. No.: 17/611,119

(22) PCT Filed: May 13, 2020

(86) PCT No.: PCT/US2020/032683
§ 371 (c)(1),
(2) Date: Nov. 12, 2021

(87) PCT Pub. No.: WO2020/232127
PCT Pub. Date: Nov. 19, 2020

(65) Prior Publication Data
US 2022/0220212 A1 Jul. 14, 2022

Related U.S. Application Data

(60) Provisional application No. 62/846,947, filed on May 13, 2019.

(51) Int. Cl.
*C07K 16/28* (2006.01)
*A61K 39/00* (2006.01)
*A61P 35/00* (2006.01)

(52) U.S. Cl.
CPC ........ *C07K 16/2866* (2013.01); *A61P 35/00* (2018.01); *A61K 39/00* (2013.01); *C07K 2317/56* (2013.01); *C07K 2317/565* (2013.01); *C07K 2317/622* (2013.01)

(58) Field of Classification Search
CPC ............ C07K 16/2866; C07K 2317/56; C07K 2317/565; C07K 2317/622
See application file for complete search history.

(56) References Cited

U.S. PATENT DOCUMENTS

| 8,926,976 B2 * | 1/2015 | Corbin ............... A61P 35/00 424/143.1 |
| 10,703,803 B2 * | 7/2020 | Bujny ............... C07K 16/1018 |
| 2009/0311273 A1 | 12/2009 | Prinz et al. |

FOREIGN PATENT DOCUMENTS

| WO | 2010/021697 A2 | 2/2010 |
| WO | 2018/102795 A2 | 6/2018 |

OTHER PUBLICATIONS

Paul, Fundamental Immunology, 3rd Edition, 1993, pp. 292-295 (Year: 1993).*
Almagro & Fransson, Frontiers in Bioscience 2008; 13:1619-33 (Year: 2008).*
Rudikoff et al(Proc. Natl. Acad. Sci. USA 1982 vol. 79: p. 1979 (Year: 1982).*
Pascalis et al (The Journal of Immunology (2002) 169, 3076-3084) (Year: 2002).*
Casset et al. (2003) BBRC 307, 198-205 (Year: 2003).*
D'Angelo et al, Frontiers in Immunology vol. 9 p. 1 (2018) (Year: 2018).*
Deci, M., et al., Modulating Macrophage Polarization through CCR2 Inhibition and Multivalent Engagement, Molecular Pharmaceutics, May 2018, vol. 15, No. 7, pp. 2721-2731.

* cited by examiner

*Primary Examiner* — Sheela J. Huff
(74) *Attorney, Agent, or Firm* — Hodgson Russ LLP

(57) ABSTRACT

Provided herein are single chain variable fragment antibodies that are directed against N-terminal or extracellular loop regions of CCR2. The scFvs can be used alone or in combination to modify macrophage number and migration and to reduce the growth of tumors.

8 Claims, 39 Drawing Sheets
Specification includes a Sequence Listing.

B

N-terminal domain scFvs

|  | CDRL1 |
| --- | --- |
| 13F | LQAVLTQP-SSLSASPGASASLTCILRSDFSVYTQRVYWYQQKPGS |
| 25B | LQSVLTQP-PSVSGAPGQKVTISCSG-SSSNIGNNYVSWYQQLPGT |
| 26B | LQSVLTQP-PSASGTPGQRVTISCSG-SSNIGSNYVYWYQQLPGT |
| 37B | LEVQLVES-GAEVKKPGASVKVSCKA-SGYTTSYMHWVRQAPGQ |
| 58C | LEIVLTQSPGTLSLSPGERATLSCRA---SQSVSSSYLAWYQQKPGQ |

|  | CDRL2 | CDRL3 |
| --- | --- | --- |
| 13F | PPRYLLRYINSDKELGSGVPS----RFSGSKDVSANAASLLISGLQSDDEADYYCVIWHHS---AVVFGGGTKLT |
| 25B | APKL-LIYGWN---KR-PSGIPD----RFSGSK---SGTSATIGITGLQTGDEADYYCATWDDSLSAVVFGGGTKLT |
| 26B | APKL-LIYRMN---QR-PSGVPD----RFSGSK---SGTSASLAISGLQSEDEADYYCAAWDDSLMGVYFGGGTELT |
| 37B | GLEWMGIIMPS---GG-STYAQKFQGRVTMTRDTSTSTVYMELSSLRSEDTAVYYCARDGM---WFDPWGQGTLVT |
| 58C | APRL-LIYGAS---SR-ATGIPD----RFSGSG---SGTDFTLTISRLEPEDFAVYYCQQYGS----SLTFGGGTKVE |

|  | CDRH1 | CDRH2 |
| --- | --- | --- |
| 13F | VL-GEGKSSSGSESKASEVQLLES-GAEVKKPGESLKISCKGSGYSETSYWIGWVEQMPGKGLEWMGIIYPGDS |
| 25B | VL-GEGKSSSGSESKASEVQLLES-GAEVKKPGASVKVSCKASGYTFTNFYIHWVRRAPGQGLEWMGIINPSDG |
| 26B | VL-GEGKSSSGSESKASQVTLKES-GAEVKKPGASVKVSCKASGYTFTNFYIHWVRRAPGQGLEWMGIINPSDG |
| 37B | VSSGEKSSSGSESKASEIVMTQSPGTLSLSPGERATLSCRASQ-SVSSSYLAWYQQKPGQAPRLL-IYGASSR |
| 58C | IK--EGKSSSGSESKASEVQLLES-GAEVKKPGASVKVSCKVSCKTSGYTFTTYDIYWMFLATGQELEWMGWVMPDNG |

|  | CDRH2 contd | CDRH3 |
| --- | --- | --- |
| 13F | DTRYSPSFQG-QVTTISADKSISTAVLQWSSIKASDTAMYYCARRPQYYDILTGWHAGWFDPWGQGTLVTVSS |
| 25B | RTTYAQKFQG-RVTMTRDTSTSTVYMELTSLRSEDTAVYYCGRGGHYSNYF-----GQPSTWGQGTLVTVSS |
| 26B | RTTYAQKFQG-RVTMTRDTSTSTLLYMELTSLRSEDTAVYYCGEGGHYSNYF-----GQPSTWGQGTLVTVSS |
| 37B | ATGIPDRFSG---SGSGTDFTLTISRLEPEDFAVYYCQ------QYG-S-------SPPLTFGGGTKLDI-K |
| 58C | KTDYAQKFQG-RVTISRDSSINTVFMELSNLRLEDTAIYFCARALTRWQ-Q------SPLGYWGQGTLVTVSS |

Extracellular loop 2 scFvs

```
                                                                                    CDRL1
4h   MKKTAIAIAVALAIAVALAGFATVAQADIKDDDDKLQSVLTQPPSASGTPGQRVTISCSGSSSNIG
11D  MKKTAIAIAVALAIAVALAGFATVAQADIKDDDDKLQPVLTQPPSASGTPGQRVTISCSGSSSNIG

CDRL1 contd                                          CDRL2
4h   SNTVNWYQQLPGTAPKLLIYRNNQRPSGVPDRFSGSKSGTSASLAISGLRSEDEADYYCA
11D  SNTVYWYQQLPGTAPKLLIYRNNQRPSGVPDRFSGSKSGTSASLAISGLQSEDEADYYCA CDRL3 contd                                                            CDRL3
4h   AWDDSLSGVVFGGGTKLTVLGEGKSSGSGSESGSESGSESKASQVTLKESGAEVKKPGASVKVSCKAS
11D  AWDDTLIGEVFGGGTKLTVLGEGKSSGSGSESGSESGSESKASEVQLVESGGGLVKPGGSLTLSCAVS CDRH3
4h   GYTFTNFYIHWVRRAPGQGLEWMGII--NPSDGRTIYAQKFQGRVTMTRDTSISTLVMEL
11D  GFPESDAWMWVRQAPGKGLEWVGRIRSKAGGTTDSAAPVKDRFTFSGDDSKNTVYVEM CDRH3
4h   TSLRSEDTAVYYCGRGGHYSNYFGQPSTWGQGTLVTVSSVEAS
11D  NSLKIEDTAVYYCTGEGY--------------WGQGTLVTVSSVEAS
```

Combination Indices

| Ratio | $ED_{50}$ | $ED_{75}$ | $ED_{90}$ | $ED_{95}$ |
|---|---|---|---|---|
| iNos/Arg1 | 0.0430 | 0.0137 | 0.0045 | 0.0021 |
| iNos/Mgl2 | 0.1481 | 0.0813 | 0.0455 | 0.0309 |
| IL-6/Arg1 | 0.1122 | 0.0595 | 0.0317 | 0.0207 |
| IL-6/Mgl2 | 0.1841 | 0.1148 | 0.0716 | 0.0519 |

Combination Index (CI)
Synergistic Effects: CI < 1
Additive Effects: CI = 1
Antagonistic Effects: CI > 1

```
                            SEQUENCE LISTING

<160> NUMBER OF SEQ ID NOS: 61

<210> SEQ ID NO 1
<211> LENGTH: 311
<212> TYPE: PRT
<213> ORGANISM: Homo sapiens

<400> SEQUENCE: 1

Met Lys Lys Thr Ala Ile Ala Ile Ala Val Ala Leu Ala Gly Phe Ala
1               5                   10                  15

Thr Val Ala Gln Ala Asp Tyr Lys Asp Asp Asp Lys Leu Gln Ala
            20                  25                  30

Val Leu Thr Gln Pro Ser Ser Leu Ser Ala Ser Pro Gly Ala Ser Ala
        35                  40                  45

Ser Leu Thr Cys Ile Leu Arg Ser Asp Phe Ser Val Val Thr Gln Arg
    50                  55                  60

Val Tyr Trp Tyr Gln Gln Lys Pro Gly Ser Pro Pro Arg Tyr Leu Leu
65                  70                  75                  80

Arg Tyr Asn Ser Asp Ser Asp Lys Arg Leu Gly Ser Gly Val Pro Ser
                85                  90                  95

Arg Phe Ser Gly Ser Lys Asp Val Ser Ala Asn Ala Ala Ser Leu Leu
            100                 105                 110

Ile Ser Gly Leu Gln Ser Asp Asp Glu Ala Asp Tyr Tyr Cys Val Ile
        115                 120                 125

Trp His Asn Ser Ala Val Val Phe Gly Gly Thr Lys Leu Thr Val
    130                 135                 140

Leu Gly Glu Gly Lys Ser Ser Gly Ser Gly Ser Glu Ser Lys Ala Ser
145                 150                 155                 160

Glu Val Gln Leu Leu Glu Ser Gly Ala Glu Val Lys Lys Pro Gly Glu
                165                 170                 175

Ser Leu Lys Ile Ser Cys Lys Gly Ser Gly Tyr Ser Phe Thr Ser Tyr
            180                 185                 190

Trp Ile Gly Trp Val Arg Gln Met Pro Gly Lys Gly Leu Glu Trp Met
        195                 200                 205

Gly Ile Ile Tyr Pro Gly Asp Ser Asp Thr Arg Tyr Ser Pro Ser Phe
    210                 215                 220

Gln Gly Gln Val Thr Ile Ser Ala Asp Lys Ser Ile Ser Thr Ala Tyr
225                 230                 235                 240
```

```
Leu Gln Trp Ser Ser Leu Lys Ala Ser Asp Thr Ala Met Tyr Tyr Cys
                245                 250                 255

Ala Arg Arg Pro Gln Tyr Tyr Asp Ile Leu Thr Gly Trp His Ala Gly
            260                 265                 270

Trp Phe Asp Pro Trp Gly Gln Gly Thr Leu Val Thr Val Ser Ser Val
        275                 280                 285

Glu Ala Ser Ala Ala Ala Leu Asp Tyr Lys Asp Asp Asp Asp Lys Leu
    290                 295                 300

Asp His His His His His His
305                 310

<210> SEQ ID NO 2
<211> LENGTH: 301
<212> TYPE: PRT
<213> ORGANISM: Homo sapiens

<400> SEQUENCE: 2

Met Lys Lys Thr Ala Ile Ala Ile Ala Val Ala Leu Ala Gly Phe Ala
1               5                   10                  15

Thr Val Ala Gln Ala Asp Tyr Lys Asp Asp Asp Asp Lys Leu Gln Ser
            20                  25                  30

Val Leu Thr Gln Pro Pro Ser Val Ser Gly Ala Pro Gly Gln Lys Val
        35                  40                  45

Thr Ile Ser Cys Ser Gly Ser Ser Ser Asn Ile Gly Asn Asn Tyr Val
    50                  55                  60

Ser Trp Tyr Gln Gln Leu Pro Gly Thr Ala Pro Lys Leu Leu Ile Tyr
65                  70                  75                  80

Gly Asn Asn Lys Arg Pro Ser Gly Ile Pro Asp Arg Phe Ser Gly Ser
                85                  90                  95

Lys Ser Gly Thr Ser Ala Thr Leu Gly Ile Thr Gly Leu Gln Thr Gly
            100                 105                 110

Asp Glu Ala Asp Tyr Tyr Cys Ala Thr Trp Asp Ser Leu Ser Ala
        115                 120                 125

Val Val Phe Gly Gly Gly Thr Lys Leu Thr Val Leu Gly Glu Gly Lys
    130                 135                 140

Ser Ser Gly Ser Gly Ser Glu Ser Lys Ala Ser Gln Val Thr Leu Lys
145                 150                 155                 160

Glu Ser Gly Ala Glu Val Lys Lys Pro Gly Ala Ser Val Lys Val Ser
                165                 170                 175

Cys Lys Ala Ser Gly Tyr Thr Phe Thr Asn Phe Tyr Ile His Trp Val
            180                 185                 190

Arg Arg Ala Pro Gly Gln Gly Leu Glu Trp Met Gly Ile Ile Asn Pro
        195                 200                 205

Ser Asp Gly Arg Thr Thr Tyr Ala Gln Lys Phe Gln Gly Arg Val Thr
    210                 215                 220

Met Thr Arg Asp Thr Ser Thr Ser Thr Leu Tyr Met Glu Leu Thr Ser
225                 230                 235                 240

Leu Arg Ser Glu Asp Thr Ala Val Tyr Tyr Cys Gly Arg Gly Gly His
                245                 250                 255

Tyr Ser Asn Tyr Phe Gly Gln Pro Ser Thr Trp Gly Gln Gly Thr Leu
            260                 265                 270

Val Thr Val Ser Ser Val Glu Ala Ser Ala Ala Ala Leu Asp Tyr Lys
        275                 280                 285

Asp Asp Asp Asp Lys Leu Asp His His His His His
    290                 295                 300
```

<210> SEQ ID NO 3
<211> LENGTH: 301
<212> TYPE: PRT
<213> ORGANISM: Homo sapiens

<400> SEQUENCE: 3

Met Lys Lys Thr Ala Ile Ala Ile Ala Val Ala Leu Ala Gly Phe Ala
1               5                   10                  15

Thr Val Ala Gln Ala Asp Tyr Lys Asp Asp Asp Lys Leu Gln Ser
            20                  25                  30

Val Leu Thr Gln Pro Pro Ser Ala Ser Gly Thr Pro Gly Gln Arg Val
        35                  40                  45

Thr Ile Ser Cys Ser Gly Ser Ser Asn Ile Gly Ser Asn Tyr Val
    50                  55                  60

Tyr Trp Tyr Gln Gln Leu Pro Gly Thr Ala Pro Lys Leu Leu Ile Tyr
65                  70                  75                  80

Arg Asn Asn Gln Arg Pro Ser Gly Val Pro Asp Arg Phe Ser Gly Ser
                85                  90                  95

Lys Ser Gly Thr Ser Ala Ser Leu Ala Ile Ser Gly Leu Gln Ser Glu
            100                 105                 110

Asp Glu Ala Asp Tyr Tyr Cys Ala Ala Trp Asp Ser Leu Asn Gly
        115                 120                 125

Val Val Phe Gly Gly Gly Thr Glu Leu Thr Val Leu Gly Glu Gly Lys
    130                 135                 140

Ser Ser Gly Ser Gly Ser Glu Ser Lys Ala Ser Gln Val Thr Leu Lys
145                 150                 155                 160

Glu Ser Gly Ala Glu Val Lys Lys Pro Gly Ala Ser Val Lys Val Ser
                165                 170                 175

Cys Lys Ala Ser Gly Tyr Thr Phe Thr Asn Phe Tyr Ile His Trp Val
            180                 185                 190

Arg Arg Ala Pro Gly Gln Gly Leu Glu Trp Met Gly Ile Ile Asn Pro
        195                 200                 205

Ser Asp Gly Arg Thr Thr Tyr Ala Gln Lys Phe Gln Gly Arg Val Thr
    210                 215                 220

Met Thr Arg Asp Thr Ser Thr Ser Thr Leu Tyr Met Glu Leu Thr Ser
225                 230                 235                 240

Leu Arg Ser Glu Asp Thr Ala Val Tyr Tyr Cys Gly Arg Gly Gly His
                245                 250                 255

Tyr Ser Asn Tyr Phe Gly Gln Pro Ser Thr Trp Gly Gln Gly Thr Leu
            260                 265                 270

Val Thr Val Ser Ser Val Glu Ala Ser Ala Ala Leu Asp Tyr Lys
        275                 280                 285

Asp Asp Asp Asp Lys Leu Asp His His His His His
    290                 295                 300

<210> SEQ ID NO 4
<211> LENGTH: 294
<212> TYPE: PRT
<213> ORGANISM: Homo sapiens

<400> SEQUENCE: 4

Met Lys Lys Thr Ala Ile Ala Ile Ala Val Ala Leu Ala Gly Phe Ala
1               5                   10                  15

Thr Val Ala Gln Ala Asp Tyr Lys Asp Asp Asp Asp Lys Leu Glu Val
            20                  25                  30

```
Gln Leu Val Glu Ser Gly Ala Glu Val Lys Lys Pro Gly Ala Ser Val
            35                  40                  45

Lys Val Ser Cys Lys Ala Ser Gly Tyr Thr Phe Thr Ser Tyr Tyr Met
 50                  55                  60

His Trp Val Arg Gln Ala Pro Gly Gln Gly Leu Glu Trp Met Gly Ile
 65                  70                  75                  80

Ile Asn Pro Ser Gly Gly Ser Thr Ser Tyr Ala Gln Lys Phe Gln Gly
                85                  90                  95

Arg Val Thr Met Thr Arg Asp Thr Ser Thr Ser Thr Val Tyr Met Glu
            100                 105                 110

Leu Ser Ser Leu Arg Ser Glu Asp Thr Ala Val Tyr Tyr Cys Ala Arg
            115                 120                 125

Asp Gly Asn Trp Phe Asp Pro Trp Gly Gln Gly Thr Leu Val Thr Val
            130                 135                 140

Ser Ser Gly Glu Gly Lys Ser Ser Gly Ser Gly Ser Glu Ser Lys Ala
145                 150                 155                 160

Ser Glu Ile Val Met Thr Gln Ser Pro Gly Thr Leu Ser Leu Ser Pro
                165                 170                 175

Gly Glu Arg Ala Thr Leu Ser Cys Arg Ala Ser Gln Ser Val Ser Ser
            180                 185                 190

Ser Tyr Leu Ala Trp Tyr Gln Gln Lys Pro Gly Gln Ala Pro Arg Leu
            195                 200                 205

Leu Ile Tyr Gly Ala Ser Ser Arg Ala Thr Gly Ile Pro Asp Arg Phe
            210                 215                 220

Ser Gly Ser Gly Ser Gly Thr Asp Phe Thr Leu Thr Ile Ser Arg Leu
225                 230                 235                 240

Glu Pro Glu Asp Phe Ala Val Tyr Tyr Cys Gln Gln Tyr Gly Ser Ser
                245                 250                 255

Pro Pro Leu Thr Phe Gly Gly Gly Thr Lys Leu Asp Ile Lys Val Glu
            260                 265                 270

Ala Ser Ala Ala Ala Leu Asp Tyr Lys Asp Asp Asp Lys Leu Asp
            275                 280                 285

His His His His His His
    290

<210> SEQ ID NO 5
<211> LENGTH: 296
<212> TYPE: PRT
<213> ORGANISM: Homo sapiens

<400> SEQUENCE: 5

Met Lys Lys Thr Ala Ile Ala Ile Ala Val Ala Leu Ala Gly Phe Ala
 1                  5                  10                  15

Thr Val Ala Gln Ala Asp Tyr Lys Asp Asp Asp Lys Leu Glu Ile
            20                  25                  30

Val Leu Thr Gln Ser Pro Gly Thr Leu Ser Leu Ser Pro Gly Glu Arg
            35                  40                  45

Ala Thr Leu Ser Cys Arg Ala Ser Gln Ser Val Ser Ser Ser Tyr Leu
 50                  55                  60

Ala Trp Tyr Gln Gln Lys Pro Gly Gln Ala Pro Arg Leu Leu Ile Tyr
 65                  70                  75                  80

Gly Ala Ser Ser Arg Ala Thr Gly Ile Pro Asp Arg Phe Ser Gly Ser
                85                  90                  95

Gly Ser Gly Thr Asp Phe Thr Leu Thr Ile Ser Arg Leu Glu Pro Glu
```

```
            100                 105                 110
Asp Phe Ala Val Tyr Tyr Cys Gln Gln Tyr Gly Ser Ser Leu Thr Phe
            115                 120                 125

Gly Gly Gly Thr Lys Val Glu Ile Lys Glu Gly Lys Ser Ser Gly Ser
        130                 135                 140

Gly Ser Glu Ser Lys Ala Ser Glu Val Gln Leu Leu Glu Ser Gly Ala
145                 150                 155                 160

Glu Val Lys Lys Pro Gly Ala Ser Val Lys Val Ser Cys Lys Thr Ser
                165                 170                 175

Gly Tyr Thr Phe Thr Thr Tyr Asp Ile Tyr Trp Met Arg Leu Ala Thr
            180                 185                 190

Gly Gln Arg Leu Glu Trp Met Gly Trp Val Asn Pro Asp Asn Gly Lys
        195                 200                 205

Thr Asp Tyr Ala Gln Lys Phe Gln Gly Arg Val Thr Ile Ser Arg Asp
    210                 215                 220

Ser Ser Ile Asn Thr Val Phe Met Glu Leu Ser Asn Leu Arg Leu Glu
225                 230                 235                 240

Asp Thr Ala Ile Tyr Phe Cys Ala Arg Ala Leu Thr Arg Trp Gln Gln
                245                 250                 255

Ser Pro Leu Gly Tyr Trp Gly Gln Gly Thr Leu Val Thr Val Ser Ser
            260                 265                 270

Val Glu Ala Ser Ala Ala Leu Asp Tyr Lys Asp Asp Asp Lys
        275                 280                 285

Leu Asp His His His His His His
    290                 295

<210> SEQ ID NO 6
<211> LENGTH: 281
<212> TYPE: PRT
<213> ORGANISM: Homo sapiens

<400> SEQUENCE: 6

Met Lys Lys Thr Ala Ile Ala Ile Ala Val Ala Leu Ala Gly Phe Ala
1               5                   10                  15

Thr Val Ala Gln Ala Asp Tyr Lys Asp Asp Asp Lys Leu Gln Ser
            20                  25                  30

Val Leu Thr Gln Pro Pro Ser Ala Ser Gly Thr Pro Gly Gln Arg Val
        35                  40                  45

Thr Ile Ser Cys Ser Gly Ser Ser Asn Ile Gly Ser His Thr Val
    50                  55                  60

Asn Trp Tyr Gln Gln Leu Pro Gly Thr Ala Pro Lys Leu Leu Ile Tyr
65                  70                  75                  80

Arg Asn Asn Gln Arg Pro Ser Gly Val Pro Asp Arg Phe Ser Gly Ser
                85                  90                  95

Lys Ser Gly Thr Ser Ala Ser Leu Ala Ile Ser Gly Leu Arg Ser Glu
            100                 105                 110

Asp Glu Ala Asp Tyr Tyr Cys Ala Ala Trp Asp Asp Ser Leu Ser Gly
        115                 120                 125

Val Val Phe Gly Gly Gly Thr Lys Leu Thr Val Leu Gly Glu Gly Lys
    130                 135                 140

Ser Ser Gly Ser Gly Ser Glu Ser Lys Ala Ser Gln Val Thr Leu Lys
145                 150                 155                 160

Glu Ser Gly Ala Glu Val Lys Lys Pro Gly Ala Ser Val Lys Val Ser
                165                 170                 175
```

-continued

```
Cys Lys Ala Ser Gly Tyr Thr Phe Thr Asn Phe Tyr Ile His Trp Val
                180                 185                 190
Arg Arg Ala Pro Gly Gln Gly Leu Glu Trp Met Gly Ile Ile Asn Pro
            195                 200                 205
Ser Asp Gly Arg Thr Thr Tyr Ala Gln Lys Phe Gln Gly Arg Val Thr
        210                 215                 220
Met Thr Arg Asp Thr Ser Thr Ser Thr Leu Tyr Met Glu Leu Thr Ser
225                 230                 235                 240
Leu Arg Ser Glu Asp Thr Ala Val Tyr Tyr Cys Gly Arg Gly Gly His
                245                 250                 255
Tyr Ser Asn Tyr Phe Gly Gln Pro Ser Thr Trp Gly Gln Gly Thr Leu
            260                 265                 270
Val Thr Val Ser Ser Val Glu Ala Ser
            275                 280

<210> SEQ ID NO 7
<211> LENGTH: 273
<212> TYPE: PRT
<213> ORGANISM: Homo sapiens

<400> SEQUENCE: 7

Met Lys Lys Thr Ala Ile Ala Ile Ala Val Ala Leu Ala Gly Phe Ala
1               5                   10                  15
Thr Val Ala Gln Ala Asp Tyr Lys Asp Asp Asp Lys Leu Gln Pro
            20                  25                  30
Val Leu Thr Gln Pro Ser Ser Ala Ser Gly Thr Pro Gly Gln Arg Val
            35                  40                  45
Thr Ile Ser Cys Ser Gly Ser Ser Asn Ile Gly Ser Asn Tyr Val
        50                  55                  60
Tyr Trp Tyr Gln Gln Leu Pro Gly Thr Ala Pro Lys Leu Leu Ile Tyr
65                  70                  75                  80
Arg Asn Asn Gln Arg Pro Ser Gly Val Pro Asp Arg Phe Ser Gly Ser
                85                  90                  95
Lys Ser Gly Thr Ser Ala Ser Leu Ala Ile Ser Gly Leu Gln Ser Glu
            100                 105                 110
Asp Glu Ala Asp Tyr Tyr Cys Ala Ala Trp Asp Asp Thr Leu Ile Gly
        115                 120                 125
Pro Val Phe Gly Gly Gly Thr Lys Leu Thr Val Leu Gly Glu Gly Lys
    130                 135                 140
Ser Ser Gly Ser Gly Ser Glu Ser Lys Ala Ser Glu Val Gln Leu Val
145                 150                 155                 160
Glu Ser Gly Gly Gly Leu Val Lys Pro Gly Gly Ser Leu Thr Leu Ser
                165                 170                 175
Cys Ala Val Ser Gly Phe Pro Phe Ser Asp Ala Trp Met Asn Trp Val
            180                 185                 190
Arg Gln Ala Pro Gly Lys Gly Leu Glu Trp Val Gly Arg Ile Arg Ser
            195                 200                 205
Lys Ala Gly Gly Gly Thr Thr Asp Ser Ala Ala Pro Val Lys Asp Arg
        210                 215                 220
Phe Thr Phe Ser Asp Asp Ser Lys Asn Thr Val Tyr Val Glu Met
225                 230                 235                 240
Asn Ser Leu Lys Ile Glu Asp Thr Ala Val Tyr Tyr Cys Thr Gly Glu
                245                 250                 255
Gly Tyr Trp Gly Gln Gly Thr Leu Val Thr Val Ser Ser Val Glu Ala
            260                 265                 270
```

Ser

<210> SEQ ID NO 8
<211> LENGTH: 14
<212> TYPE: PRT
<213> ORGANISM: Homo sapiens

<400> SEQUENCE: 8

Ile Leu Arg Ser Asp Phe Ser Val Val Thr Gln Arg Val Tyr
1               5                   10

<210> SEQ ID NO 9
<211> LENGTH: 5
<212> TYPE: PRT
<213> ORGANISM: Homo sapiens

<400> SEQUENCE: 9

Thr Tyr Asp Ile Tyr
1               5

<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10
ccctgtatgc ctctggtc                                                 18

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
gtctttacgg atgtcaacg                                                19

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
tttgcttcca tgctaatgcg aaag                                          24

<210> SEQ ID NO 13
<211> LENGTH: 25
<212> TYPE: DNA
<213> ORGANISM: Artificial Sequence
<220> FEATURE:
<223> OTHER INFORMATION: primer

<400> SEQUENCE: 13
gctctgttga ggtctaaagg ctccg                                         25

<210> SEQ ID NO 14
<211> LENGTH: 20
<212> TYPE: DNA
<213> ORGANISM: Artificial Sequence
<220> FEATURE:

<223> OTHER INFORMATION: primer

<400> SEQUENCE: 14
tgggaaatcg tggaaatgag                    20

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
ctgaaggact ctggctttgt c                    21

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
cagaagaatg gaagagtcag                    20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
cagatatgca gggagtcacc                    20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
agcgggaaga gaaaaaccag                    20

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
agatgaccac cagtagcagg ag                    22

<210> SEQ ID NO 20
<211> LENGTH: 13
<212> TYPE: PRT
<213> ORGANISM: Mus musculus

<400> SEQUENCE: 20

Ala Ala Asn Glu Trp Val Phe Gly Asn Ile Met Cys Lys
1               5                   10

<210> SEQ ID NO 21

```
<211> LENGTH: 18
<212> TYPE: PRT
<213> ORGANISM: Mus musculus

<400> SEQUENCE: 21

Gln Glu Ser Leu Gly Met Ser Asn Cys Val Ile Asp Lys His Leu Asp
1               5                   10                  15

Gln Lys

<210> SEQ ID NO 22
<211> LENGTH: 10
<212> TYPE: PRT
<213> ORGANISM: Homo sapiens

<400> SEQUENCE: 22

Asn Ser Asp Ser Asp Lys Arg Leu Gly Ser
1               5                   10

<210> SEQ ID NO 23
<211> LENGTH: 9
<212> TYPE: PRT
<213> ORGANISM: Homo sapiens

<400> SEQUENCE: 23

Val Ile Trp His Asn Ser Ala Val Val
1               5

<210> SEQ ID NO 24
<211> LENGTH: 5
<212> TYPE: PRT
<213> ORGANISM: Homo sapiens

<400> SEQUENCE: 24

Ser Tyr Trp Ile Gly
1               5

<210> SEQ ID NO 25
<211> LENGTH: 17
<212> TYPE: PRT
<213> ORGANISM: Homo sapiens

<400> SEQUENCE: 25

Ile Ile Tyr Pro Gly Asp Ser Asp Thr Arg Tyr Ser Pro Ser Phe Gln
1               5                   10                  15

Gly

<210> SEQ ID NO 26
<211> LENGTH: 14
<212> TYPE: PRT
<213> ORGANISM: Homo sapiens

<400> SEQUENCE: 26

Arg Pro Gln Tyr Tyr Asp Ile Leu Thr Gly Trp His Ala Gly
1               5                   10

<210> SEQ ID NO 27
<211> LENGTH: 13
<212> TYPE: PRT
<213> ORGANISM: Homo sapiens

<400> SEQUENCE: 27

Ser Gly Ser Ser Ser Asn Ile Gly Asn Asn Tyr Val Ser
1               5                   10
```

<210> SEQ ID NO 28
<211> LENGTH: 7
<212> TYPE: PRT
<213> ORGANISM: Homo sapiens

<400> SEQUENCE: 28

Gly Asn Asn Lys Arg Pro Ser
1               5

<210> SEQ ID NO 29
<211> LENGTH: 11
<212> TYPE: PRT
<213> ORGANISM: Homo sapiens

<400> SEQUENCE: 29

Ala Thr Trp Asp Asp Ser Leu Ser Ala Val Val
1               5                   10

<210> SEQ ID NO 30
<211> LENGTH: 5
<212> TYPE: PRT
<213> ORGANISM: Homo sapiens

<400> SEQUENCE: 30

Asn Phe Tyr Ile His
1               5

<210> SEQ ID NO 31
<211> LENGTH: 17
<212> TYPE: PRT
<213> ORGANISM: Homo sapiens

<400> SEQUENCE: 31

Ile Ile Asn Pro Ser Asp Gly Arg Thr Thr Tyr Ala Gln Lys Phe Gln
1               5                   10                  15

Gly

<210> SEQ ID NO 32
<211> LENGTH: 10
<212> TYPE: PRT
<213> ORGANISM: Homo sapiens

<400> SEQUENCE: 32

Gly Gly His Tyr Ser Asn Tyr Phe Gly Gln
1               5                   10

<210> SEQ ID NO 33
<211> LENGTH: 13
<212> TYPE: PRT
<213> ORGANISM: Homo sapiens

<400> SEQUENCE: 33

Ser Gly Ser Ser Ser Asn Ile Gly Ser Asn Tyr Val Tyr
1               5                   10

<210> SEQ ID NO 34
<211> LENGTH: 7
<212> TYPE: PRT
<213> ORGANISM: Homo sapiens

<400> SEQUENCE: 34

Arg Asn Asn Gln Arg Pro Ser
1               5

```
<210> SEQ ID NO 35
<211> LENGTH: 11
<212> TYPE: PRT
<213> ORGANISM: Homo sapiens

<400> SEQUENCE: 35

Ala Ala Trp Asp Asp Ser Leu Asn Gly Val Val
1               5                   10

<210> SEQ ID NO 36
<211> LENGTH: 13
<212> TYPE: PRT
<213> ORGANISM: Homo sapiens

<400> SEQUENCE: 36

Lys Ala Ser Gly Tyr Thr Phe Thr Ser Tyr Tyr Met His
1               5                   10

<210> SEQ ID NO 37
<211> LENGTH: 7
<212> TYPE: PRT
<213> ORGANISM: Homo sapiens

<400> SEQUENCE: 37

Asn Pro Ser Gly Gly Ser Thr
1               5

<210> SEQ ID NO 38
<211> LENGTH: 9
<212> TYPE: PRT
<213> ORGANISM: Homo sapiens

<400> SEQUENCE: 38

Ala Arg Asp Gly Asn Trp Phe Asp Pro
1               5

<210> SEQ ID NO 39
<211> LENGTH: 5
<212> TYPE: PRT
<213> ORGANISM: Homo sapiens

<400> SEQUENCE: 39

Ser Ser Tyr Leu Ala
1               5

<210> SEQ ID NO 40
<211> LENGTH: 17
<212> TYPE: PRT
<213> ORGANISM: Homo sapiens

<400> SEQUENCE: 40

Ile Tyr Gly Ala Ser Ser Arg Ala Thr Gly Ile Pro Asp Arg Phe Ser
1               5                   10                  15

Gly

<210> SEQ ID NO 41
<211> LENGTH: 5
<212> TYPE: PRT
<213> ORGANISM: Homo sapiens

<400> SEQUENCE: 41

Gln Tyr Gly Ser Ser
1               5
```

```
<210> SEQ ID NO 42
<211> LENGTH: 12
<212> TYPE: PRT
<213> ORGANISM: Homo sapiens

<400> SEQUENCE: 42

Arg Ala Ser Gln Ser Val Ser Ser Ser Tyr Leu Ala
1               5                   10

<210> SEQ ID NO 43
<211> LENGTH: 7
<212> TYPE: PRT
<213> ORGANISM: Homo sapiens

<400> SEQUENCE: 43

Gly Ala Ser Ser Arg Ala Thr
1               5

<210> SEQ ID NO 44
<211> LENGTH: 8
<212> TYPE: PRT
<213> ORGANISM: Homo sapiens

<400> SEQUENCE: 44

Gln Gln Tyr Gly Ser Ser Leu Thr
1               5

<210> SEQ ID NO 45
<211> LENGTH: 17
<212> TYPE: PRT
<213> ORGANISM: Homo sapiens

<400> SEQUENCE: 45

Trp Val Asn Pro Asp Asn Gly Lys Thr Asp Tyr Ala Gln Lys Phe Gln
1               5                   10                  15

Gly

<210> SEQ ID NO 46
<211> LENGTH: 8
<212> TYPE: PRT
<213> ORGANISM: Homo sapiens

<400> SEQUENCE: 46

Ala Leu Thr Arg Trp Gln Gln Ser
1               5

<210> SEQ ID NO 47
<211> LENGTH: 13
<212> TYPE: PRT
<213> ORGANISM: Homo sapiens

<400> SEQUENCE: 47

Ser Gly Ser Ser Ser Asn Ile Gly Ser His Thr Val Asn
1               5                   10

<210> SEQ ID NO 48
<211> LENGTH: 11
<212> TYPE: PRT
<213> ORGANISM: Homo sapiens

<400> SEQUENCE: 48

Ala Ala Trp Asp Asp Ser Leu Ser Gly Val Val
1               5                   10
```

<210> SEQ ID NO 49
<211> LENGTH: 13
<212> TYPE: PRT
<213> ORGANISM: Homo sapiens

<400> SEQUENCE: 49

```
Gly Gly His Tyr Ser Asn Tyr Phe Gly Gln Pro Ser Thr
1               5                   10
```

<210> SEQ ID NO 50
<211> LENGTH: 11
<212> TYPE: PRT
<213> ORGANISM: Homo sapiens

<400> SEQUENCE: 50

```
Ala Ala Trp Asp Asp Thr Leu Ile Gly Pro Val
1               5                   10
```

<210> SEQ ID NO 51
<211> LENGTH: 5
<212> TYPE: PRT
<213> ORGANISM: Homo sapiens

<400> SEQUENCE: 51

```
Asp Ala Trp Met Asn
1               5
```

<210> SEQ ID NO 52
<211> LENGTH: 19
<212> TYPE: PRT
<213> ORGANISM: Homo sapiens

<400> SEQUENCE: 52

```
Arg Ile Arg Ser Lys Ala Gly Gly Thr Thr Asp Ser Ala Ala Pro
1               5                   10                  15

Val Lys Asp
```

<210> SEQ ID NO 53
<211> LENGTH: 258
<212> TYPE: PRT
<213> ORGANISM: Homo sapiens

<400> SEQUENCE: 53

```
Leu Gln Ala Val Leu Thr Gln Pro Ser Ser Leu Ser Ala Ser Pro Gly
1               5                   10                  15

Ala Ser Ala Ser Leu Thr Cys Ile Leu Arg Ser Asp Phe Ser Val Val
                20                  25                  30

Thr Gln Arg Val Tyr Trp Tyr Gln Gln Lys Pro Gly Ser Pro Pro Arg
            35                  40                  45

Tyr Leu Leu Arg Tyr Asn Ser Asp Ser Asp Lys Arg Leu Gly Ser Gly
        50                  55                  60

Val Pro Ser Arg Phe Ser Gly Ser Lys Asp Val Ser Ala Asn Ala Ala
65                  70                  75                  80

Ser Leu Leu Ile Ser Gly Leu Gln Ser Asp Asp Glu Ala Asp Tyr Tyr
                85                  90                  95

Cys Val Ile Trp His Asn Ser Ala Val Val Phe Gly Gly Gly Thr Lys
            100                 105                 110

Leu Thr Val Leu Gly Glu Gly Lys Ser Ser Gly Ser Gly Ser Glu Ser
        115                 120                 125

Lys Ala Ser Glu Val Gln Leu Leu Glu Ser Gly Ala Glu Val Lys Lys
```

```
                130                 135                 140
Pro Gly Glu Ser Leu Lys Ile Ser Cys Lys Gly Ser Gly Tyr Ser Phe
145                 150                 155                 160

Thr Ser Tyr Trp Ile Gly Trp Val Arg Gln Met Pro Gly Lys Gly Leu
                165                 170                 175

Glu Trp Met Gly Ile Ile Tyr Pro Gly Asp Ser Asp Thr Arg Tyr Ser
                180                 185                 190

Pro Ser Phe Gln Gly Gln Val Thr Ile Ser Ala Asp Lys Ser Ile Ser
                195                 200                 205

Thr Ala Tyr Leu Gln Trp Ser Ser Leu Lys Ala Ser Asp Thr Ala Met
                210                 215                 220

Tyr Tyr Cys Ala Arg Arg Pro Gln Tyr Tyr Asp Ile Leu Thr Gly Trp
225                 230                 235                 240

His Ala Gly Trp Phe Asp Pro Trp Gly Gln Gly Thr Leu Val Thr Val
                245                 250                 255

Ser Ser
```

<210> SEQ ID NO 54
<211> LENGTH: 248
<212> TYPE: PRT
<213> ORGANISM: Homo sapiens

<400> SEQUENCE: 54

```
Leu Gln Ser Val Leu Thr Gln Pro Pro Ser Val Ser Gly Ala Pro Gly
1               5                   10                  15

Gln Lys Val Thr Ile Ser Cys Ser Gly Ser Ser Ser Asn Ile Gly Asn
                20                  25                  30

Asn Tyr Val Ser Trp Tyr Gln Gln Leu Pro Gly Thr Ala Pro Lys Leu
                35                  40                  45

Leu Ile Tyr Gly Asn Asn Lys Arg Pro Ser Gly Ile Pro Asp Arg Phe
            50                  55                  60

Ser Gly Ser Lys Ser Gly Thr Ser Ala Thr Leu Gly Ile Thr Gly Leu
65                  70                  75                  80

Gln Thr Gly Asp Glu Ala Asp Tyr Tyr Cys Ala Thr Trp Asp Asp Ser
                85                  90                  95

Leu Ser Ala Val Val Phe Gly Gly Thr Lys Leu Thr Val Leu Gly
                100                 105                 110

Glu Gly Lys Ser Ser Gly Ser Gly Ser Glu Ser Lys Ala Ser Gln Val
            115                 120                 125

Thr Leu Lys Glu Ser Gly Ala Glu Val Lys Lys Pro Gly Ala Ser Val
            130                 135                 140

Lys Val Ser Cys Lys Ala Ser Gly Tyr Thr Phe Thr Asn Phe Tyr Ile
145                 150                 155                 160

His Trp Val Arg Arg Ala Pro Gly Gln Gly Leu Glu Trp Met Gly Ile
                165                 170                 175

Ile Asn Pro Ser Asp Gly Arg Thr Thr Tyr Ala Gln Lys Phe Gln Gly
                180                 185                 190

Arg Val Thr Met Thr Arg Asp Thr Ser Thr Ser Thr Leu Tyr Met Glu
                195                 200                 205

Leu Thr Ser Leu Arg Ser Glu Asp Thr Ala Val Tyr Tyr Cys Gly Arg
                210                 215                 220

Gly Gly His Tyr Ser Asn Tyr Phe Gly Gln Pro Ser Thr Trp Gly Gln
225                 230                 235                 240

Gly Thr Leu Val Thr Val Ser Ser
```

-continued

```
                        245

<210> SEQ ID NO 55
<211> LENGTH: 248
<212> TYPE: PRT
<213> ORGANISM: Homo sapiens

<400> SEQUENCE: 55

Leu Gln Ser Val Leu Thr Gln Pro Pro Ser Ala Ser Gly Thr Pro Gly
1               5                   10                  15

Gln Arg Val Thr Ile Ser Cys Ser Gly Ser Ser Ser Asn Ile Gly Ser
            20                  25                  30

Asn Tyr Val Tyr Trp Tyr Gln Leu Pro Gly Thr Ala Pro Lys Leu
        35                  40                  45

Leu Ile Tyr Arg Asn Asn Gln Arg Pro Ser Gly Val Pro Asp Arg Phe
50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Asp Ser
                85                  90                  95

Leu Asn Gly Val Val Phe Gly Gly Gly Thr Glu Leu Thr Val Leu Gly
            100                 105                 110

Glu Gly Lys Ser Ser Gly Ser Gly Ser Glu Ser Lys Ala Ser Gln Val
        115                 120                 125

Thr Leu Lys Glu Ser Gly Ala Glu Val Lys Lys Pro Gly Ala Ser Val
130                 135                 140

Lys Val Ser Cys Lys Ala Ser Gly Tyr Thr Phe Thr Asn Phe Tyr Ile
145                 150                 155                 160

His Trp Val Arg Arg Ala Pro Gly Gln Gly Leu Glu Trp Met Gly Ile
                165                 170                 175

Ile Asn Pro Ser Asp Gly Arg Thr Thr Tyr Ala Gln Lys Phe Gln Gly
            180                 185                 190

Arg Val Thr Met Thr Arg Asp Thr Ser Thr Ser Thr Leu Tyr Met Glu
        195                 200                 205

Leu Thr Ser Leu Arg Ser Glu Asp Thr Ala Val Tyr Tyr Cys Gly Arg
    210                 215                 220

Gly Gly His Tyr Ser Asn Tyr Phe Gly Gln Pro Ser Thr Trp Gly Gln
225                 230                 235                 240

Gly Thr Leu Val Thr Val Ser Ser
                245

<210> SEQ ID NO 56
<211> LENGTH: 241
<212> TYPE: PRT
<213> ORGANISM: Homo sapiens

<400> SEQUENCE: 56

Leu Glu Val Gln Leu Val Glu Ser Gly Ala Glu Val Lys Lys Pro Gly
1               5                   10                  15

Ala Ser Val Lys Val Ser Cys Lys Ala Ser Gly Tyr Thr Phe Thr Ser
            20                  25                  30

Tyr Tyr Met His Trp Val Arg Gln Ala Pro Gly Gln Gly Leu Glu Trp
        35                  40                  45

Met Gly Ile Ile Asn Pro Ser Gly Gly Ser Thr Ser Tyr Ala Gln Lys
50                  55                  60

Phe Gln Gly Arg Val Thr Met Thr Arg Asp Thr Ser Thr Ser Thr Val
```

```
                65                  70                  75                  80
Tyr Met Glu Leu Ser Ser Leu Arg Ser Glu Asp Thr Ala Val Tyr Tyr
                    85                  90                  95

Cys Ala Arg Asp Gly Asn Trp Phe Asp Pro Trp Gly Gln Gly Thr Leu
                100                 105                 110

Val Thr Val Ser Ser Gly Gly Lys Ser Ser Gly Ser Gly Ser Glu
                115                 120                 125

Ser Lys Ala Ser Glu Ile Val Met Thr Gln Ser Pro Gly Thr Leu Ser
145                 150                 155                 160

Leu Ser Pro Gly Glu Arg Ala Thr Leu Ser Cys Arg Ala Ser Gln Ser
145                 150                 155                 160

Val Ser Ser Ser Tyr Leu Ala Trp Tyr Gln Gln Lys Pro Gly Gln Ala
                165                 170                 175

Pro Arg Leu Leu Ile Tyr Gly Ala Ser Ser Arg Ala Thr Gly Ile Pro
                180                 185                 190

Asp Arg Phe Ser Gly Ser Gly Ser Gly Thr Asp Phe Thr Leu Thr Ile
                195                 200                 205

Ser Arg Leu Glu Pro Glu Asp Phe Ala Val Tyr Tyr Cys Gln Gln Tyr
210                 215                 220

Gly Ser Ser Pro Pro Leu Thr Phe Gly Gly Gly Thr Lys Leu Asp Ile
225                 230                 235                 240

Lys

<210> SEQ ID NO 57
<211> LENGTH: 243
<212> TYPE: PRT
<213> ORGANISM: Homo sapiens

<400> SEQUENCE: 57

Leu Glu Ile Val Leu Thr Gln Ser Pro Gly Thr Leu Ser Leu Ser Pro
1               5                   10                  15

Gly Glu Arg Ala Thr Leu Ser Cys Arg Ala Ser Gln Ser Val Ser Ser
                20                  25                  30

Ser Tyr Leu Ala Trp Tyr Gln Gln Lys Pro Gly Gln Ala Pro Arg Leu
            35                  40                  45

Leu Ile Tyr Gly Ala Ser Ser Arg Ala Thr Gly Ile Pro Asp Arg Phe
        50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Gln Gln Tyr Gly Ser Ser
                85                  90                  95

Leu Thr Phe Gly Gly Gly Thr Lys Val Glu Ile Lys Glu Gly Lys Ser
                100                 105                 110

Ser Gly Ser Gly Ser Glu Ser Lys Ala Ser Glu Val Gln Leu Leu Glu
            115                 120                 125

Ser Gly Ala Glu Val Lys Lys Pro Gly Ala Ser Val Lys Val Ser Cys
        130                 135                 140

Lys Thr Ser Gly Tyr Thr Phe Thr Thr Tyr Asp Ile Tyr Trp Met Arg
145                 150                 155                 160

Leu Ala Thr Gly Gln Arg Leu Glu Trp Met Gly Trp Val Asn Pro Asp
                165                 170                 175

Asn Gly Lys Thr Asp Tyr Ala Gln Lys Phe Gln Gly Arg Val Thr Ile
                180                 185                 190

Ser Arg Asp Ser Ser Ile Asn Thr Val Phe Met Glu Leu Ser Asn Leu
```

```
            195                 200                 205
Arg Leu Glu Asp Thr Ala Ile Tyr Phe Cys Ala Arg Ala Leu Thr Arg
    210                 215                 220

Trp Gln Gln Ser Pro Leu Gly Tyr Trp Gly Gln Gly Thr Leu Val Thr
225                 230                 235                 240

Val Ser Ser

<210> SEQ ID NO 58
<211> LENGTH: 45
<212> TYPE: PRT
<213> ORGANISM: Homo sapiens

<400> SEQUENCE: 58

Met Glu Asp Asn Asn Met Leu Pro Gln Phe Ile His Gly Ile Leu Ser
1               5                   10                  15

Thr Ser His Ser Leu Phe Thr Arg Ser Ile Gln Glu Leu Asp Glu Gly
            20                  25                  30

Ala Thr Thr Pro Tyr Asp Tyr Asp Asp Gly Glu Pro Cys
        35                  40                  45

<210> SEQ ID NO 59
<211> LENGTH: 6
<212> TYPE: PRT
<213> ORGANISM: Homo sapiens

<400> SEQUENCE: 59

Gly Ser Gly Ser Gly Ser
1               5

<210> SEQ ID NO 60
<211> LENGTH: 28
<212> TYPE: PRT
<213> ORGANISM: Homo sapiens

<400> SEQUENCE: 60

Thr Lys Cys Gln Lys Glu Asp Ser Val Tyr Val Cys Gly Pro Tyr Phe
1               5                   10                  15

Pro Arg Gly Trp Asn Asn Phe His Thr Ile Met Arg
            20                  25

<210> SEQ ID NO 61
<211> LENGTH: 242
<212> TYPE: PRT
<213> ORGANISM: Homo sapiens

<400> SEQUENCE: 61

Leu Glu Ile Val Leu Thr Gln Ser Pro Gly Thr Leu Ser Leu Ser Pro
1               5                   10                  15

Gly Glu Arg Ala Thr Leu Ser Cys Arg Ala Ser Gln Ser Val Ser Ser
            20                  25                  30

Ser Tyr Leu Ala Trp Tyr Gln Gln Lys Pro Gly Gln Ala Pro Arg Leu
        35                  40                  45

Leu Ile Tyr Gly Ala Ser Ser Arg Ala Thr Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Gln Gln Tyr Gly Ser Ser
                85                  90                  95

Leu Thr Phe Gly Gly Gly Thr Lys Val Glu Ile Lys Glu Gly Lys Ser
```

-continued

```
             100                 105                 110
Ser Gly Ser Gly Ser Glu Ser Lys Ala Ser Glu Val Gln Leu Leu Glu
            115                 120                 125

Ser Gly Ala Glu Val Lys Lys Pro Gly Ala Ser Val Lys Val Ser Cys
            130                 135                 140

Lys Thr Ser Gly Tyr Thr Phe Thr Thr Tyr Asp Ile Tyr Trp Met Arg
145                 150                 155                 160

Leu Ala Thr Gly Gln Arg Leu Glu Trp Met Gly Trp Val Asn Pro Asp
                    165                 170                 175

Asn Gly Lys Thr Asp Tyr Ala Gln Lys Phe Gln Gly Arg Val Thr Ile
                180                 185                 190

Ser Arg Asp Ser Ser Ile Asn Thr Val Phe Met Glu Leu Ser Asn Leu
            195                 200                 205

Arg Leu Glu Asp Thr Ala Ile Tyr Phe Cys Ala Arg Ala Leu Thr Arg
            210                 215                 220

Trp Gln Gln Ser Pro Leu Gly Tyr Trp Gly Gln Gly Thr Leu Val Thr
225                 230                 235                 240

Val Ser
```

COMPOSITIONS AND METHODS TO BLOCK AND BIND CCR2 TO MODULATE CELLULAR FUNCTION

CROSS-REFERENCE TO RELATED APPLICATIONS

This application claims priority to U.S. Provisional application No. 62/846,947, filed on May 13, 2019, the disclosure of which is incorporated herein by reference.

SEQUENCE LISTING

The instant application contains a Sequence Listing which has been submitted electronically in txt format and is hereby incorporated by reference in its entirety. Said txt copy was created on May 14, 2020, is named "011520_01502_ST25.txt" and is 38,900 bytes in size.

STATEMENT REGARDING FEDERALLY SPONSORED RESEARCH

This invention was made with government support under EB023262 awarded by the National Institutes of Health. The government has certain rights in the invention.

BACKGROUND OF THE DISCLOSURE

Monocytes migrate to sites of inflammation under the influence of chemokines and cytokines. The CCR2 chemokine receptor mediates monocyte egress from the bone marrow under the influence of the chemokine CCL2, which is secreted by cells during inflammatory conditions including myocardial infarction, cancer, atherosclerosis, asthma, and rheumatoid arthritis.[1-3]

At sites of inflammation, monocytes differentiate into functionally polarized macrophages in response to chemokines, cytokines, and other chemical factors. There are two main macrophage phenotypes: M1 and M2.[4] M1 macrophage activation generally occurs in the presence of lipopolysaccharide (LPS),[5] interferon gamma (IFN-γ),[6] and granulocyte-macrophage colony stimulating factor (GM-CSF).[7] M1 macrophages are considered pro-inflammatory and essential early responders at inflammatory disease onset. Macrophage colony-stimulating factor (M-CSF)[7] and specific interleukins (IL-4, IL-13, IL-10)[8-10] induce M2 macrophage activation, which is considered anti-inflammatory. While M2 macrophages are beneficial in the reparative phase of inflammation and contribute to wound healing after myocardial infarction, they can be detrimental in tumors as they promote tumor growth through increased angiogenesis and metastasis and suppression of anti-cancer immune responses.[11-13]

In addition to driving monocyte migration, CCL2 signaling also contributes to M2 macrophage polarization.[14, 15] As the N-terminal domain (NTD) of the CCR2 receptor captures CCL2 to trigger downstream effects,[16, 17] the CCR2 NTD represents an ideal target to disrupt the CCR2/CCL2 axis for therapeutic benefit.[18] While several antibodies targeting the CCL2/CCR2 pathway have shown promise in clinical trials in myocardial infarction, atherosclerosis, and cancer,[19-23] none are clinically approved despite initial expectations. Thus, there remains a need to capitalize on antibody binding specificity while finding novel ways to improve efficacy.

SUMMARY OF THE DISCLOSURE

The present disclosure provides antibodies, compositions, and methods that inhibit chemokine ligand 2 (CCL2) from binding to the chemokine receptor type 2 (CCR2). The disclosure provides isolated antibodies including fragments and variants thereof. In an embodiment, the antibodies are single chain variable fragment (scFvs) antibodies directed against the N-terminal or extracellular loop (ECL) domains of CCR2. Binding of these scFvs to CCR2 inhibits the binding of CCL2 to CCR2, thus blocking downstream signaling events. The disclosure also provides compositions comprising the scFvs, and methods of using the scFvs or compositions for inhibiting binding of CCL2 to CCR2 for the treatment of a medical condition such as cancer.

In an aspect, the present antibodies, such as scFvs specifically bind to CCR2 relative to other chemokine receptors. The scFvs and compositions described in this disclosure can be used for treatment of conditions in which there is abnormal CCL2/CCR2 binding resulting in the recruitment of immune cells and their subsequent polarization to an immune suppressive phenotype, or in which a reduction in CCL2/CCR2 binding is desired. Conditions such as these often arise in diseases such as cancer.

Despite the important role of the tumor stroma in cancer progression, the vast majority of anticancer therapies target cancer cells and not the tumor microenvironment. This disclosure provides a therapeutic strategy that not only inhibits inflammatory monocyte migration to the tumor but also polarizes tumor associated macrophages (TAMs) towards the tumor-suppressive M1 phenotype and away from the immune-suppressive M2 phenotype by blocking the CCL2/CCR2 pathway. Antibodies and small molecules targeting the CCL2/CCR2 pathway have shown promise in clinical trials, but these are suboptimal and there remains a need for building upon antibody binding specificity and new ways to improve efficacy.

This disclosure also provides a method of treating a tumor in an individual in need of treatment comprising administering to the individual one or more scFvs or a composition comprising one or more scFvs that are specific for CCR2, such as, for example, human CCR2. Additionally, this disclosure includes methods and compositions for inhibiting metastasis and/or angiogenesis using the described antibodies.

BRIEF DESCRIPTION OF THE FIGURES

For a fuller understanding of the nature and objects of the disclosure, reference should be made to the following detailed description taken in conjunction with the accompanying figures.

FIG. 21. Phamacokinetic profile of PEG(40K)-NTD-scFv compared to unpegylated NTD-scFv in female Balb/c mice. Data are presented as mean±sd, n=3.

DETAILED DESCRIPTION OF THE DISCLOSURE

Figure 1:
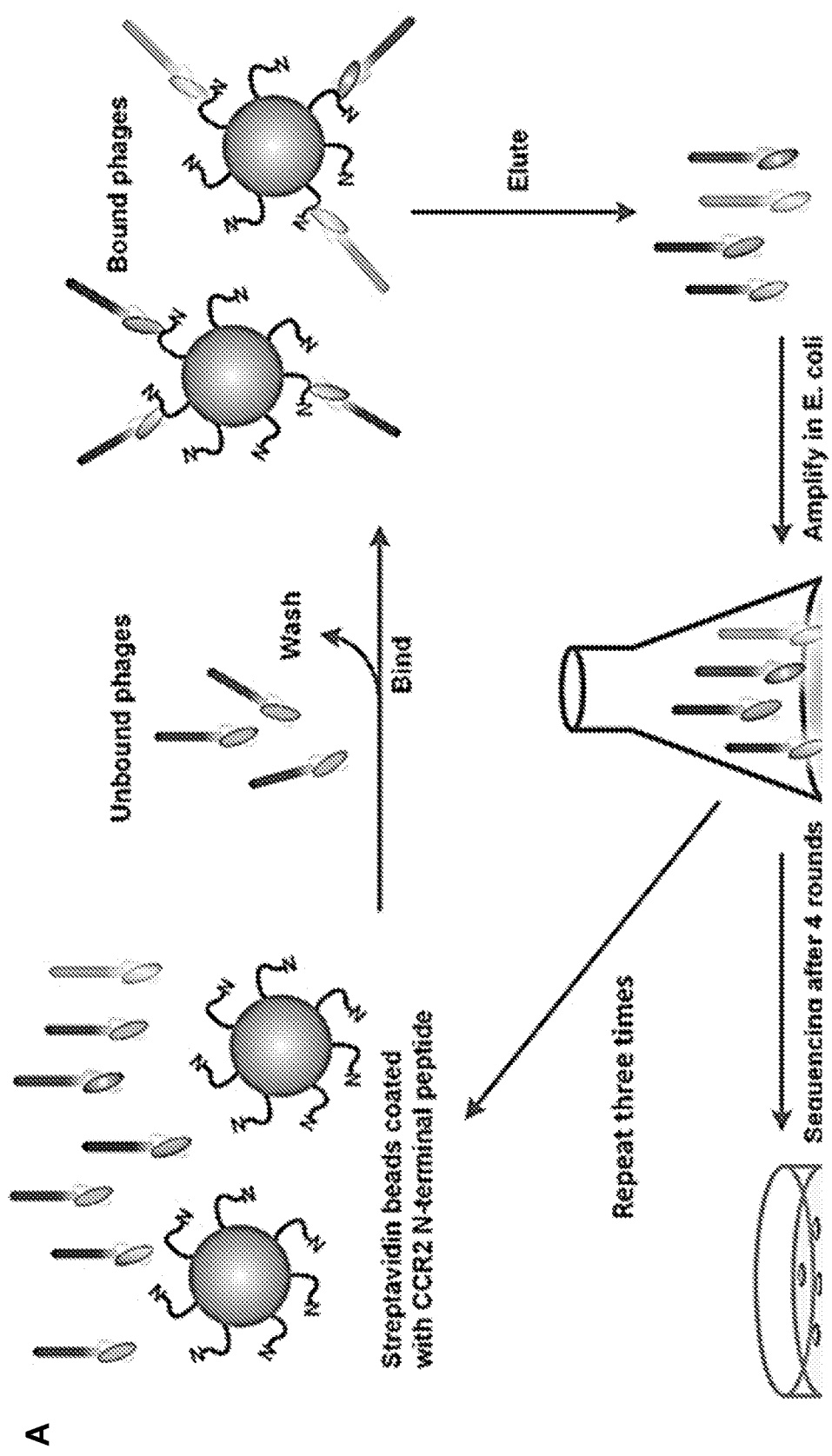
FIG. 1. Schematic of phage display screening against the CCR2 N-terminal peptide domain (A). The top five clones showing the highest affinity to the CCR2 N-terminus were sequenced (clones 13F (SEQ ID NO:53), 25B (SEQ ID NO:54), 26B (SEQ ID NO:55), 37B (SEQ ID NO:56), and 58C (SEQ ID NO:57)) (B). The top 2 clones showing highest affinity to the CCR2 ECL2 were sequenced (clones 4h (SEQ ID NO:6) and 11b (SEQ ID NO:7)) (B). For each group of scFvs (NTD or ECL2) the framework regions (light and heavy chains, shaded) and complementarity determining regions (light and heavy chains; CDRL and CDRH, labeled and underlined) are aligned and compared. Linker sequences are identified by the dashed line.

Although claimed subject matter is described in terms of certain embodiments/examples, other embodiments/examples, including embodiments/examples that do not provide all of the benefits and features set forth herein, are also within the scope of this disclosure. Various structural, logical, and process step changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

Throughout this application, the singular form encompasses the plural and vice versa. All sections of this application, including any supplementary sections or figures, are fully a part of this application.

The term "treatment" as used herein refers to alleviation of one or more symptoms or features associated with the presence of the particular condition or suspected condition being treated. Treatment does not necessarily mean complete cure or remission, nor does it preclude recurrence or relapses. Treatment can be effected over a short term, over a medium term, or can be a long-term treatment, such as, within the context of a maintenance therapy. Treatment can be continuous or intermittent.

The term "therapeutically effective amount" as used herein refers to an amount of an agent sufficient to achieve, in a single or multiple doses, the intended purpose of treatment. The exact amount desired or required will vary depending on the particular compound or composition used, its mode of administration, patient specifics and the like. Appropriate effective amount can be determined by one of ordinary skill in the art informed by the instant disclosure using only routine experimentation.

This disclosure provides single chain variable fragment (scFv) antibodies, vectors or cells comprising nucleic acids encoding scFvs, all nucleotide sequences encoding the scFvs described herein, compositions comprising any of the foregoing, methods of making any of the foregoing, and methods of using the scFvs or nucleic acid molecules in the treatment of conditions involving CCR2/CCL2 binding. This disclosure includes all amino acid sequences described herein and all contiguous segments thereof that are 3-25 amino acids in length, inclusive, and including all integers and ranges of integers there between. In embodiments, each CDR amino acid sequence of each antibody of this disclosure is included as a distinct sequence.

While specific sequences are listed in this disclosure, it will be appreciated that amino acid changes/substitutions may be made in the sequences without affecting the function/activity. such, sequences which are 85%, 90%, 95%, 96%, 97%, 98% and 99% identical to the sequences disclosed herein or to the nucleotide sequences encoding the amino acid sequences disclosed herein are considered to be part of the disclosure.

The ECL2 of CCR2 can be represented by the sequence

```
                                          (SEQ ID NO: 60)
TKCQKEDSVYVCGPYFPRGWNNFHTIMR.
```

In an embodiment the scFv antibodies of the present disclosure comprise the following sequences:

Examples of scFv sequences against the N-terminal domain:

```
13F-scFv:
                                           (SEQ ID NO: 1)
MKKTAIAIAVALAGFATVAQADYKDDDDKLQAVLTQPSSLSASPGASASLT
CILRSDFSVVTQRVYWYQQKPGSPPRYLLRYNSDSDKRLGSGVPSRFSGSK
DVSANAASLLISGLQSDDEADYYCVIWHNSAVVFGGGTKLTVLGEGKSSGS
GSESKASEVQLLESGAEVKKPGESLKISCKGSGYSFTSYWIGWVRQMPGKG
LEWMGIIYPGDSDTRYSPSFQGQVTISADKSISTAYLQWSSLKASDTAMYY
CARRPQYYDILTGWHAGWFDPWGQGTLVTVSSVEASAAALDYKDDDDKLDH
HHHHH 25B-scFv:
                                           (SEQ ID NO: 2)
MKKTAIAIAVALAGFATVAQADYKDDDDKLQSVLTQPPSVSGAPGQKVTIS
CSGSSSNIGNNYVSWYQQLPGTAPKLLIYGNNKRPSGIPDRFSGSKSGTSA
TLGITGLQTGDEADYYCATWDDSLSAVVFGGGTKLTVLGEGKSSGSGSESK
ASQVTLKESGAEVKKPGASVKVSCKASGYTFTNFYIHWVRRAPGQGLEWMG
IINPSDGRTTYAQKFQGRVTMTRDTSTSTLYMELTSLRSEDTAVYYCGRGG
HYSNYFGQPSTWGQGTLVTVSSVEASAAALDYKDDDDKLDHHHHHH 26B-scFv:
                                           (SEQ ID NO: 3)
MKKTAIAIAVALAGFATVAQADYKDDDDKLQSVLTQPPSASGTPGQRVTIS
CSGSSSNIGSNYVYWYQQLPGTAPKLLIYRNNQRPSGVPDRFSGSKSGTSA
SLAISGLQSEDEADYYCAAWDDSLNGVVFGGGTELTVLGEGKSSGSGSESK
ASQVTLKESGAEVKKPGASVKVSCKASGYTFTNFYIHWVRRAPGQGLEWMG
IINPSDGRTTYAQKFQGRVTMTRDTSTSTLYMELTSLRSEDTAVYYCGRGG
HYSNYFGQPSTWGQGTLVTVSSVEASAAALDYKDDDDKLDHHHHHH 37B-scFv:
                                           (SEQ ID NO: 4)
MKKTAIAIAVALAGFATVAQADYKDDDDKLEVQLVESGAEVKKPGASVKVS
CKASGYTFTSYYMHWVRQAPGQGLEWMGIINPSGGSTSYAQKFQGRVTMTR
DTSTSTVYMELSSLRSEDTAVYYCARDGNWFDPWGQGTLVTVSSGEGKSSG
SGSESKASEIVMTQSPGTLSLSPGERATLSCRASQSVSSSYLAWYQQKPGQ
APRLLIYGASSRATGIPDRFSGSGSGTDFTLTISRLEPEDFAVYYCQQYGS
SPPLTFGGGTKLDIKVEASAAALDYKDDDDKLDHHHHHH 58C-scFv:
                                           (SEQ ID NO: 5)
MKKTAIAIAVALAGFATVAQADYKDDDDKLEIVLTQSPGTLSLSPGERATL
SCRASQSVSSSYLAWYQQKPGQAPRLLIYGASSRATGIPDRFSGSGSGTDF
TLTISRLEPEDFAVYYCQQYGSSLTFGGGTKVEIKEGKSSGSGSESKASEV
QLLESGAEVKKPGASVKVSCKTSGYTFTTYDIYWMRLATGQRLEWMGWVNP
DNGKTDYAQKFQGRVTISRDSSINTVFMELSNLRLEDTAIYFCARALTRWQ
QSPLGYWGQGTLVTVSSVEASAAALDYKDDDDKLDHHHHHH
```

Examples of scFv sequences against the 2<sup>nd</sup> extracellular loop (ECL2) of CCR2

```
4h-scFv:
                                           (SEQ ID NO: 6)
MKKTAIAIAVALAGFATVAQADYKDDDDKLQSVLTQPPSASGTPGQRVTIS
CSGSSSNIGSHTVNWYQQLPGTAPKLLIYRNNQRPSGVPDRFSGSKSGTSA
SLAISGLRSEDEADYYCAAWDDSLSGVVFGGGTKLTVLGEGKSSGSGSESK
ASQVTLKESGAEVKKPGASVKVSCKASGYTFTNFYIHWVRRAPGQGLEWMG
IINPSDGRTTYAQKFQGRVTMTRDTSTSTLYMELTSLRSEDTAVYYCGRGG
HYSNYFGQPSTWGQGTLVTVSSVEAS 11b-scFv:
                                           (SEQ ID NO: 7)
MKKTAIAIAVALAGFATVAQADYKDDDDKLQPVLTQPSSASGTPGQRVTIS
CSGSSSNIGSNYVYWYQQLPGTAPKLLIYRNNQRPSGVPDRFSGSKSGTSA
SLAISGLQSEDEADYYCAAWDDTLIGPVFGGGTKLTVLGEGKSSGSGSESK
ASEVQLVESGGGLVKPGGSLTLSCAVSGFPFSDAWMNWVRQAPGKGLEWVG
RIRSKAGGGTTDSAAPVKDRFTFSGDDSKNTVYVEMNSLKIEDTAVYYCTG
EGYWGQGTLVTVSSVEAS
```

In embodiments, the scFvs may have sequences that lack the poly histidine sequence, signaling sequences, cleavage sequences, targeting sequences, or other non-CDR sequences. Examples of shortened versions of scFvs are listed below.

Examples of scFv sequences against the N-terminal domain:

```
Shortened version of 13F-scFv:
                                          (SEQ ID NO: 53)
LQAVLTQPSSLSASPGASASLTCILRSDFSVVTQRVYWYQQKPGSPPRYLL
RYNSDSDKRLGSGVPSRFSGSKDVSANAASLLISGLQSDDEADYYCVIWHN
SAVVFGGGTKLTVLGEGKSSGSGSESKASEVQLLESGAEVKKPGESLKISC
KGSGYSFTSYWIGWVRQMPGKGLEWMGIIYPGDSDTRYSPSFQGQVTISAD
KSISTAYLQWSSLKASDTAMYYCARRPQYYDILTGWHAGWFDPWGQGTLVT
VSS
```

-continued

Shortened version of 25B-scFv:
(SEQ ID NO: 54)
LQSVLTQPPSVSGAPGQKVTISCSGSSSNIGNNYVSWYQQLPGTAPKLLIY

GNNKRPSGIPDRFSGSKSGTSATLGITGLQTGDEADYYCATWDDSLSAVVF

GGGTKLTVLGEGKSSGSGSESKASQVTLKESGAEVKKPGASVKVSCKASGY

TFTNFYIHWVRRAPGQGLEWMGIINPSDGRTTYAQKFQGRVTMTRDTSTST

LYMELTSLRSEDTAVYYCGRGGHYSNYFGQPSTWGQGTLVTVSS

Shortened version of 26B-scFv:
(SEQ ID NO: 55)
LQSVLTQPPSASGTPGQRVTISCSGSSSNIGSNYVYWYQQLPGTAPKLLIY

RNNQRPSGVPDRFSGSKSGTSASLAISGLQSEDEADYYCAAWDDSLNGVVF

GGGTELTVLGEGKSSGSGSESKASQVTLKESGAEVKKPGASVKVSCKASGY

TFTNFYIHWVRRAPGQGLEWMGIINPSDGRTTYAQKFQGRVTMTRDTSTST

LYMELTSLRSEDTAVYYCGRGGHYSNYFGQPSTWGQGTLVTVSS

Shortened version of 37B-scFv:
(SEQ ID NO: 56)
LEVQLVESGAEVKKPGASVKVSCKASGYTFTSYYMHWVRQAPGQGLEWMGI

INPSGGSTSYAQKFQGRVTMTRDTSTSTVYMELSSLRSEDTAVYYCARDGN

WFDPWGQGTLVTVSSGEGKSSGSGSESKASEIVMTQSPGTLSLSPGERATL

SCRASQSVSSSYLAWYQQKPGQAPRLLIYGASSRATGIPDRFSGSGSGTDF

TLTISRLEPEDFAVYYCQQYGSSPPLTFGGGTKLDIK

Shortened version of 58C-scFv:
(SEQ ID NO: 57)
LEIVLTQSPGTLSLSPGERATLSCRASQSVSSSYLAWYQQKPGQAPRLLIY

GASSRATGIPDRFSGSGSGTDFTLTISRLEPEDFAVYYCQQYGSSLTFGGG

TKVEIKEGKSSGSGSESKASEVQLLESGAEVKKPGASVKVSCKTSGYTFTT

YDIYWMRLATGQRLEWMGWVNPDNGKTDYAQKFQGRVTISRDSSINTVFME

LSNLRLEDTAIYFCARALTRWQQSPLGYWGQGTLVTVSS.

An antibody of this disclosure can be a monoclonal antibody comprising a heavy chain variable region (VH) and a light chain variable region (VL) comprising complementarity-determining regions (CDRs) 1-3 and having sequences set forth in FIG. 1B. In FIG. 1B the sequences for the CDRs for the NTD scFvs and the ECL2 scFvs are the non-grayed regions underneath the appropriate heading label. The sequence for each labeled CDR region in the alignment is denoted by a line directly above the corresponding sequences. For example, the sequence for CDRL1 in 13F-scFv is ILRSDFSVVTQRVY (SEQ ID NO:8), and the sequence for CDRH1 in 58C-scFv is TYDIY (SEQ ID NO:9).

An antibody in this disclosure can be a scFv directed to the N-terminal domain (NTD) of CCR2 comprising a heavy chain variable region (VH) comprising 3 complementarity determining regions (CDRs) having sequences set forth in FIG. 1, and a light chain variable region comprising 3 CDRs having sequences set forth in FIG. 1.

An antibody in this disclosure can be a scFv directed to the ECL domains 1, 2, or 3 of CCR2 comprising a heavy chain variable region (VH) comprising 3 complementarity determining regions (CDRs) and a light chain variable region (VL) comprising 3 CDRs with the sequences for the scFv that binds the ECL2 domain described in SEQ ID NO:6 or 7 and also FIG. 1.

In an embodiment, this disclosure provides an antibody, such as an scFv, referred to herein as 13F comprising a variable light chain (VL) and a variable heavy chain (VH), wherein the VL comprises CDRL1, denoted by the sequence ILRSDFSVVTQRVY (SEQ ID NO:8); CDRL2, denoted by the sequence NSDSDKRLGS (SEQ ID NO:22); and CDRL3, denoted by the sequence VIWHNSAVV (SEQ ID NO:23); and the VH comprises CDRH1, denoted by the sequence SYWIG (SEQ ID NO:24); CDRH2, denoted by the sequence IIYPGDSDTRYSPSFQG (SEQ ID NO:25); and CDRH3, denoted by the sequence RPQYYDILTGWHAG (SEQ ID NO:26), wherein the antibody is specific for the N-terminal domain of CCR2.

In an embodiment, the antibody, such as a scFv, comprises the sequence of SEQ ID NO:1, or a sequence that is at least 80, 85, 90, 95, 98 or 99% identical to SEQ ID NO:1, and is specific for the N-terminal domain of CCR2.

In an embodiment, the antibody, such as a scFv, comprises the sequence of SEQ ID NO:53, or a sequence that is at least 80, 85, 90, 95, 98 or 99% identical to SEQ ID NO:53, and is specific for the N-terminal domain of CCR2.

In an embodiment, this disclosure provides an antibody, such as an scFv referred to herein as 25B, comprising a variable light chain (VL) and a variable heavy chain (VH), wherein the VL comprises CDRL1, denoted by the sequence SGSSSNIGNNYVS (SEQ ID NO:27); CDRL2, denoted by the sequence GNNKRPS (SEQ ID NO:28); CDRL3, denoted by the sequence ATWDDSLSAVV (SEQ ID NO:29); and the VH comprises CDRH1, denoted by the sequence NFYIH (SEQ ID NO:30); CDRH2, denoted by the sequence IINPSDGRTTYAQKFQG (SEQ ID NO:31); and CDRH3, denoted by the sequence GGHYSNYFGQ (SEQ ID NO:32), and wherein the antibody is specific for the N-terminal domain of CCR2.

In an embodiment, the antibody, such as a scFv, comprises the sequence of SEQ ID NO:2, or a sequence that is at least 80, 85, 90, 95, 98 or 99% identical to SEQ ID NO:2, and is specific for the N-terminal domain of CCR2.

In an embodiment, the antibody, such as a scFv, comprises the sequence of SEQ ID NO:54, or a sequence that is at least 80, 85, 90, 95, 98 or 99% identical to SEQ ID NO:54, and is specific for the N-terminal domain of CCR2.

In an embodiment, this disclosure provides an antibody, such as an scFv referred to herein as 26B, comprising a variable light chain (VL) and a variable heavy chain (VH), wherein the VL comprises CDRL1, denoted by the sequence SGSSSNIGSNYVY (SEQ ID NO:33); CDRL2, denoted by the sequence RNNQRPS (SEQ ID NO:34); CDRL3, denoted by the sequence AAWDDSLNGVV (SEQ ID NO:35); and VH comprises CDRH1, denoted by the sequence NFYIH-1 (SEQ ID NO:30); CDRH2, denoted by the sequence IINPSDGRTTYAQKFQG (SEQ ID NO:31); and CDRH3, denoted by the sequence GGHYSNYFGQ (SEQ ID NO:32) and wherein the antibody is specific for the N-terminal domain of CCR2.

In an embodiment, the antibody, such as a scFv, comprises the sequence of SEQ ID NO:3, or a sequence that is at least 80, 85, 90, 95, 98 or 99% identical to SEQ ID NO:3, and is specific for the N-terminal domain of CCR2.

In an embodiment, the antibody, such as a scFv, comprises the sequence of SEQ ID NO:55, or a sequence that is at least 80, 85, 90, 95, 98 or 99% identical to SEQ ID NO:55, and is specific for the N-terminal domain of CCR2.

In an embodiment, this disclosure provides an antibody, such as an scFv referred to herein as 37B, comprising a variable light chain (VL) and a variable heavy chain (VH), wherein the VL comprises CDRL1, denoted by the sequence KASGYTFTSYYMH (SEQ ID NO:36); CDRL2, denoted by the sequence NPSGGST (SEQ ID NO:37); CDRL3, denoted by the sequence ARDGNWFDP (SEQ ID NO:38); and wherein CDRH1, denoted by the sequence SSYLA (SEQ ID NO:39); CDRH2, denoted by the sequence IYGASSRATGIPDRFSG (SEQ ID NO:40); and CDRH3, denoted by the sequence QYGSS (SEQ ID NO:41) and wherein the antibody is specific for the N-terminal domain of CCR2.

In an embodiment, the antibody, such as a scFv, comprises the sequence of SEQ ID NO:4, or a sequence that is at least 80, 85, 90, 95, 98 or 99% identical to SEQ ID NO:4, and is specific for the N-terminal domain of CCR2.

In an embodiment, the antibody, such as a scFv, comprises the sequence of SEQ ID NO:56, or a sequence that is at least 80, 85, 90, 95, 98 or 99% identical to SEQ ID NO:56, and is specific for the N-terminal domain of CCR2.

In an embodiment, this disclosure provides an antibody, such as an scFv referred to herein as 58C, comprising a variable light chain (VL) and a variable heavy chain (VH), wherein the VL comprises CDRL1, denoted by the sequence RASQSVSSSYLA (SEQ ID NO:42); CDRL2, denoted by the sequence GASSRAT (SEQ ID NO:43); CDRL3, denoted by the sequence QQYGSSLT (SEQ ID NO:44); and wherein VH comprises CDRH1, denoted by the sequence TYDIY (SEQ ID NO:9); CDRH2, denoted by the sequence WVNPDNGKTDYAQKFQG (SEQ ID NO:45); and CDRH3, denoted by the sequence ALTRWQQS (SEQ ID NO:46) and wherein the antibody is specific for the N-terminal domain of CCR2.

In an embodiment, the antibody, such as a scFv, comprises the sequence of SEQ ID NO:5, or a sequence that is at least 80, 85, 90, 95, 98 or 99% identical to SEQ ID NO:5, and is specific for the N-terminal domain of CCR2.

In an embodiment, the antibody, such as a scFv, comprises the sequence of SEQ ID NO:57, or a sequence that is at least 80, 85, 90, 95, 98 or 99% identical to SEQ ID NO:57, and is specific for the N-terminal domain of CCR2.

In an embodiment, this disclosure provides an antibody, such as an scFv referred to herein as 4h, comprising a variable light chain (VL) and a variable heavy chain (VH), wherein the VL comprises CDRL1, denoted by the sequence SGSSSNIGSHTVN (SEQ ID NO:47); CDRL2, denoted by the sequence RNNQRPS (SEQ ID NO:34); CDRL3, denoted by the sequence AAWDDSLSGVV (SEQ ID NO:48); and wherein CDRH1, denoted by the sequence NFYIH (SEQ ID NO:30); CDRH2, denoted by the sequence IINPSDGRTTYAQKFQG (SEQ ID NO:31); and CDRH3, denoted by the sequence GGHYSNYFGQPST (SEQ ID NO:49), and wherein the antibody is specific for the extracellular loop 2 domain of CCR2.

In an embodiment, the antibody, such as a scFv, comprises the sequence of SEQ ID NO:6, or a sequence that is at least 80, 85, 90, 95, 98 or 99% identical to SEQ ID NO:6, and is specific for the extracellular loop 2 domain of CCR2.

In an embodiment, this disclosure provides an antibody, such as an scFv referred to herein as 11b, comprising a variable light chain (VL) and a variable heavy chain (VH), wherein the VL comprises CDRL1, denoted by the sequence SGSSSNIGSNYVY (SEQ ID NO:33); CDRL2, denoted by the sequence RNNQRPS (SEQ ID NO:34); CDRL3, denoted by the sequence AAWDDTLIGPV (SEQ ID NO:50); and wherein the VH comprises CDRH1, denoted by the sequence DAWMN (SEQ ID NO:51); CDRH2, denoted by the sequence RIRSKAGGGTTDSAAPVKD (SEQ ID NO:52); and CDRH3, denoted by the sequence EGY, and wherein the antibody is specific for the extracellular loop 2 domain of CCR2.

In an embodiment, the antibody, such as a scFv, comprises the sequence of SEQ ID NO:7, or a sequence that is at least 80, 85, 90, 95, 98 or 99% identical to SEQ ID NO:7, and is specific for the extracellular loop 2 domain of CCR2.

The terms "antibody" as used herein can encompass whole antibody molecules, full-length immunoglobulin molecules, such as naturally occurring full-length immunoglobulin molecules or full-length immunoglobulin molecules formed by immunoglobulin gene fragment recombinatorial processes, as well as antibody fragments including scFvs. Antibody fragments can be fragments comprising at least one antibody-antigen binding site. Antibody fragments can, for example, exhibit specific binding to CCR2 or fragments thereof.

The term "antibody" can include e.g. monoclonal, polyclonal, multispecific (for example bispecific), recombinant, human, chimeric and humanized antibodies. The term "antibody" can also encompass recombinantly expressed antigen binding proteins and antigen binding synthetic peptides. Further, the term "antibody" can encompass minibodies, and diabodies, all of which preferably exhibit specific binding to CCR2 or a fragment thereof, especially human CCR2. The term "antibody", as used herein, can also encompass antibodies produced in vivo, as well as those produced in vitro, such as, for example, by a bacterial expression system or a mammalian hybridoma cell line.

An antibody of the present disclosure may be modified by, for example, acetylation, formylation, amidation, phosphorylation, or polyethylene glycolation (PEGylation), as well as glycosylation. The term "an antibody" as used herein is intended to cover all antibodies disclosed herein. For example, the term "an antibody" can refer to monoclonal, polyclonal, scFv, chimeric, human, or humanized antibodies, or antigen (i.e., CCR2) binding fragments thereof.

In an embodiment, anti-CCR2 scFvs are PEGylated to increase half-life and bioavailability. Various types of PEG molecules can be added to the scFvs, including but not limited to PEG(5K), PEG(10K), PEG(20K), and PEG(40K). The scFvs can be modified by the addition of a cysteine, lysine or serine amino acid to facilitate PEGylation. This modification can occur at, but is not limited to, the C-terminus of the scFv.

The antibodies of the disclosure may be whole immunoglobulin molecules such as polyclonal or monoclonal antibodies or may be antigen-binding fragments thereof, including but not limited to, Fab, F(ab'), F(ab')2, Fv, dAb, Fd, CDR fragments, single-chain variable fragment antibodies (scFv), bivalent single-chain antibodies, single-chain phage antibodies, diabodies, nanobodies and the like. The fragments of the antibodies may be produced synthetically or by enzymatic or chemical cleavage of intact immunoglobulins or may be genetically engineered by recombinant DNA techniques. These techniques are well known in the art.

In one embodiment, this disclosure provides isolated antibodies. By the term "isolated" it is meant that the antibody or the fragment thereof, is separated and/or recovered from its natural environment. The isolation of the antibody from its natural environment can be such that the antibody can be used without interference from other active agents (such as other proteins) that normally are present in its natural environment.

"Fv" is the minimum antibody fragment that contains a complete antigen-recognition and -binding site and single-chain Fv also abbreviated as "sFv" or "scFv" are antibody fragments that comprise the VH and VL antibody domains connected into a single polypeptide chain. The term "diabodies" refers to small antibody fragments prepared by constructing sFv fragments with short linkers between the VH and VL domains such that inter-chain but not intra-chain pairing of the V domains is achieved, resulting in a bivalent fragment, i.e., fragment having two antigen-binding sites. A single domain antibody (sdAb) is an antibody fragment which has a single monomeric variable antibody domain. ScAbs can be made from heavy-chain antibodies found in camelids. An antibody fragment can be a single variable region or a peptide consisting of or comprising a single CDR. A single-chain antibody has a heavy chain variable domain and a light chain variable domain linearly linked to each other via a linker. A polynucleotide (such as DNA) encoding the single-chain antibody can be produced by binding a polynucleotide encoding the heavy chain variable domain, a polynucleotide encoding the linker (typically 10-20 nucleotides), and a polynucleotide encoding the light chain variable domain, with the heavy chain variable domain and the light chain variable domain being both derived from a human antibody.

As an example, this disclosure provides scFv antibodies, which can be isolated scFv antibodies, which specifically bind to CCR2, which can be human CCR2. As an example, scFvs designated 58C-scFv and 11b-scFv are provided. Specifically, 58C-scFv binds to the NTD of CCR2 whereas 11b-scFv binds to the ECL2 domain of CCR2.

The present disclosure also provides isolated nucleotide sequences encoding all or portions of the amino acid sequences disclosed herein. For example, the present disclosure provides an isolated nucleic acid molecule comprising the sequences of the CDRs, such as CDRL1, CDRL2, CDRL3, CDRH1, CDRH2, CDRH3 for the various scFvs disclosed herein. In an embodiment, the present disclosure also provides isolated nucleic acid molecules comprising or consisting of the sequence encoding one or more CDRs that recognize a NTD or ECL2 domain of CCR2. The disclosure also provides cells comprising an expression vector or other polynucleotide sequence encoding the antibodies provided herein (including scFvs). Nucleotide sequences encoding the scFvs can be expressed using any suitable expression vector, many of which are known in the art and/or are commercially available. A vector generally includes nucleic acid sequences, such as origin or replication that enables it to replicate in a host cell. A vector can also include selectable marker genes.

This disclosure provides compositions comprising anti-CCR2 scFvs loaded onto liposomes. Standard approaches for ligand attachment to aqueous liposome nanoparticles make use of maleimides, succinimidyl esters and carbodiimide-activated carboxylic acids. These can covalently react with amine and thiol groups of polypeptides. The use of maleimide-lipids has been explored extensively for anti-body-conjugated liposomes. Conjugation yields may reach as high as 90% from an overnight reaction, but subsequent quenching of free maleimide groups and additional purification is required. Proteins may require a preparative step of thiolation and purification prior to conjugation. Antibody orientation is a major factor influencing the conjugated antibody target binding efficacy, but these approaches result in numerous antibody labeling sites and indiscriminate orientations. Biorthogonal synthetic strategies such as the click reaction have recently been applied to pre-formed liposomes, however these require the use exogenous catalysts and unconventional amino acids.

The liposomes in the present disclosure may be spherical or non-spherical. The size of the liposomes can be from 50 to 1000 nm or more. In one embodiment, the liposomes have a size (e.g., a longest dimension such as, for example, a diameter) of 50 to 1000 nm, including all integer nm values and ranges therebetween. For example, the size may be from 50 to 200 nm or from 20 to 1000 nm. If the liposomes are not spherical, the longest dimension can be from 50 to 1000 nm. These dimensions can be achieved while preserving the nanostructure width of the monolayer or the bilayer. The liposomes can carry cargo in the aqueous compartment. The cargo, or part thereof, can also, or alternatively, be incorporated in the monolayer or the bilayer.

In one embodiment, this disclosure provides liposomes comprising: a monolayer or a bilayer, wherein the monolayer or bilayer comprises anti-CCR2 scFv lipid conjugates, optionally phospholipids that are not conjugated to anti-CCR2 scFvs, and a polyhistidine-tagged presentation molecule, wherein the polyhistidine tag is linked to the scFv in the hydrophobic portion of the monolayer or the bilayer and one or more histidines of the polyhistidine tag are coordinated to nickel atoms attached to the lipids in the lipid monolayer or bilayer of the liposomes.

In an embodiment, anti-CCR2 scFvs are His-tagged and loaded on to liposomes containing lipids in the monolayer or bilayer that are bound with nickel as described in Example 1. Additionally scFvs can be conjugated to maleimide lipids for further downstream applications as described in Example 2 of this disclosure.

Reactivity of antibodies toward specific antigens, such as CCR2, can be measured by routine methods such as, for example, ELISA. Reactivity is an indication of the binding affinity. Binding affinity can also be measured by antigen/antibody dissociation rates or competition radioimmunoassays and the like. Specific binding of an antibody to an antigen means it binds the antigen with high affinity and does not specifically bind to unrelated antigens.

This disclosure provides compositions and methods for inhibiting cellular migration by blocking binding of CCL2 to CCR2. Monocytes and macrophages express CCR2 and migrate in response to CCL2 serving as a chemoattractant. In an example, the anti-CCR2 scFvs described in this disclosure specifically block macrophage migration toward a CCL2 chemotaxis gradient. In another example, the anti-CCR2 scFvs described in this disclosure block cancer cell migration, such as breast cancer cell migration.

This disclosure provides methods and compositions for inhibiting macrophage polarization. In an example, the scFvs described in this disclosure that target the N-terminal domain and ECL2 significantly promotes M1 macrophage polarization while inhibiting M2 macrophage polarization. This type of response is desirable in an anti-cancer setting as M1 macrophages suppress tumor growth whereas M2 macrophages promote tumor growth.

In an embodiment, this disclosure provides a method for inhibiting cellular migration or inhibiting macrophage polarization by blocking binding of CCL2 to CCR2 comprising contacting the cells with an effective amount of one or more anti-CCR2 scFvs. The antibody may be an antibody directed to the N-terminal domain of CCR2 or to ECL1, ECL2 or ECL3 or combinations thereof. Examples of scFvs directed against the N-terminal domain of CCR2 include 13F, 25B, 26B, 37B and 58C, and examples of scFvs directed against the ECL2 include 4h and 11b. In an embodiment, the method comprises contacting the cell with a scFv directed to the N-terminal domain of CCR2 and a scFv directed against the ECL2 of CCR2. Any of the scFvs specific for the N-terminal domain including 13F, 25B, 26B, 37B and 58C, and any of the scFvs specific for ECL2 of CCR2, including 4h and 11b may be used. In an embodiment, a combination of 58C and 4h is used.

When reference is made to any of the scFvs in this disclosure, then it includes the shortened version of the scFvs also.

In an aspect, the present disclosure also provides a pharmaceutical composition comprising a pharmaceutically acceptable carrier and one or more scFvs of the present disclosure. Examples of carriers include solutions, suspensions, emulsions, solid injectable compositions that are dissolved or suspended in a solvent before use, and the like. The injections may be prepared by dissolving, suspending or emulsifying one or more of the active ingredients in a diluent. Examples of diluents, include, but are not limited to distilled water for injection, physiological saline, vegetable oil, alcohol, dimethyl sulfoxide, and a combination thereof. Further, the injections may contain stabilizers, solubilizers, suspending agents, emulsifiers, soothing agents, buffers, preservatives, etc. The injections may be sterilized in the final formulation step or prepared by sterile procedure. The composition of the disclosure may also be formulated into a sterile solid preparation, for example, by freeze-drying, and can be used after sterilized or dissolved in sterile injectable water or other sterile diluent(s) immediately before use. Additional examples of pharmaceutically include, but are not limited to, sugars, such as lactose, glucose, and sucrose; starches, such as corn starch and potato starch; cellulose, including sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as propylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Additional non-limiting examples of pharmaceutically acceptable carriers can be found in: *Remington: The Science and Practice of Pharmacy* (2005) 21*st Edition*, Philadelphia, PA Lippincott Williams & Wilkins.

The scFvs of the present disclosure, or a composition comprising one or more scFvs may be used to block CCR2 from binding CCL2. The activity may be altered in vitro or in vivo. As such, the present compositions may be administered to an individual who is exhibiting abnormal CCL2/CCR2 binding. Examples of conditions in which the present scFvs and compositions can be used is any condition in which CCL2/CCR2 binding is abnormal. Such conditions can include, but are not limited to, cancer and immune disorders. In an embodiment the method comprises administering to an individual in need of treatment (such as an individual who is exhibiting abnormal CCL2/CCR2 binding), one or more antibodies specific for the N-terminus of CCR2 and one or more antibodies specific for the ECL2.

In an aspect, the disclosure provides a method for treating an individual having or suspected of having cancer whose tumor sample has CCR2 expressing cells and/or CCL2 secreting cells. A sample from the individual's tumor (e.g., biopsy and/or blood sample) may be used to measure CCR2 and/or CCL2 levels. If the tumor is found to have elevated CCR2 and/or CCL2 levels, a suitable amount of the anti-CCR2 scFv therapy can be administered to the individual using a suitable route (e.g., intratumoral, intravenous, intradermal injection). The treatment may be carried out without first sampling CCR2 and/or CCL2 levels. In an embodiment, the individual may be administered one or more anti-CCR2 scFvs or a composition comprising one or more anti-CCR2 scFvs comprising or consisting of the sequences of SEQ ID NO:1-7.

The disclosure provides a method for treating tumors, such as tumors that comprise CCR2-expressing cells, for example tumor-associated macrophages (TAMs). Such tumors may be referred to herein as "CCR2-expressing tumors". The term "treatment" refers to reduction in one or more symptoms or features associated with the presence of the particular condition being treated. Treatment does not necessarily mean complete remission, nor does it preclude recurrence or relapses. For example, the present disclosure provides a method for reducing the size of a tumor or arresting the growth of a tumor or reducing the rate of growth of a tumor (such as a tumor comprising CCR2-expressing cells and/or CCL2 secreting cells) or reducing any other symptom that is associated with an individual being afflicted with the tumor—all of which are considered as "treatment"—comprising administering to an individual in need of treatment, a therapeutically effective amount of a composition comprising antibodies, or fragments thereof as described herein. In one embodiment, the method of treatment is a method of passive immunization.

In an embodiment, this disclosure provides a method of reducing the growth of a tumor in an individual, such as a tumor comprising CCR2 expressing cells, comprising administering to the individual a therapeutically effective amount of one or more anti-CCR2 scFvs. The antibody may be an antibody directed to the N-terminal domain of CCR2 or to ECL1, ECL2 or ECL3 or combinations thereof. Examples of scFvs directed against the N-terminal domain of CCR2 include 13F, 25B, 26B, 37B and 58C, and examples of scFvs directed against the ECL2 include 4h and 11b. In an embodiment, the method comprises administering to the individual an scFv directed to the N-terminal domain of CCR2 and an antibody directed against the ECL2 of CCR2. Any of the scFvs specific for the N-terminal domain including 13F, 25B, 26B, 37B and 58C, and any of the scFvs specific for ECL2 of CCR2, including 4h and 11b may be used. In an embodiment the method comprises administering to an individual in need of treatment (such as an individual who has been diagnosed with a tumor), one or more antibodies specific against the N-terminus of CCR2 and one or more antibodies specific against the ECL2. In an embodiment the method comprises administering to an individual in need of treatment, one or more antibodies selected from 13F, 25B, 26B, 37B and 58C, and one or more antibodies selected from 4h and 11b. In an embodiment the method comprises administering to an individual in need of treatment, scFvs 58C and 4h. The administration of the antibodies may result in one or more of the following: inhibition of tumor growth, reduction of TAMs, reduction of MDSCs, reduction of M2-macrophages, reduction of Foxp3+/CD4+ Tregs, increase in M1-macrophages, increase in CD8+ T cells, and increase in CD4+ T cells.

Examples of tumors that can be treated by the present anti-CCR2 scFvs or compositions comprising anti-CCR2 scFvs include, but are not limited to, breast adenocarcinoma, glioma, glioblastoma, medulloblastoma, multiple myeloma, melanoma, meningioma, ovarian carcinoma, prostate carcinoma, leukemia, lymphoma, colon carcinoma, pancreatic cancer, hepatic cancer, kidney cancer, sarcoma and the like. The tumor may be metastatic.

In an embodiment, the present disclosure provides a method of reducing metastases of tumor such as a tumor comprising CCR2 expressing cells, the method comprising administering to the individual a therapeutically effective amount of one or more anti-CCR2 scFvs. The antibody may be an antibody directed to the N-terminal domain of CCR2 or to ECL1, ECL2 or ECL3 or combinations thereof. Examples of scFvs directed against the N-terminal domain of CCR2 include 13F, 25B, 26B, 37B and 58C, and examples of scFvs directed against the ECL2 include 4h and 11b. In an embodiment the method comprises administering to an individual in need of treatment, scFvs 58C and 4h. In an embodiment the method or inhibiting metastases comprises administering to an individual in need of treatment (such as an individual who has been diagnosed with a tumor), one or more antibodies specific against the N-terminus of CCR2 and one or more antibodies specific against the ECL2. In an embodiment the method or inhibiting metastases comprises administering to an individual in need of treatment (such as an individual who has been diagnosed with a tumor), one or more antibodies selected from 13F, 25B, 26B, 37B and 58C, and one or more antibodies selected from 4h and 11b.

In one aspect, the disclosure provides a method of passive immunization comprising administering to an individual in need of treatment, a therapeutically effective amount of one or more of the scFvs antibodies or a composition comprising one or more scFv antibodies and which antibodies have been isolated from the subject (human or non-human) they were raised in or obtained from a hybridoma supernatant, bacterial expression system, or may be engineered antibodies using sequences from the isolated antibodies.

The following examples are meant to illustrate, and are not intended to be limiting.

Example 1

This example describes that CCR2 inhibition and the strategy of multi-valent engagement of CCR2 modulates macrophage polarization.

Materials and Methods

Materials

All chemicals and solvents were purchased from Thermo Fisher Scientific (Waltham, MA), unless otherwise stated.

Phage Library Screening Against CCR2 N-Terminal Domain

Biotinylated N-terminal CCR2 domain was captured on magnetic streptavidin coated beads and four rounds of affinity selections were performed as previously described.[24] The selection was performed at room temperature using a phage display library that was constructed from peripheral human blood lymphocytes and that expresses single-chain fragments of antibodies. To identify CCR2 N-terminal domain binders, single bacterial colonies were picked after the fourth round of selection for phage amplification followed by a phage enzyme-linked immunosorbent assay (ELISA). Clones that yielded a signal above background were sequenced and further analyzed with regard to binding affinity.

Protein Expression and Purification

The 58C-scFv cloned into the pET21a vector (Novagen, Burlington, MA) was expressed in BL-21 (DE3) cells (Lucigen, Middleton, WI). Bacterial cultures were grown overnight at 37° C. in 2×YT medium, ampicillin, and 1% glucose. A 1 L 2×YT culture was inoculated with 1% of the overnight culture and grown to an $OD_{600}$ of ~0.6. Protein expression was induced with 0.2 mM isopropyl β-D-1-thiogalactopyranoside (IPTG). After an overnight incubation at 24° C., the cells were harvested 18 h post-induction by centrifugation. The cell pellet was resuspended in lysis buffer containing 50 mM Tris, 100 mM KCl, and 2 M urea, pH 8.5. The cell suspension was centrifuged at 9,000×g for 5 minutes at 4° C. and the pellet collected and washed three times with lysis buffer. After the final wash, the pellet was re-suspended in solubilization buffer (50 mM Tris, 100 mM KCl, 5 M guanidine, and 10 mM β-mercaptoethanol, pH 8.5). The solution was incubated at 37° C. for 1 h and then centrifuged at 9,000×g for 10 min at 4° C. The supernatant was collected and diluted 1:10 into refolding buffer containing 50 mM Tris, 500 mM NaCl, 400 mM sucrose, 3 mM reduced glutathione, 0.3 mM oxidized glutathione, 0.5% Triton X-100, 10% glycerol, and 10 mM imidazole, pH 8.5. The solution was stirred at 200 rpm at 4° C. for 24 h, after which TALON cobalt beads (Clontech, Mountain View, CA) were equilibrated with refolding buffer and added to the solution. The beads were incubated with the solution and the protein was isolated by immobilized metal affinity chromatography (IMAC).

Enzyme-Linked Immunosorbent Assay (ELISA)

Nunc MaxiSorp 96-well plates were coated with NeutrAvidin at 5 μg/mL and incubated overnight at 4° C. The plate was thoroughly washed with 0.1% PBS-Tween (PBST), and 5 μg/mL biotinylated N-terminal domain CCR2 peptide (MEDNNMLPQFIHGILSTSHSLFTRSIQELDEGAT-TPYDYDDGEPC (SEQ ID NO:58); ABclonal, Woburn, MA) added and incubated for 1 h at room temperature. The wells were washed with 0.1% PBST and then blocked with casein blocking buffer for 1 h at room temperature. The wells were washed with 0.1% PBST followed by incubation of serially diluted scFv for 1 h at room temperature before being washed five times with 0.1% PBST. Washes were followed by the addition of 100 uL of the respective horseradish peroxidase (HRP)-linked monoclonal antibody (mAb) for 1 h at room temperature with rocking. An anti-M13 mAb was used to detect phages (#27-9421-01, GE healthcare, Chicago, IL) and an anti-flag mAb was used to detect scFv (#A8592, Sigma Aldrich, St. Louis, MO). The wells were washed with 0.1% PBST followed by the addition of TMB-ELISA substrate. After 10 min incubation, 2 M $H_2SO_4$ was added to stop the reaction. The absorbance was measured at 450 nm with a FilterMax F3 & F5 multi-mode microplate reader (Molecular Devices, Sunnyvale, CA). A 1:1 binding ratio Hill model was used to fit the binding interaction data.

Cell Binding Analysis by Flow Cytometry

Cells were detached with 5 mM EDTA and re-suspended in PBS to a concentration of 50,000 cells per 300 μL. Cells were plated in a 48-well plate and incubated for 30 min at 4° C. After removing the PBS solution, the cells were incubated with various dilutions of DyLight 650 NHS Ester labeled 58C-scFv for 1 h at 4° C. Cells were washed three times with 5% BSA, detached with EDTA, and analyzed in the APC channel of a MACSQuant Analyzer 10 flow cytometer (Miltenyi Biotec, Bergisch Gladbach, Germany).

Transwell Migration Assay

Cells were serum starved for 24 h before being detached with 5 mM EDTA in PBS and re-suspended in transwell medium (DMEM without phenol red, 25 mM HEPES, and 0.1% BSA) at a concentration of $70×10^4$ cells per 100 μL. Cells were incubated with various concentrations of scFv for 30 min at 4° C. and then added to the apical chamber of either a 5 μm (RAW 264.7) or 8 μm (MDA-MB-231) pore transwell plate (Milipore Sigma, Burlington, MA). The basolateral compartment contained 25 nM of CCL2 in serum-free medium to induce chemotaxis. Cells were incubated at 37° C. with 5% $CO_2$ for either 4 h (RAW 264.7) or 21 h (MDA-MB-231). After incubation, the cells in the apical chamber were removed and the wells were placed in a new feeder tray containing pre-warmed cell detachment solution. Wells were incubated with cell detachment buffer for 30 min at 37° C. with occasional rocking to detach migrated cells. Then, lysis buffer and dye solution were added to the detachment solution containing the migrated cells. The solution was incubated for 15 min and fluorescence measured on a SpectraMax microplate reader (Molecular Devices) with an excitation/emission of 480/520.

Macrophage Polarization

RAW 264.7 mouse macrophages were incubated with either LPS (100 ng/mL), IL-4 (20 ng/mL; PeproTech, Rocky Hill, NJ), or 58C-scFv (1 µM) for 24 h. For the multivalency studies, RAW 264.7 mouse macrophages were first incubated with IL-4 (20 ng/mL) for 24 h to stimulate an M2 phenotype. Following the 24 h incubation, fresh media with 58C-scFv (89 nM) was added to the cells and incubated for an additional 24 h. Total RNA was isolated with QIAzol lysis reagent (Qiagen, Germany) and total cDNA was generated using the New England Biolabs first stand synthesis kit (Ipswich, MA). RNA expression was detected by reverse transcription (RT)-PCR performed with the SYBR Green PCR kit (Qiagen). For each sample, the ΔΔCt value was calculated. Experiments were performed in triplicate. The primers were: β-actin (forward: 5'-ccctgtatgcctctggtc-3' (SEQ ID NO:10), reverse: 5'-gtcttttacggatgtcaacg-3'(SEQ ID NO:11)), iNOS (forward: 5'-tttgcttccatgctaatgcgaaag-3' (SEQ ID NO:12), reverse: 5'-gctctgttgaggtctaaaggctccg-3' (SEQ ID NO:13)), IL-6 (forward: 5'-tgggaaatcgtggaaatgag-3'(SEQ ID NO:14), reverse: 5'-ctgaaggactctggctttgtc-3'(SEQ ID NO:15)), ARG-1 (forward: 5'-cagaagaatggaagagtcag-3' (SEQ ID NO:16), reverse: 5'-cagatatgcagggagtcacc-3'(SEQ ID NO:17)), MGL2 (forward: 5'-agcgggaagagaaaaaccag-3' (SEQ ID NO:18), reverse: 5'-agatgaccaccagtagcaggag-3' (SEQ ID NO:19)).

Liposome Preparation

All lipids were purchased from Avanti Polar Lipids (Alabaster, AL). Lipids dissolved in chloroform were mixed, dried down to a thin film, and placed under high vacuum for 2 h. Lipid mixtures included DSPC:DGS-NTA(Ni):Chol (50:30:20), DSPC:DGS-NTA(Ni):Chol (70:10:20), and DSPC:DGS-NTA(Ni):Chol (75:5:20). The films were rehydrated with 1 mL PBS at 60° C. and vortexed. The liposomes were sonicated at 60° C. for 10 min. The liposomes were extruded through a 100 nm polycarbonate membranes (Avanti Polar Lipids) at 60° C. Liposomes were incubated with a 660:1 molar ratio of DGS-NTA(Ni) lipid to His-tagged 58C-scFv to ensure maximum binding at 4° C. overnight. A sepharose CL-6B size exclusion column was used to remove free, unbound 58C-scFv. Fluorescently labeled 58C-scFv was used to determine the amount of scFv bound to liposomes. The low valency formulation had approximately 14 58C-scFvs per liposome, the medium valency formulation had approximately 28 58C-scFvs per liposome, and the high valency formulation had approximately 84 58C-scFvs per liposome (Table 1). This table provides the number of scFv molecules per liposome. Since a His-tag can bind to several NTA-lipids, we used a 660:1 molar ratio of NTA lipid to 58C-scFv to ensure maximal binding of the targeting ligand. The number of lipids per liposomes was calculated as previously described and was estimated to be ~186,000 lipids per 150 nm liposome. The number of lipids per liposome was calculated using the following equation:

$$N = 4\pi \frac{\left(\frac{d}{2}\right)^2 + \left(\frac{d}{2} - l\right)^2}{A_{lipid}}$$

Where N is the number of lipids, d is the diameter of the liposome, l is the thickness of the bilayer (~5 nm) and $A_{lipid}$ is the head group area of a phosphatidylcholine lipid (~0.71 $nm^2$). This results in ~14, 28, and 84 58C-scFv molecules per liposome for the low, medium, and high valency, respectively.

TABLE 1

| Valency | mol % of NTA lipid | mol % of scFv | # of scFv molecules per mol lipid | # of liposomes per mol lipid | scfv per liposome: |
|---|---|---|---|---|---|
| Low | 5 | 0.0076 | 4.58E+19 | 3.23E+18 | 14 |
| Med | 10 | 0.015 | 9.03E+19 | 3.23E+18 | 28 |
| High | 30 | 0.045 | 2.71E+20 | 3.23E+18 | 84 |

Data Analysis and Statistics

Comparisons between groups were analyzed using one-way ANOVA with post-hoc Dunnett (*p<0.05, p<0.01, *p<0.001). All statistical analyses were performed in Prism 7 (GraphPad Software, La Jolla, CA). All experiments were performed in triplicate. The error bars represent standard deviations (SD).

Results

Expression and Characterization of 58C-scFv Against the N-Terminal Domain of CCR2

A phage library expressing human scFvs with $2\times10^9$ diversity was panned against the flexible N-terminal domain of CCR2 (FIG. 1A). Binders with an absorbance above background were selected for further characterization. When sequenced, the top five binders all had unique complementarity determining regions (CDRs) (FIG. 1B). Phage clone 58C had the highest affinity by phage ELISA and was therefore chosen for subsequent studies (FIGS. 2A&B). The 58C-scFv protein bound to the CCR2 N-terminus with high affinity ($K_D$=59.8 nM; FIG. 2C) and was recombinantly expressed with a yield of 1 mg/L and a molecular weight of approximately 33 kDa (FIG. 2D).

Figure 8:
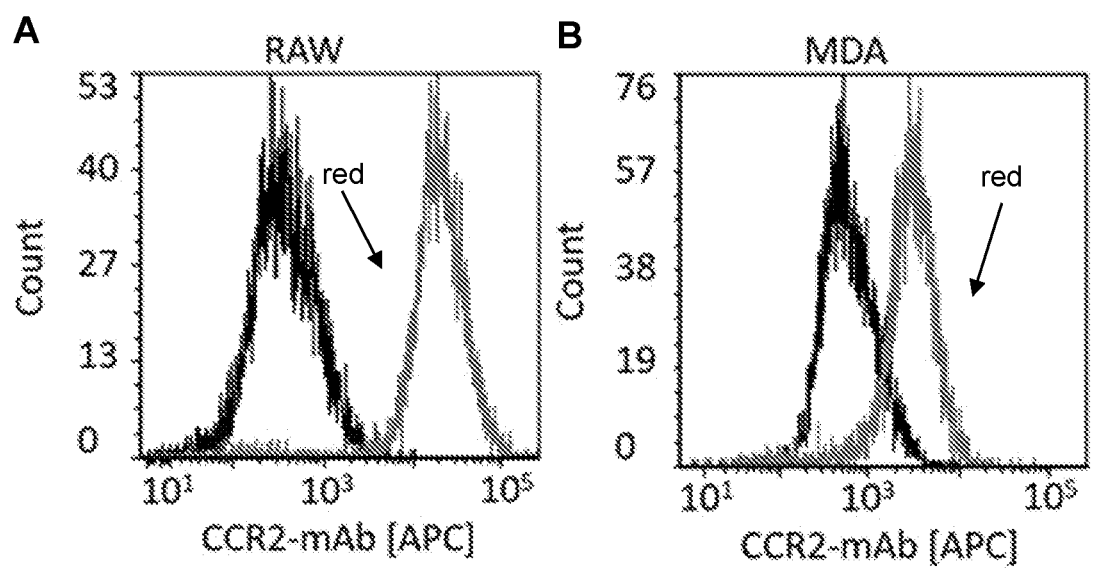
FIG. 8. Commercially available anti-mouse APC-conjugated CCR2-antibody (#FAB5538A, R&D, Minneapolis, MN) was used to detect CCR2 expression in (A) RAW 264.7 murine macrophages (red line). Commercially available anti-human APC-conjugated CCR2-antibody (#357208, BioLegend, San Diego, CA) was used to detect CRR2 expression in (B) MDA-MB-231 cells (red line). Binding of the APC-labeled antibodies to the respective cells were analyzed by flow cytometry.

We next assessed if 58C-scFv also bound to cellular CCR2 using RAW 264.7 mouse macrophages and MDA-MB-231 human breast cancer cells, both of which express CCR2 (FIGS. 8A and 8B). 58C-scFv was fluorescently labeled and bound with concentration dependence to murine macrophages (FIG. 2E). Although a CCR2 peptide corresponding to the murine N-terminal domain was used for affinity selection, the human and mouse CCR2 N-terminal domains have 80% sequence similarity. Therefore, we were interested if the 58C-scFv cross-reacted and bound human CCR2. Indeed, 58C-scFv bound with concentration dependence to human MDA-MB-231 breast cancer cells (FIG. 2F). Human embryonic kidney (HEK) cells that are CCR2-negative served as a control. 58C-scFv demonstrated significantly higher binding to CCR2 expressing cells than CCR2-negative HEK cells (FIG. 2G).

The Effect of 58C-scFv on Macrophage and Breast Cancer Cell Migration

Figure 9:
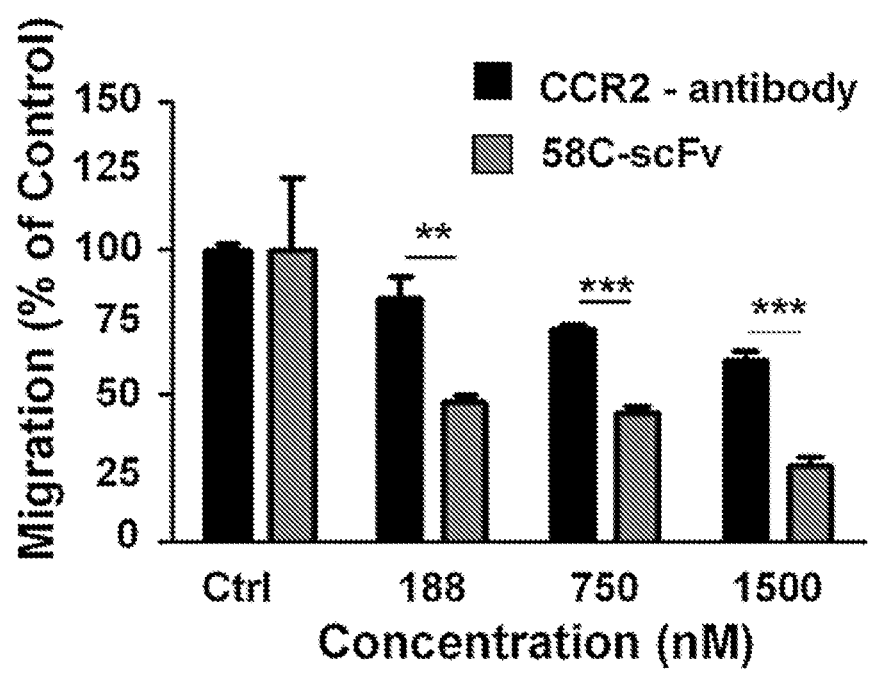
FIG. 9. Effect of monomeric 58C-scFv and a commercially available CCR2-targeted antibody (Clone #475301, R&D, Minneapolis, MN) on cellular migration of RAW 264.7 murine macrophages. Data are represented as mean±sd (n=3), *p<0.05, p<0.01, *p<0.001 with one-way ANOVA followed by Dunnett's post-test.

The effect of CCR2-targeting 58C-scFv on macrophage and breast cancer cell migration was tested. Monocytes, macrophages, and breast cancer cells express CCR2 and migrate along the CCR2/CCL2 chemotaxis gradient. RAW 267.4 and MDA-MB-231 cells were incubated with increasing concentrations of 58C-scFv, with CCL2 serving as the chemoattractant. 58C-scFv inhibited migration of breast cancer and macrophage cells by approximately 75% at the highest concentration tested (FIG. 3), suggesting that this scFv is specific for the CCL2/CCR2 pathway and acts as a CCR2 antagonist. 58C-scFv demonstrated ~40-60% higher inhibition of macrophage migration than a commercially available CCR2-targeted antibody (FIG. 9).

Figure 4:
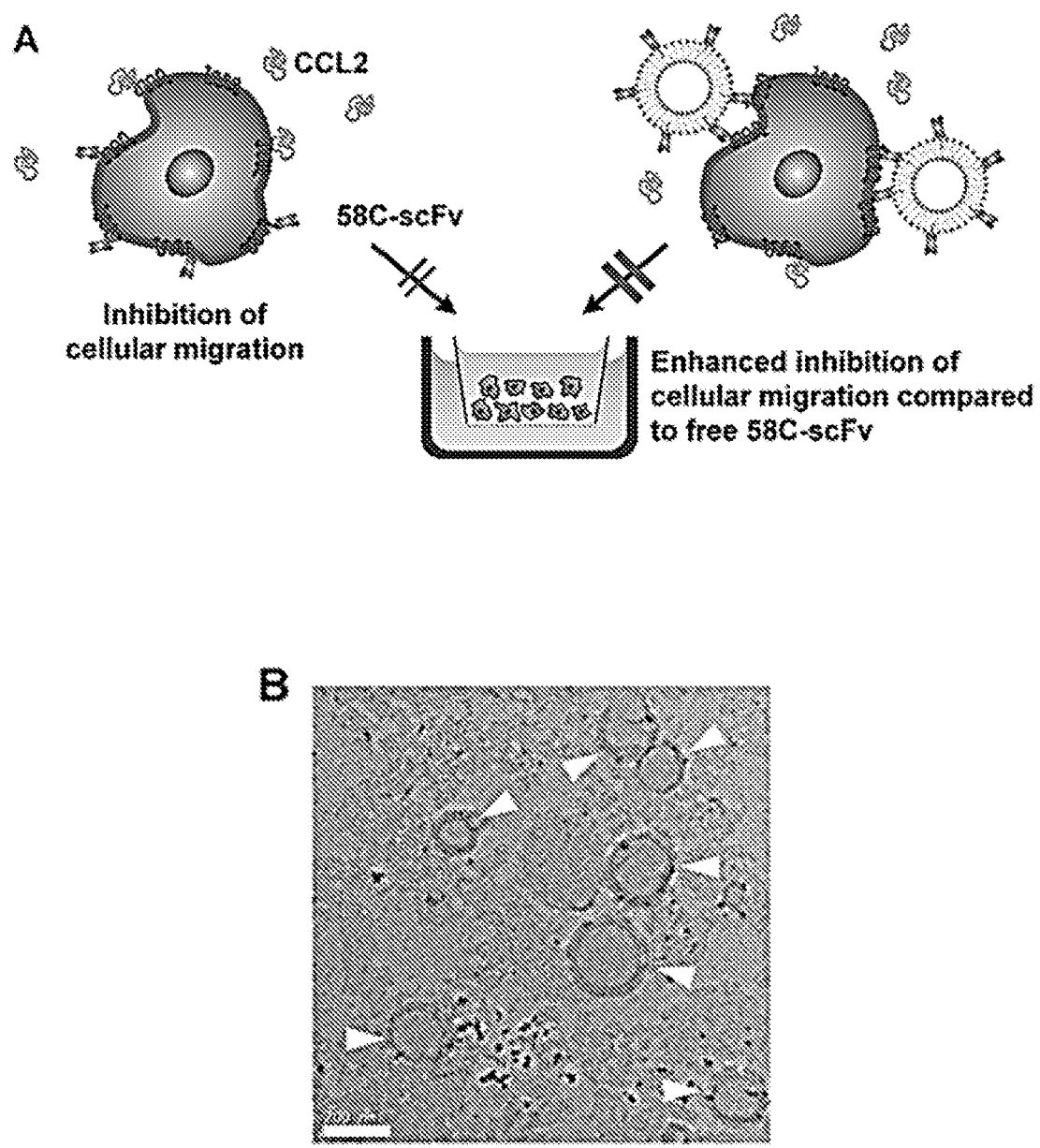
FIG. 4. Effect of free, monomeric 58C-scFv and multivalent 58C-scFv on cellular migration. (A) Schematic illustrating the effect of 58C-scFv and liposomal multivalent display of 58C-scFv on cellular migration. (B) TEM image of liposomes surface-decorated with 58C-scFv (high degree of valency), scale bar: 200 nm. Transwell migration assay performed with (C) RAW 264.7 murine macrophages (D) and MDA-MB-231 breast cancer cells. Experiments were performed in triplicate at 88.9 nM. Data are represented as mean±sd, *p<0.05, p<0.01, *p<0.001 with one-way ANOVA followed by Dunnett's post-test.
Figure 4:
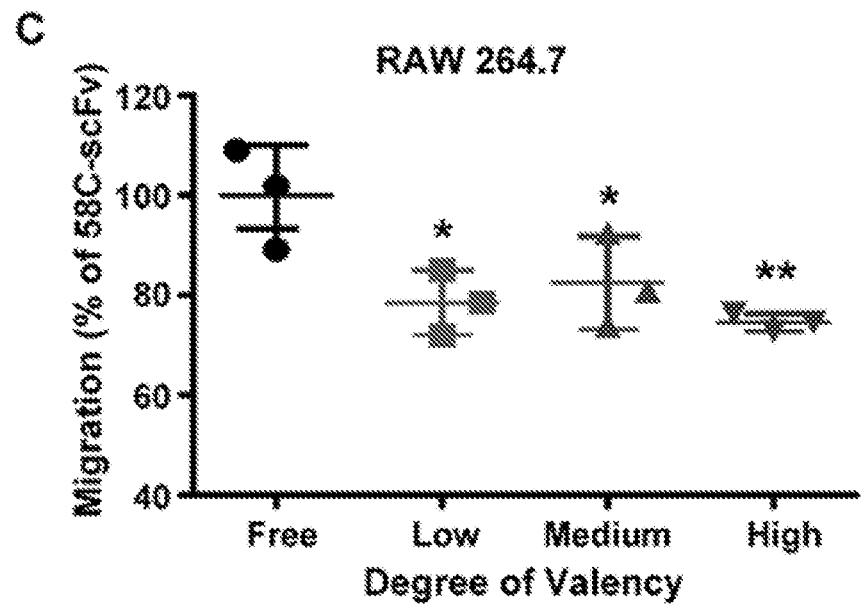
Figure 4:
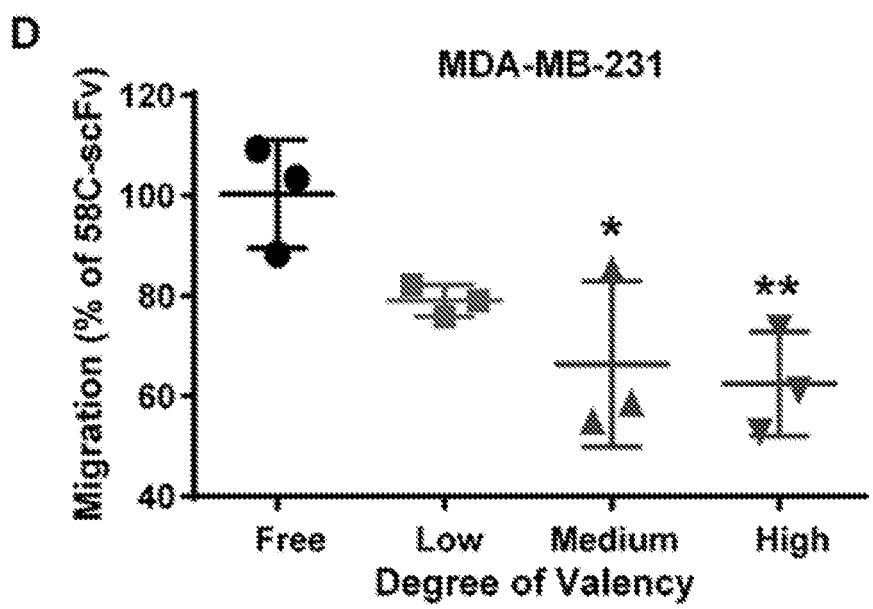
Figure 10:
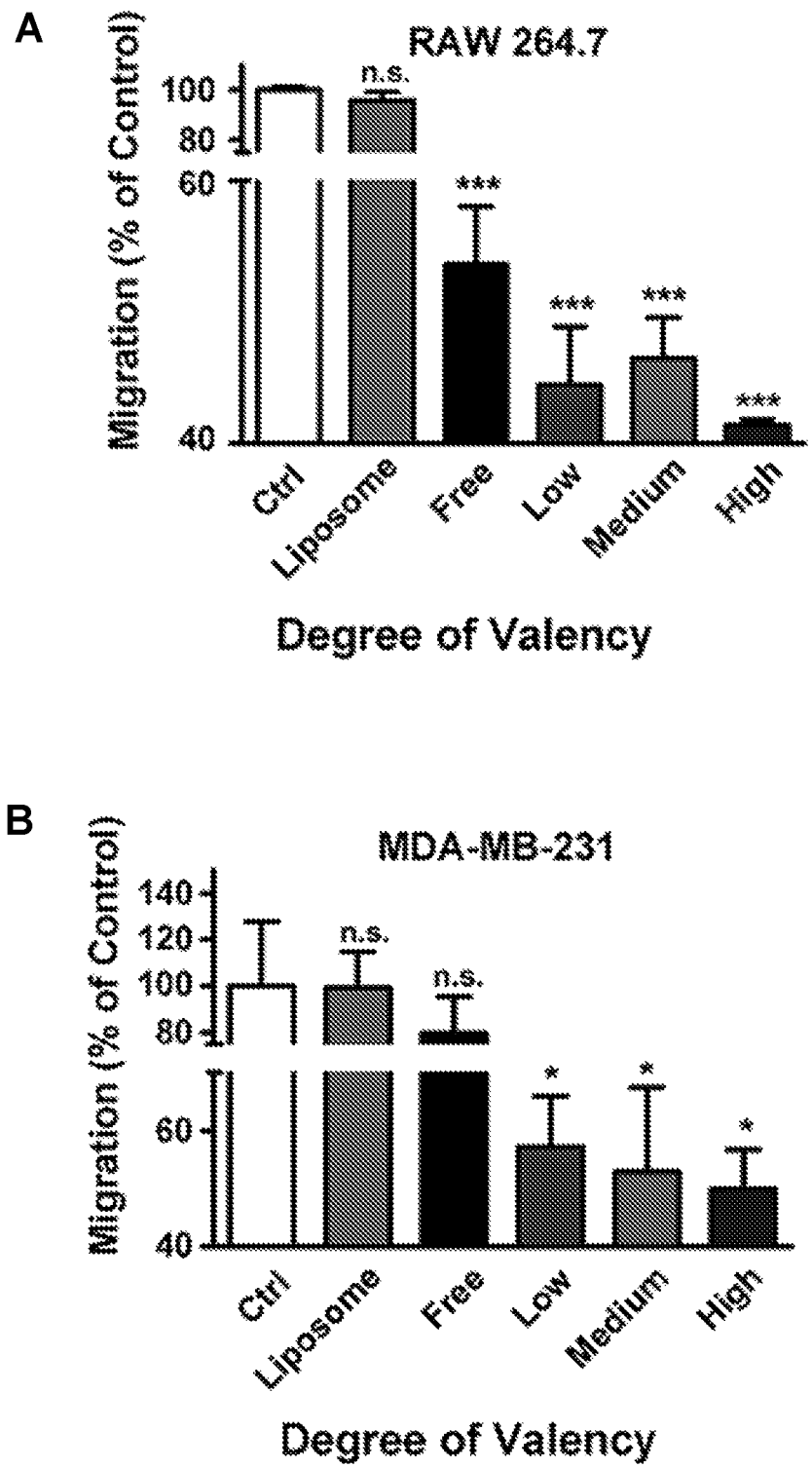
FIG. 10. Effect of free, monomeric 58C-scFv, multivalent 58C-scFv, and liposome only control on cellular migration. Transwell migration assay performed with RAW 264.7 murine macrophages (A) and MDA-MB-231 breast cancer cells (B). Conditions were normalized to the control (non-treated cells). Data are represented as mean±sd (n=3), *p<0.05, p<0.01, *p<0.001 with one-way ANOVA followed by Dunnett's post-test. Liposome only control was not significantly different from the non-treated control cells (n.s.). 58C-scFv (free and on liposomes) was used at a concentration of 88.9 nM.

CCR2 receptors cluster at the leading edge of cells when stimulated by CCL2. A multivalent targeting approach to CCR2 would prevent cellular migration better than the monomeric 58C-scFv (FIG. 4A). Liposomes were generated with varying molar ratios of DGS-NTA lipids to control the ligand density of 58C-scFv. The hydrodynamic diameter of the liposomes was between 146 nm and 155 nm as determined by DLS (Table 2) and TEM (FIG. 4B). Table 2 provides hydrodynamic diameter of the liposomal formulations containing increasing amounts of DGS-NTA(Ni) lipid for attachment of the His-tagged 58C-scFv by dynamic light scattering (DLS). 58C-scFv was incubated with liposomes containing 0.05 µM, 0.1 µM, or 0.3 µM of DGS-NTA(Ni) lipid, and the C-terminal hexa-histidine tag of the 58C-scFv was used for binding to the NTA(Ni) lipid. An excess of DGS-NTA (Ni) lipid was used to ensure maximum binding of 58C-scFv. The low valency formulation had approximately 14 58C-scFv per liposome, the medium valency formulation had approximately 28 58C-scFv per liposome, and the high valency formulation had approximately 84 58-scFv per liposome. Total protein was kept constant across conditions to assess how ligand density affected cellular migration. For the valency study, we normalized to the monomeric 58C-scFv, which already demonstrated a 1.75-fold and 1.87-fold enhancement over negative control for MDA-MB-231 and RAW 264.7 cells at a dose of 88.9 nM, respectively. Liposomes without 58C-scFv were not significantly different from the negative control (FIGS. 10A and 10B). Multivalent display of 58C-scFv at low, medium, and high valency further inhibited migration in RAW 264.7 and MDA-MB-231 cells (FIGS. 4C&D). At the highest valency, there was a significant 25% reduction in RAW 264.7 migration compared to free 58C-scFv. For MDA-MB-231 cells, multivalent display of 58C-scFv resulted in a significant 40% reduction in migration compared to free monomeric 58C-scFv.

TABLE 2

| Liposome Formulation | Hydrodynamic Diameter (mean ± sd) | Polydispersity Index (mean ± sd) |
|---|---|---|
| DSPC:DGS-NTA(Ni):Chol (75:5:20) | 146.1 ± 8.62 nm | 0.204 ± 0.016 |
| DSPC:DGS-NTA(Ni):Chol (70:10:20) | 147.0 ± 23.7 nm | 0.243 ± 0.032 |
| DSPC:DGS-NTA(Ni):Chol (50:30:20) | 155.2 ± 6.39 nm | 0.136 ± 0.016 |

The Effect of 58C-scFv on Macrophage Polarization

Figure 5:
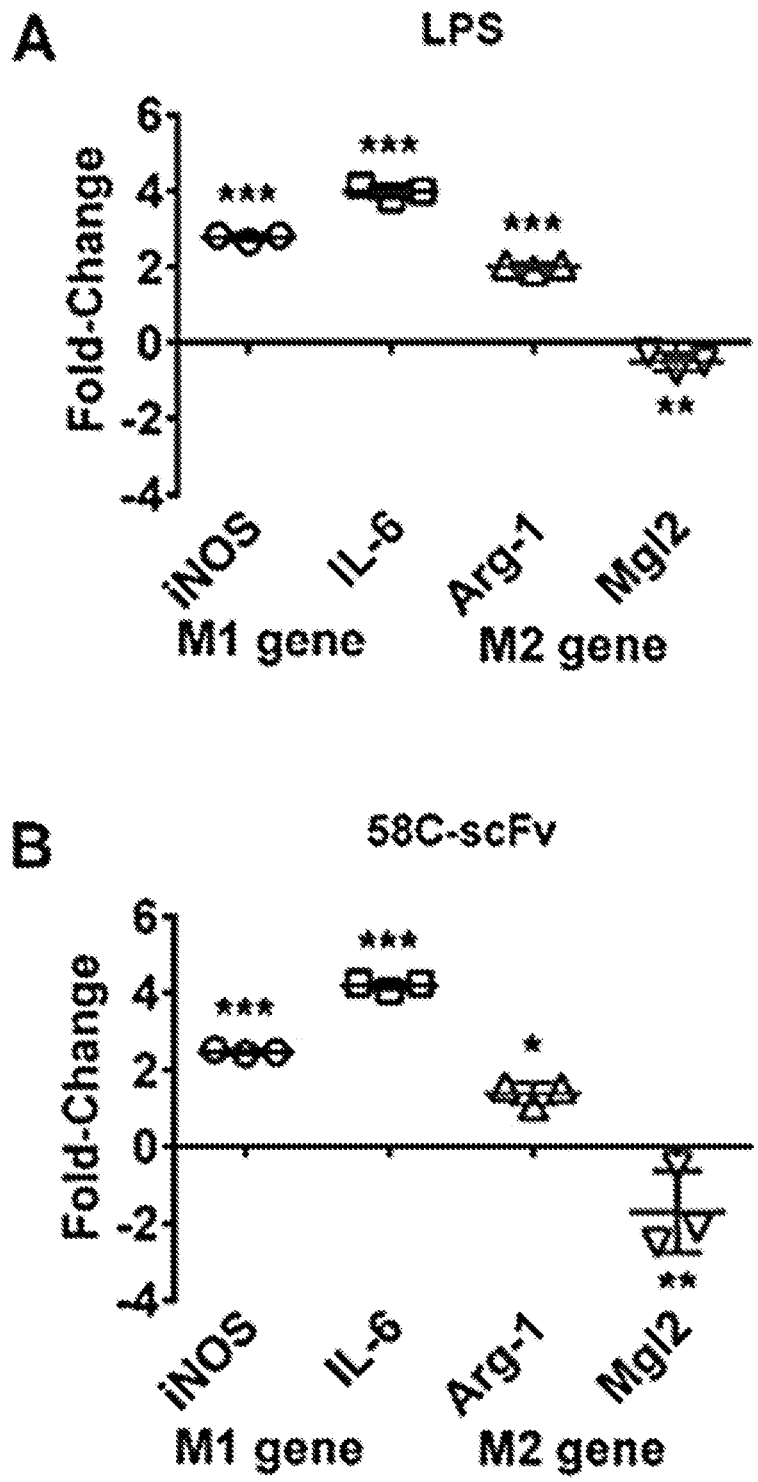
FIG. 5. Effect of free, monomeric 58C-scFv on macrophage polarization. iNOS and IL-6 were used as M1 markers and Arg-1 an Mgl2 were used as M2 markers. Raw 264.7 macrophages treated with (A) LPS, (B), 58C-scFv, (C), IL-4, and (D) 58C-scFv+Il4. In A-C the genes values were normalized to the untreated control, where D was normalized to the IL-4 only control. (E) Schematics of macrophage polarization. (F) Ratios of M1/M2 marker genes across different conditions normalized to untreated control. Data are represented as mean±sd, *p<0.05, p<0.01, *p<0.001 with one-way ANOVA followed by Dunnett's post-test.
Figure 5:
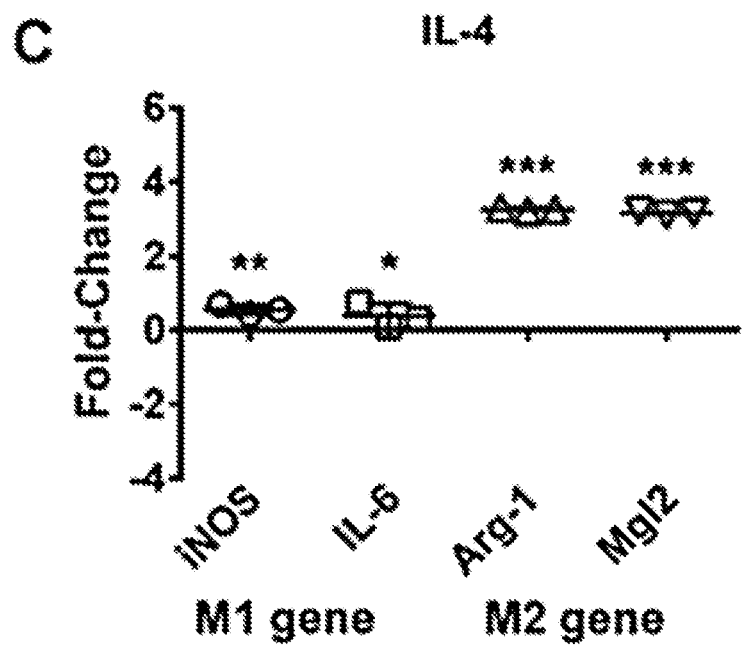
Figure 5:
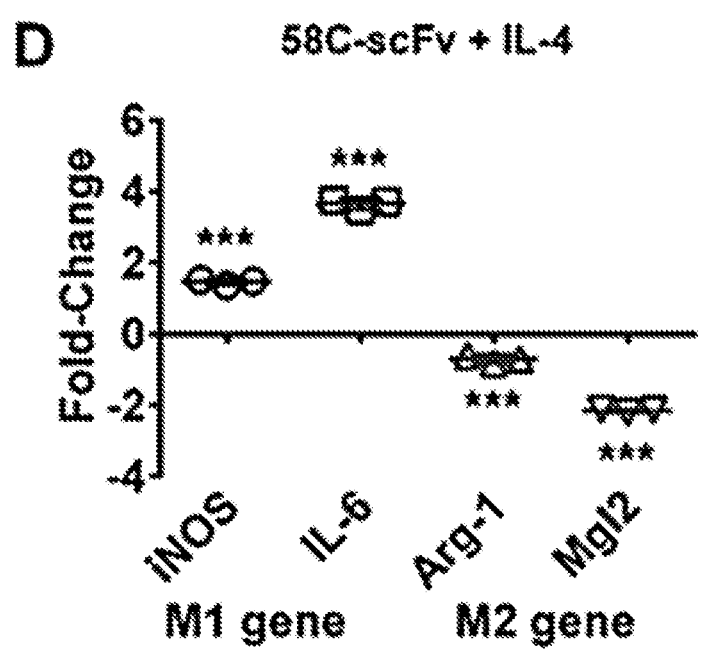
Figure 5:
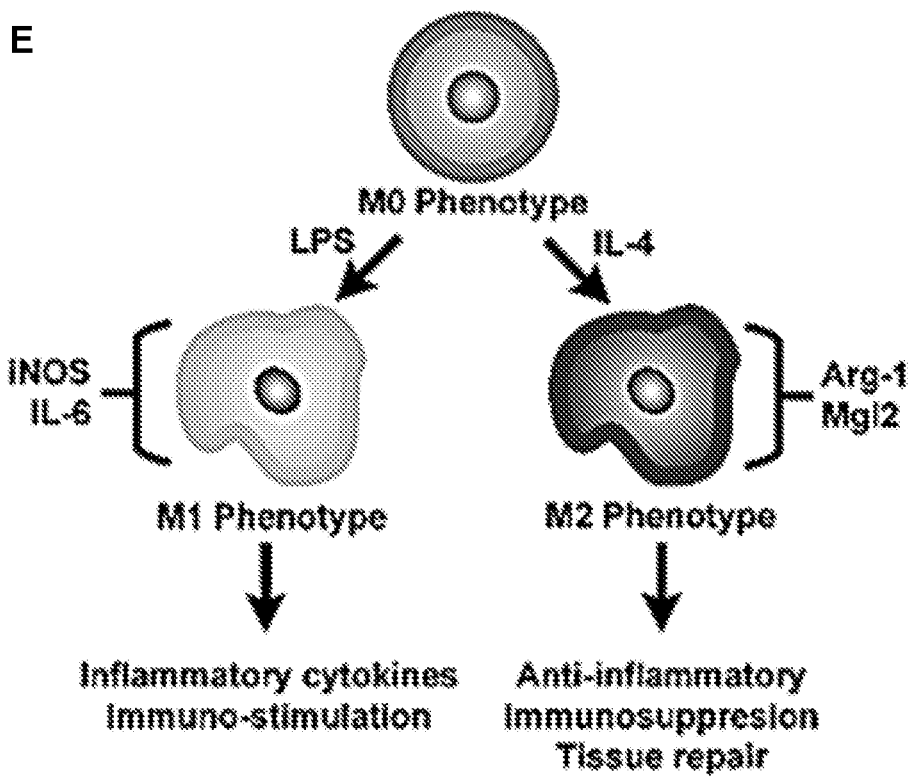
Figure 5:
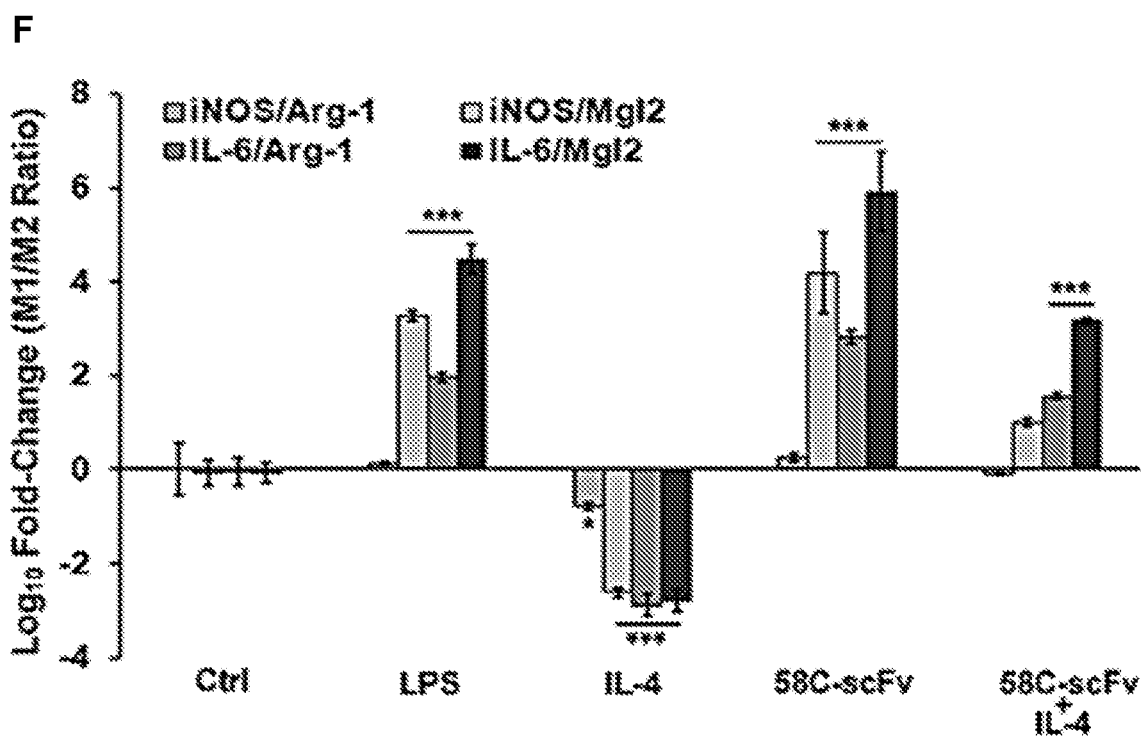
Figure 11:
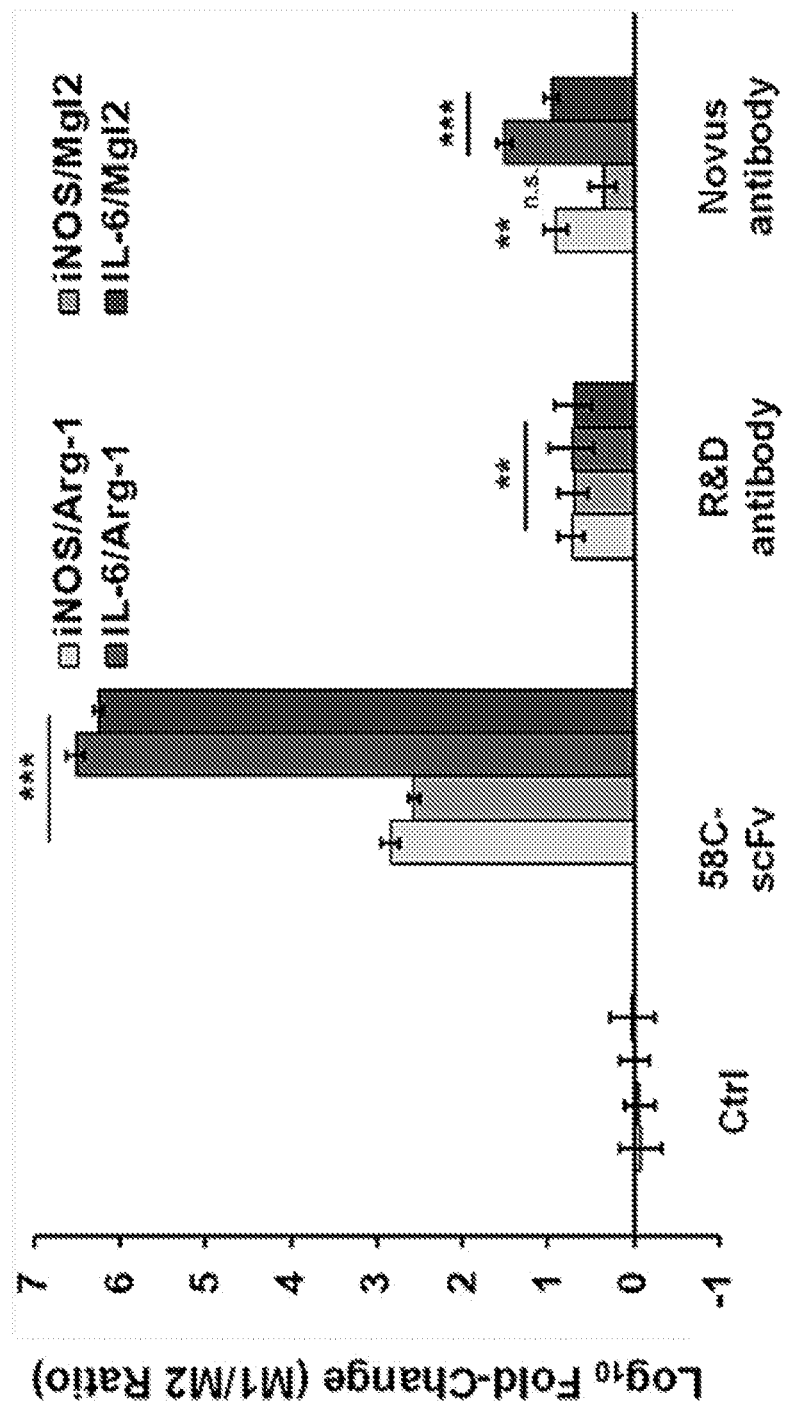
FIG. 11. Effect of free, monomeric 58C-scFv and two different commercially available CCR2-targeted antibodies (Clone #475301, R&D, Minneapolis, MN and NBP1-48337, Novus, Littleton, CO) on macrophage polarization. The same molar concentration was used for all three antibodies. The ratios of the M1 markers (IL-6 and iNOS) and M2 markers (Arg-1 and Mgl2) were used to compare the different conditions (M1/M2 ratio). Data are presented as mean±sd, p<0.01, *p<0.001 with one-way ANOVA followed by Dunnett's post-test.
Figure 12:
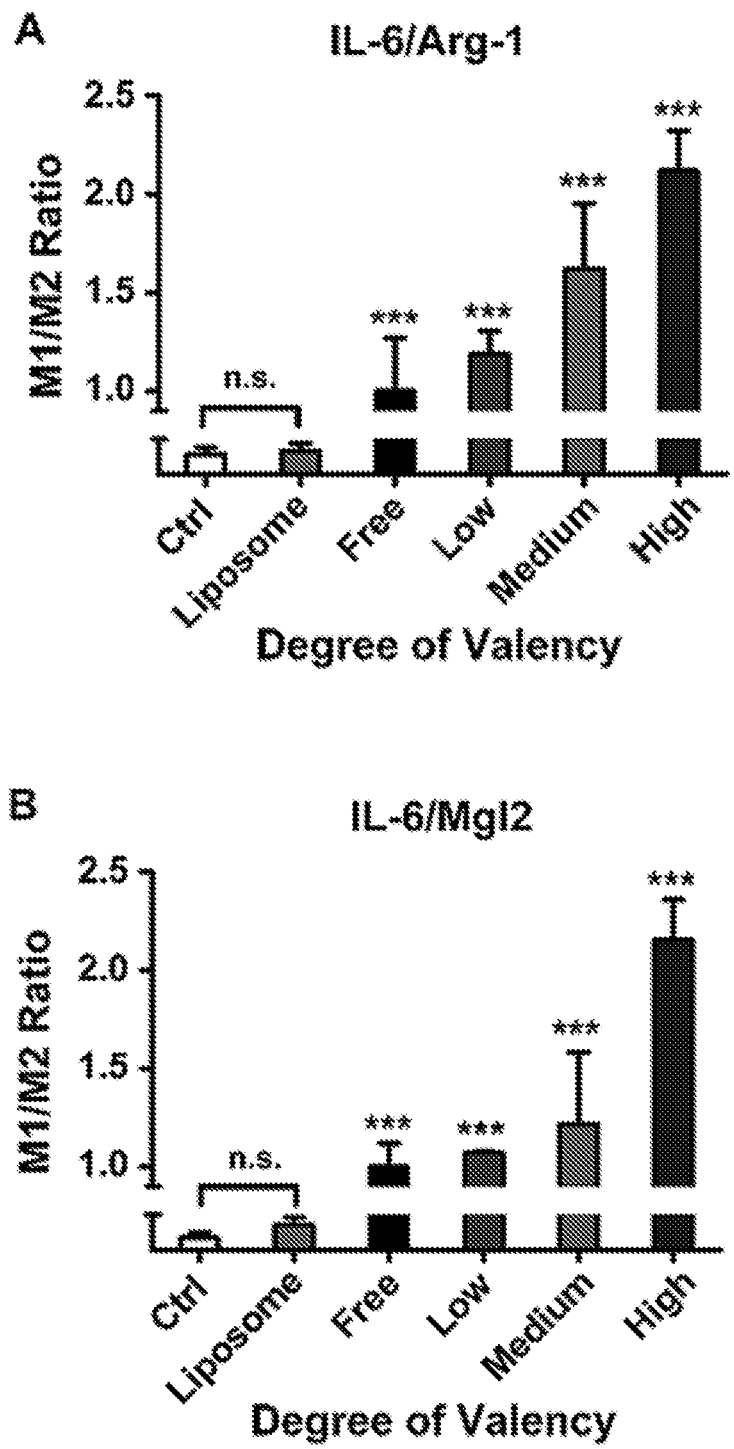
FIG. 12. Effect of free, monomeric 58C-scFv, multivalent 58C-scFv, and liposome only control on macrophage polarization. (A,B,C,D). The ratios of the M1 markers (IL-6 and iNOS) and M2 markers (Arg-1 and Mgl2) were used to compare the different conditions (M1/M2 ratio). From left to right: Control, liposome with no 58C-scFv, 58C-scFv monomers; 58C-scFv displayed on liposomes with increasing ligand density: low ligand density, medium ligand density, and high ligand density. The dose was normalized to the 58C-scFv concentration. The M1/M2 ratio was normalized to the free, monomeric 58C-scFv. Liposome only control was not statistically significant (n.s.) from the untreated control (non-treated cells). Data are presented as mean±sd, p<0.01, *p<0.001 with one-way ANOVA followed by Dunnett's post-test.
Figure 12:
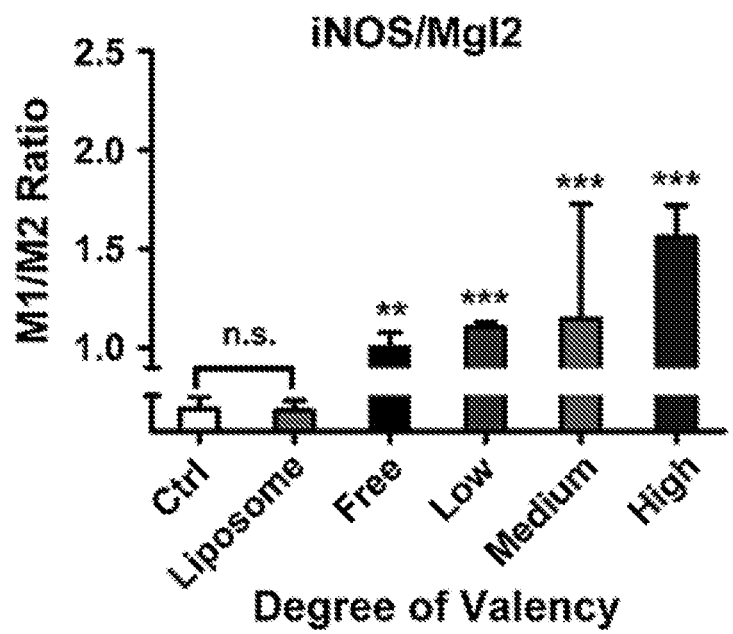
Figure 12:
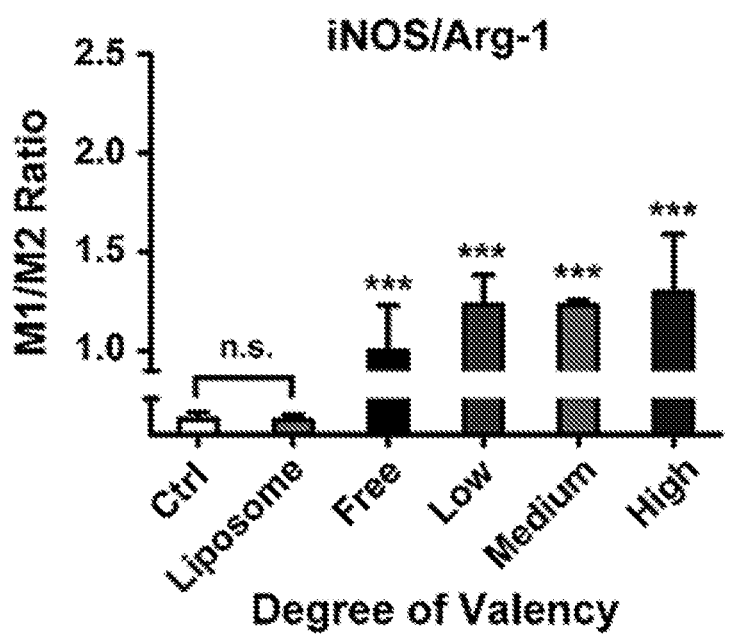

Cancer cell secretion of CCL2, a CCR2 agonist, into the tumor microenvironment can polarize macrophages to an M2 phenotype. The CCR2-targeting 58C-scFv was incubated with RAW 264.7 macrophages to test our hypothesis that CCR2 antagonism would polarize macrophages toward an M1 phenotype. Macrophages were polarized to M1 (iNOS and IL-6 expressing) by the addition of LPS, or to M2 (Arg-1 and Mgl-2 expressing) by the addition of IL-4. As expected, LPS induced M1 gene expression and downregulated Mgl2 gene expression compared to the untreated control (FIG. 5A). The 58C-scFv induced a quantitatively similar expression pattern to that of LPS, suggesting that 58C-scFv polarized macrophages to the M1 phenotype (FIG. 5B). IL-4 increased both Arg-1 and Mgl2 gene expression compared to the untreated control (FIG. 5C). Even in the presence of IL-4, the 58C-scFv still downregulated the M2 gene expression and upregulated M1 gene expression compared to the IL-4 only control (FIG. 5D). For cancer therapy, it is beneficial to have macrophages with M1 rather than M2 phenotypes because M2 macrophages have a tumor-promoting phenotype. To this end, we used four genes (two M1 and two M2 genes) to assay for the relative phenotype of macrophages upon different conditions (FIG. 5E). The ratios of M1 and M2 genes corroborated the phenotype of macrophages suggested from our single gene analysis (FIG. 5F). For LPS, three of the four M1/M2 ratios were significantly above control, suggesting the macrophages had an M1 phenotype. For IL-4, all four M1/M2 ratios were significantly below control, suggesting the macrophages had an M2 phenotype. The 58C-scFv had similar fold-changes as the LPS group with three of the four ratios being statistically significant. The M1/M2 ratio for monomeric 58C-scFv was significantly increased over the negative control by $1.0 \times 10^4$-fold (iNOS/Arg-1), $5.1 \times 10^4$-fold (iNOS/Mgl2), $3.4 \times 10^5$-fold (IL-6/Arg-1), and $1.7 \times 10^6$-fold (IL-6/Mgl2) (FIG. 5F). When 58C-scFv was co-incubated with the M2 promoting agent, IL-4, two of the ratios were significantly increased over control, with a clear trend for the third ratio (iNOS/Mgl2) having an M1 phenotype. Co-incubation of the IL-4 and 58C-scFv demonstrated 58C-scFv is able to polarize macrophages back to an M1 phenotype. 58C-scFv significantly increased the M1/M2 ratios in macrophages by 3- to 9-fold compared to two commercially available CCR2-targeted antibodies (FIG. 11).

Impact of 58C-scFv Multivalency on Macrophage Polarization

We next investigated the effect of multivalency on macrophage polarization. Macrophages were first polarized to an M2 phenotype with IL-4 followed by incubation with different ligand densities of 58C-scFv (FIG. 6A). Monomeric 58C-scFv and all liposome-bound 58C-scFv shifted the macrophage phenotype from M2 to M1, as measured by the M1/M2 gene ratio (FIG. 6B-E). Four different ratios (iNOS/Arg-1, iNOS/Mgl2, IL-6/Arg-1, and IL-6/Mgl2) were compared across conditions. The M1/M2 ratios for the liposomes without 58C-scFv were not statistically different from the negative control (FIG. 12A-D).

Figure 6:
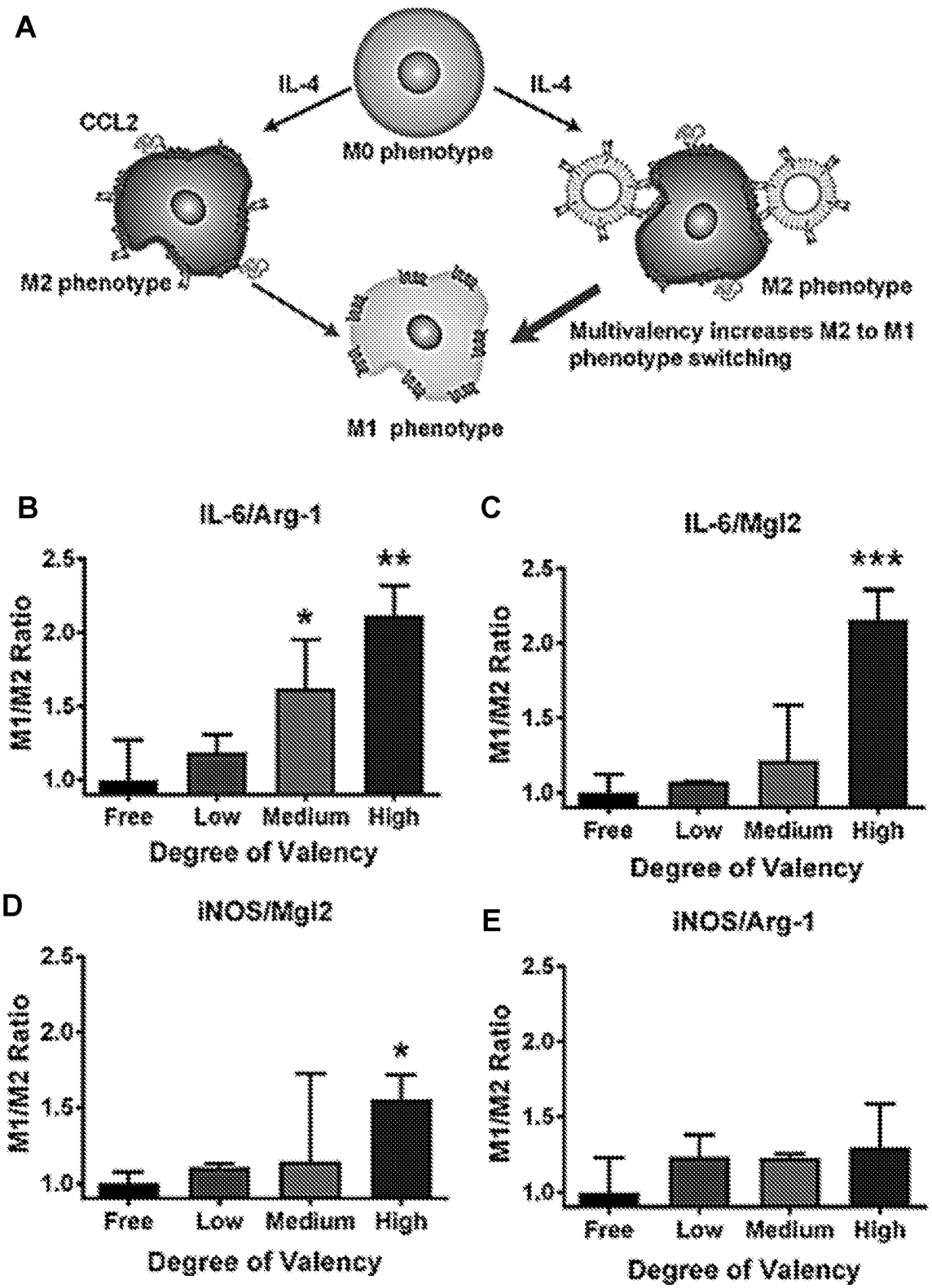
FIG. 6. Effect of free, monomeric 58C-scFv and multivalent 58C-scFv on macrophage polarization. (A) Multivalent 58C-scFv induces a stronger M1 phenotype than monomeric, free 58C-scFv. (B,C,D,E) The ratios of the M1 markers (IL-6 and iNOS) and M2 markers (Arg-1 and Mgl2) were used to compare the different conditions (M1/M2 ratio). From left to right: 58C-scFv monomers; 58C-scFv displayed on liposomes with increasing ligand density: low ligand density, medium ligand density, and high ligand density. The dose was normalized to the 58C-scFv concentration. The M1/M2 ratio was normalized to the free, monomeric 58C-scFv. Liposome only control was not statistically significant from the untreated control (Supplemental FIG. 5). Data are represented as mean±sd, *p<0.05, p<0.01, *p<0.001 with one-way ANOVA followed by Dunnett's post-test.
Figure 7:
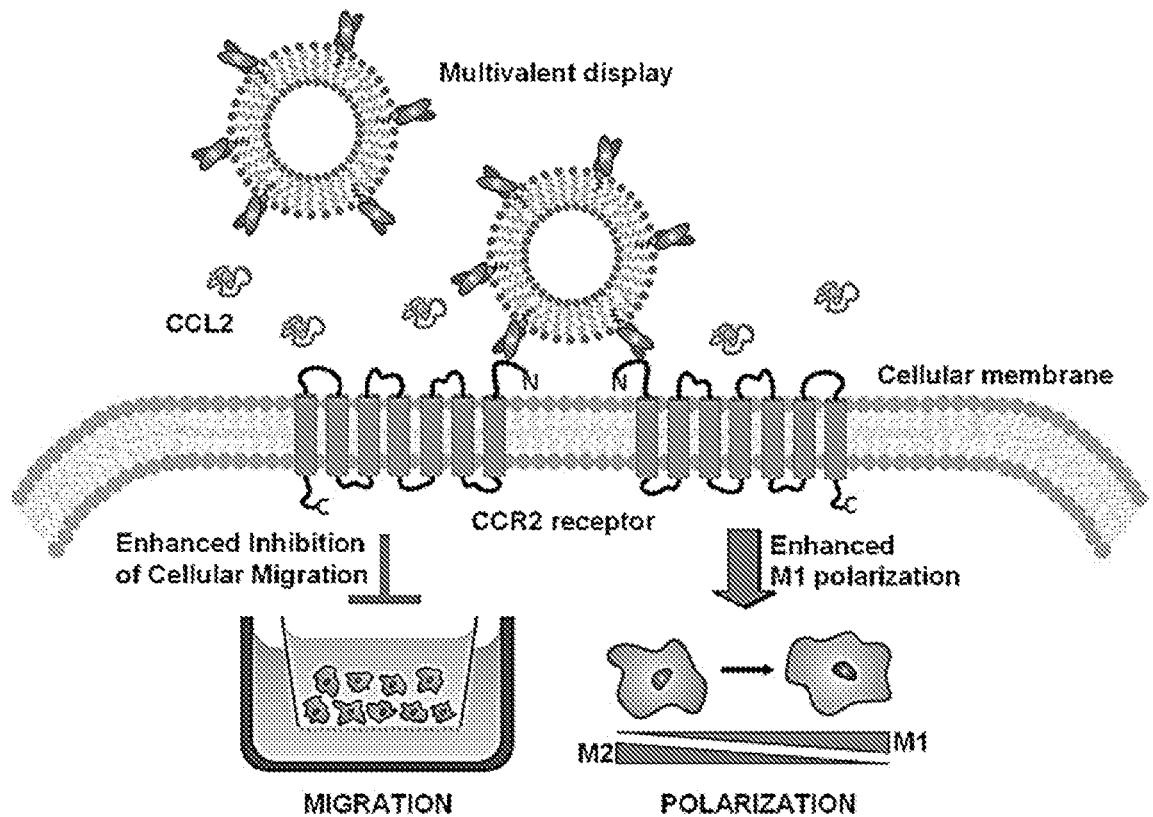
FIG. 7. Schematic of multivalent targeting against CCR2 receptors and the observed effects on cellular migration and macrophage polarization. Multivalent display of 58C-scFv enhanced inhibition of cellular migration and increased M1 polarization of macrophages compared to monomeric, free 58C-scFv.
Figure 13:
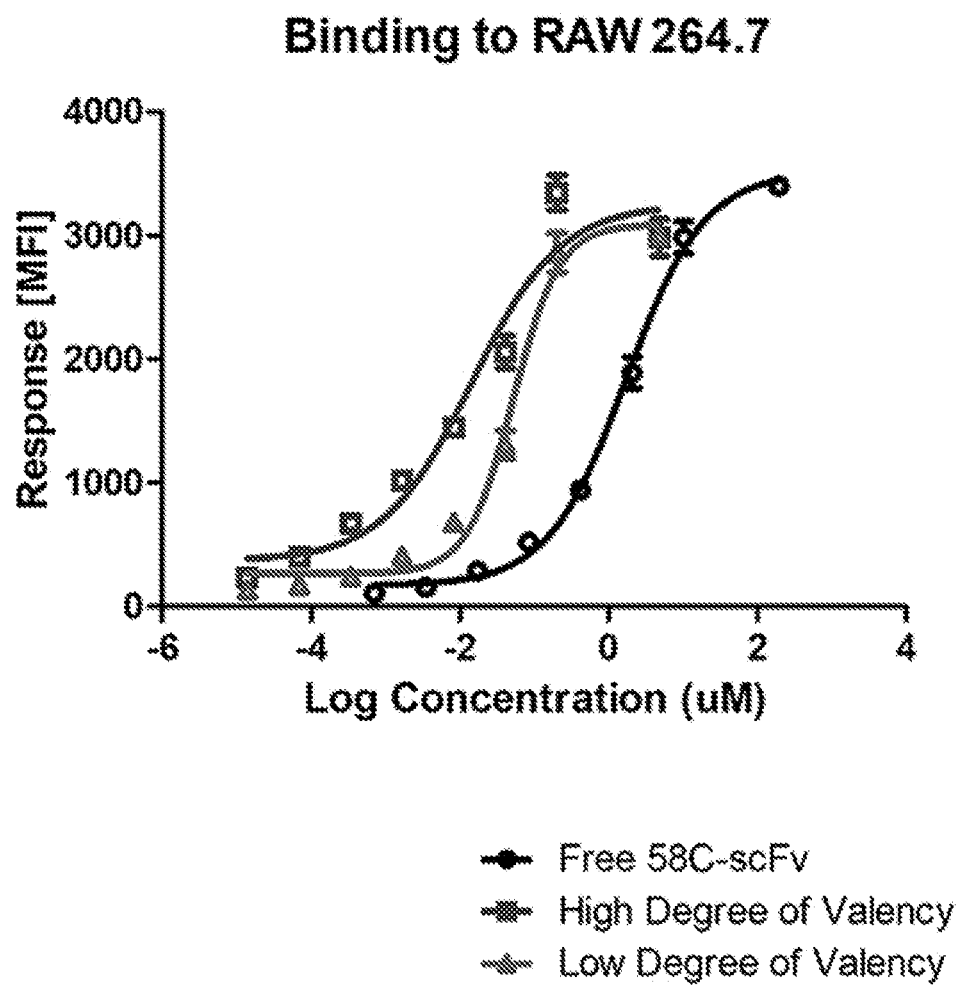
FIG. 13. Binding of monomeric 58C-scFv (circles), low valency 58C-scFv attached to liposomes (triangles), and high valency 58C-scFv attached to liposomes (squares) to RAW 264.7 macrophage cells as determined by flow cytometry. The binding affinities for this experiment were $K_D$=1.272 µM for the 58C-scFv monomer, $K_D$=278 nM for the low valency 58C-scFv attached to liposomes, and $K_D$=159 nM for the high valency 58C-scFv attached to liposomes. This is an 8-fold increase in binding affinity from the free to high valency and about a 1.75-fold increase from the low to high valency formulation. The liposomes were incubated with DyLight 650 NHS Ester labeled 58C-scFv at 4° C. overnight. Cells were detached with 5 mM EDTA and re-suspended in PBS to a concentration of 50,000 cells per 300 µL. The cells were incubated with various dilutions of DyLight 650 NHS Ester labeled 58C-scFv (free, low degree of valency, or high degree of valency) for 1 h at 4° C. Cells were washed three times with 5% BSA and analyzed in the APC channel of a MACSQuant Analyzer 10 flow cytometer (Miltenyi Biotec, Bergisch Gladbach, Germany).

Moreover, the three different ligand densities of 58C-scFv outperformed the monomeric 58C-scFv with a trend for increasing M1/M2 ratio from the lowest to the highest valency. Compared to monomeric 58C-scFv, the highest valency produced 2.2-fold, 2.1-fold, 1.6-fold, and 1.3-fold higher M1/M2 ratios for IL-6/Mgl2, IL-6/Arg-1, iNOS/Mgl2, and iNOS/Arg-1, respectively. Further, the IL-6/Mgl2, IL-6/Arg-1, and iNOS/Mgl2 ratios were significantly higher than the monomeric 58C-scFv at the highest valency (FIG. 6, FIG. 13). The medium valency was also significantly higher for the IL-6/ARG-1 ratio. The monomeric 58C-scFv strongly polarized macrophages to an M1 phenotype, but to a lesser degree than multivalent 58C-scFv.

Example 2

Figure 14:
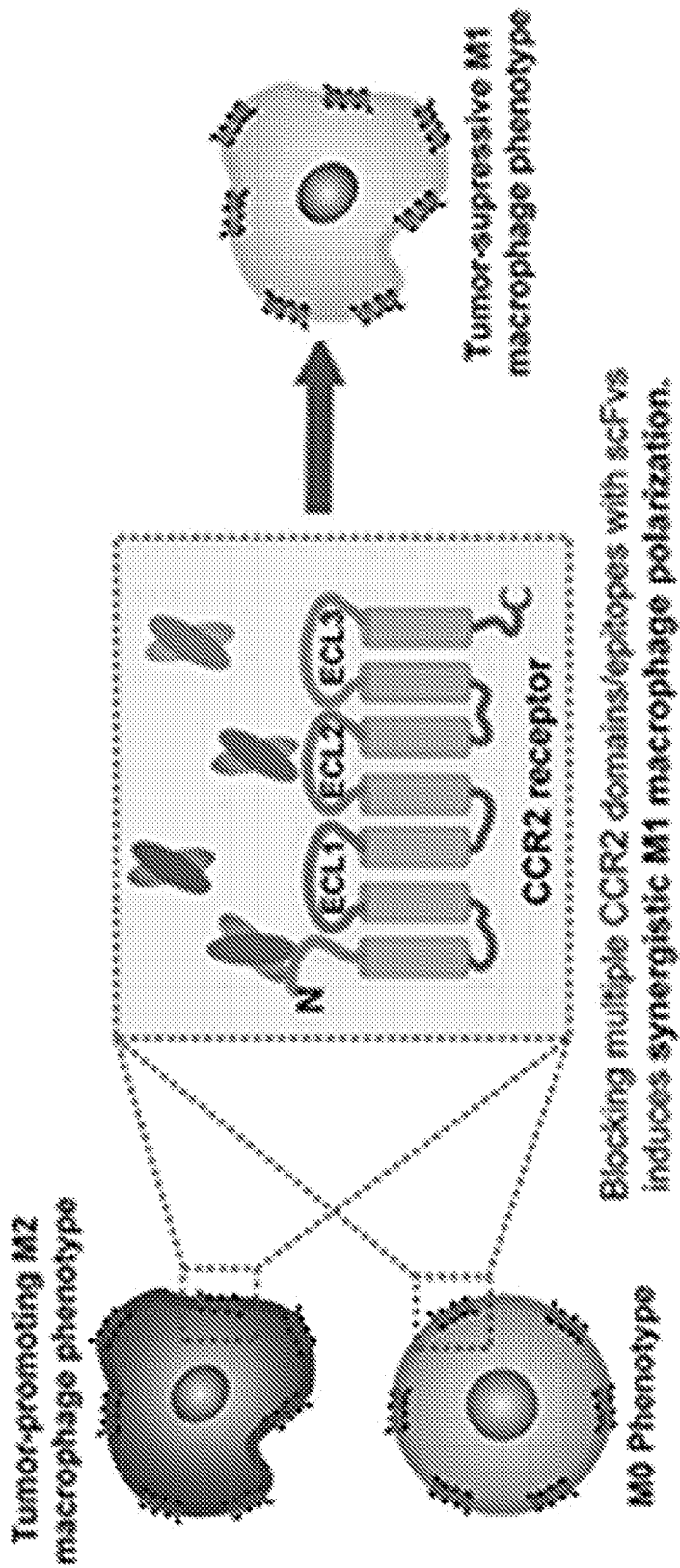
FIG. 14. Representation of simultaneous targeting of multiple CCR2 domains (epitopes) for enhancing M1 macrophage polarization.

The present disclosure takes advantage of recent discoveries (FIG. 14). Although the C-C chemokine receptor type 2 (CCR2) is composed of an N-terminal domain (NTD) and three extracellular loops (ECL)—herein referred to as ECL1, ECL2, and ECL3-conventional CCR2 targeting approaches mostly target the NTD, neglecting the other domains. This disclosure describes that targeting the NTD of the CCR2 receptor not only inhibits monocyte migration but also induces macrophage polarization towards the tumor-suppressive M1 phenotype. The NTD targeting single-chain variable fragment (NTD-scFv) increases M1 macrophage polarization 7-fold over commercially available antibodies and, furthermore, when the NTD and ECL2 are simultaneously targeted, there is a dramatic increase in M1 polarization by ~20-30-fold. This disclosure provides that simultaneous targeting of multiple CCR2 domains (ECLs and NTD): (a) enhances M1 macrophage polarization and (b) better inhibits macrophage migration compared to targeting only one domain (FIG. 14).

Figure 2:
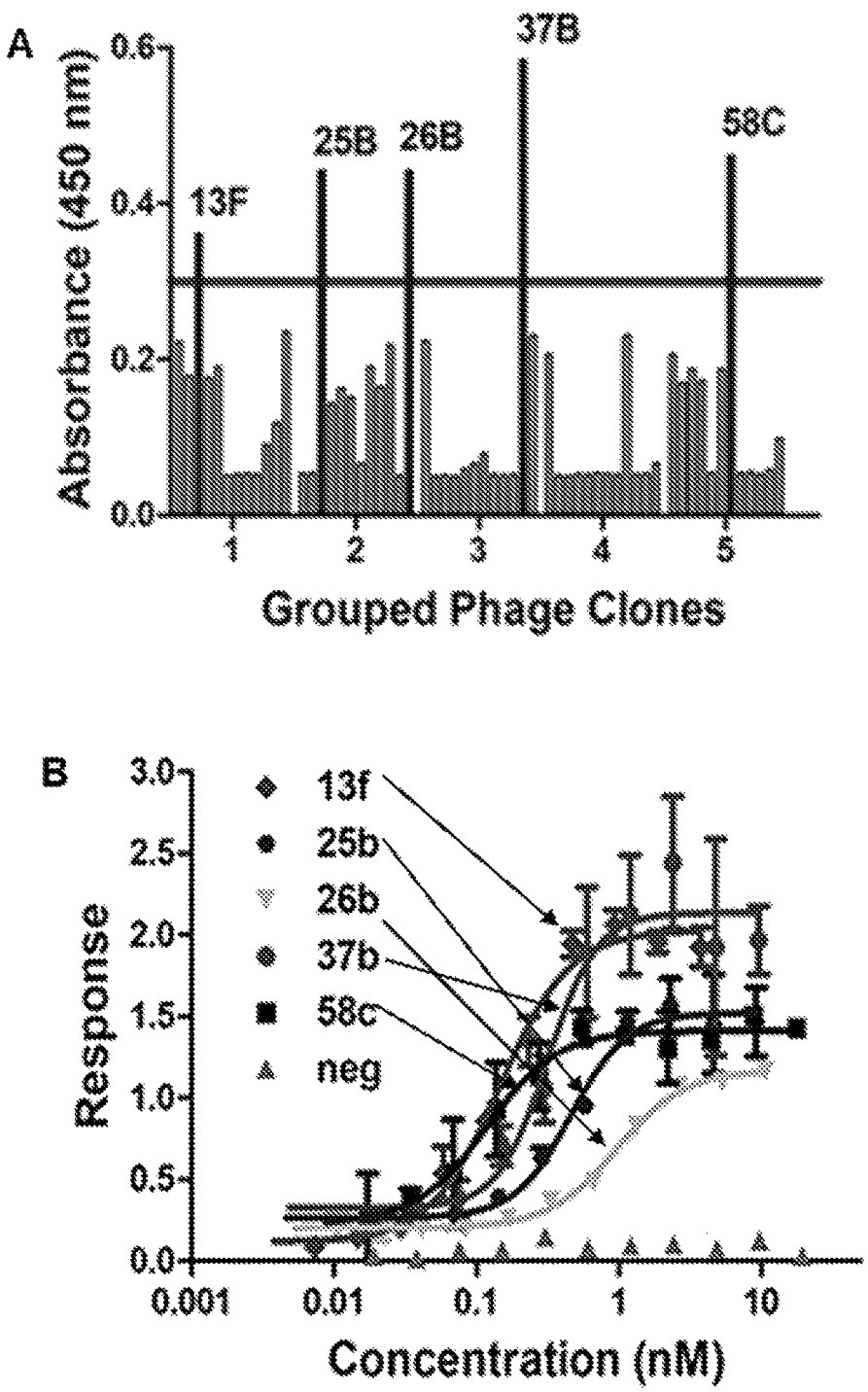
FIG. 2. Identification and characterization of 58C-scFv binding to CCR2. (A) Phage ELISA of clones generated through affinity selection using a scFv library. (B) Binding affinity of the top 5 phage clones as analyzed by ELISA (C) Binding of the recombinantly expressed 58C-scFv to the N-terminal domain of CCR2 as analyzed by ELISA (KD=59.8±13.9 nM) (D) SDS-PAGE of purified 58C-scFv (MW approx. 33 kDa) on a 12% gel: ladder (lane 1), 58C-scFv sample (lane 2). (E) 58C-scFv binding to RAW 264.7 (F) and MDA-MB-231 cells was concentration-dependent. (G) Mean fluorescent intensity (MFI) following incubation of HEK, MDA-MB-231, and Raw264.7 cells with the DyLight-650 labeled 58C-scFv. The MFI was determined at 2.5 µM for MDA-MB-231 and HEK, and RAW 264.7 cells. Data are represented as mean±sd, *p<0.05, p<0.01, *p<0.001 with one-way ANOVA followed by Dunnett's post-test.
Figure 2:
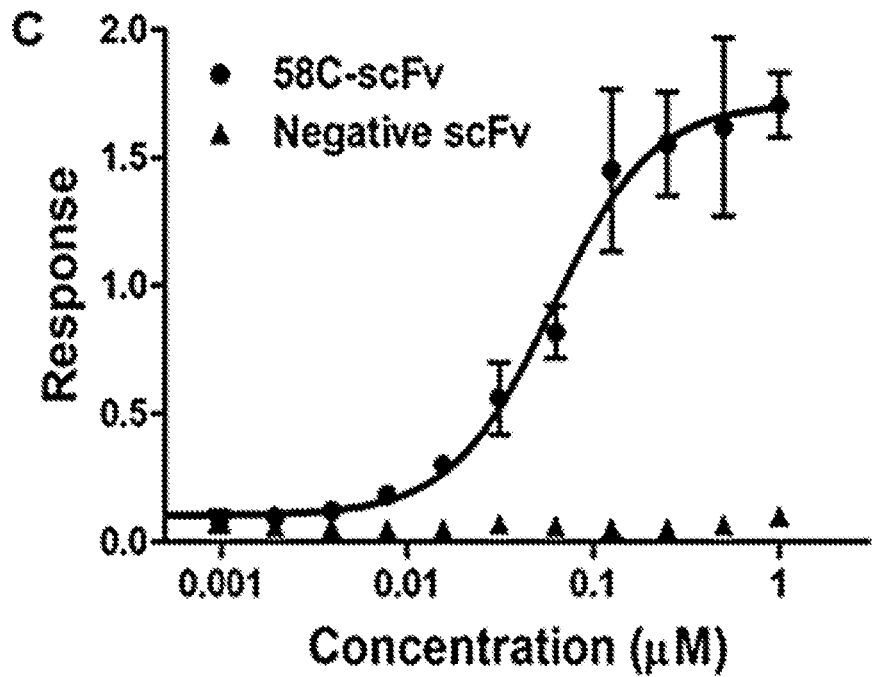
Figure 2:
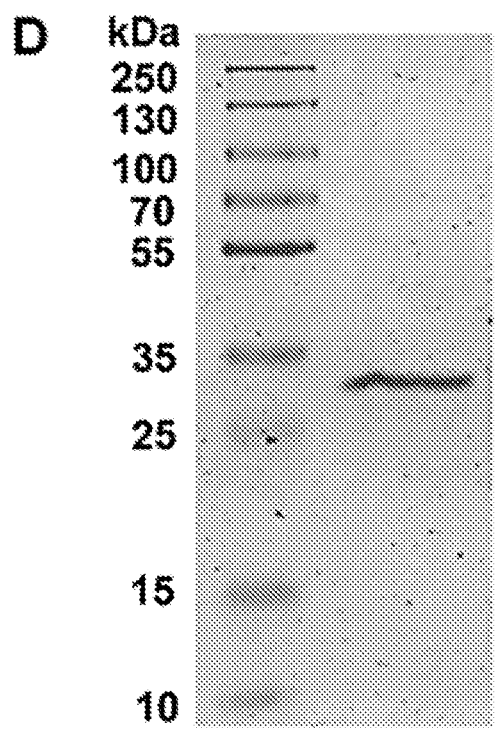
Figure 2:
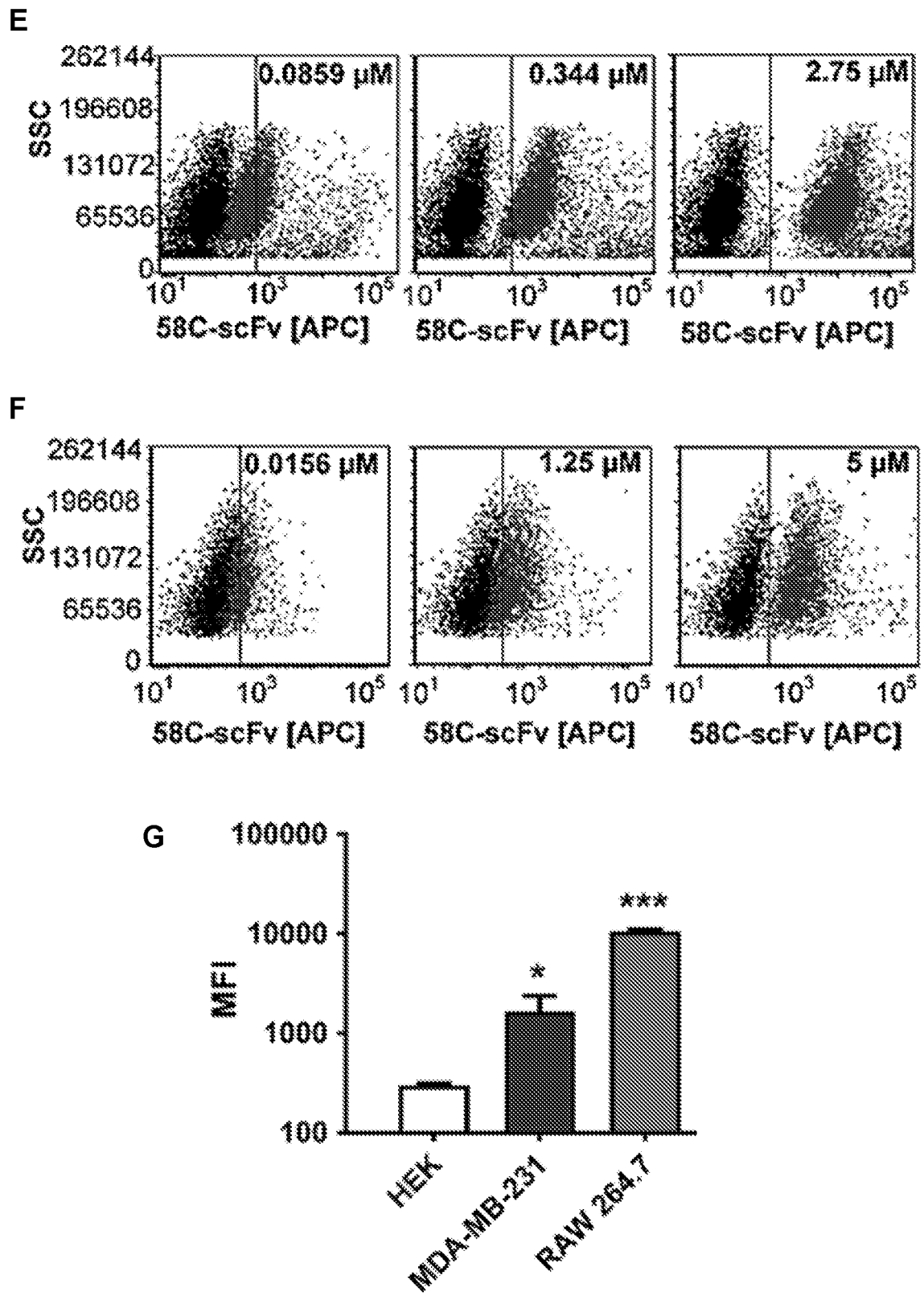
Figure 15:
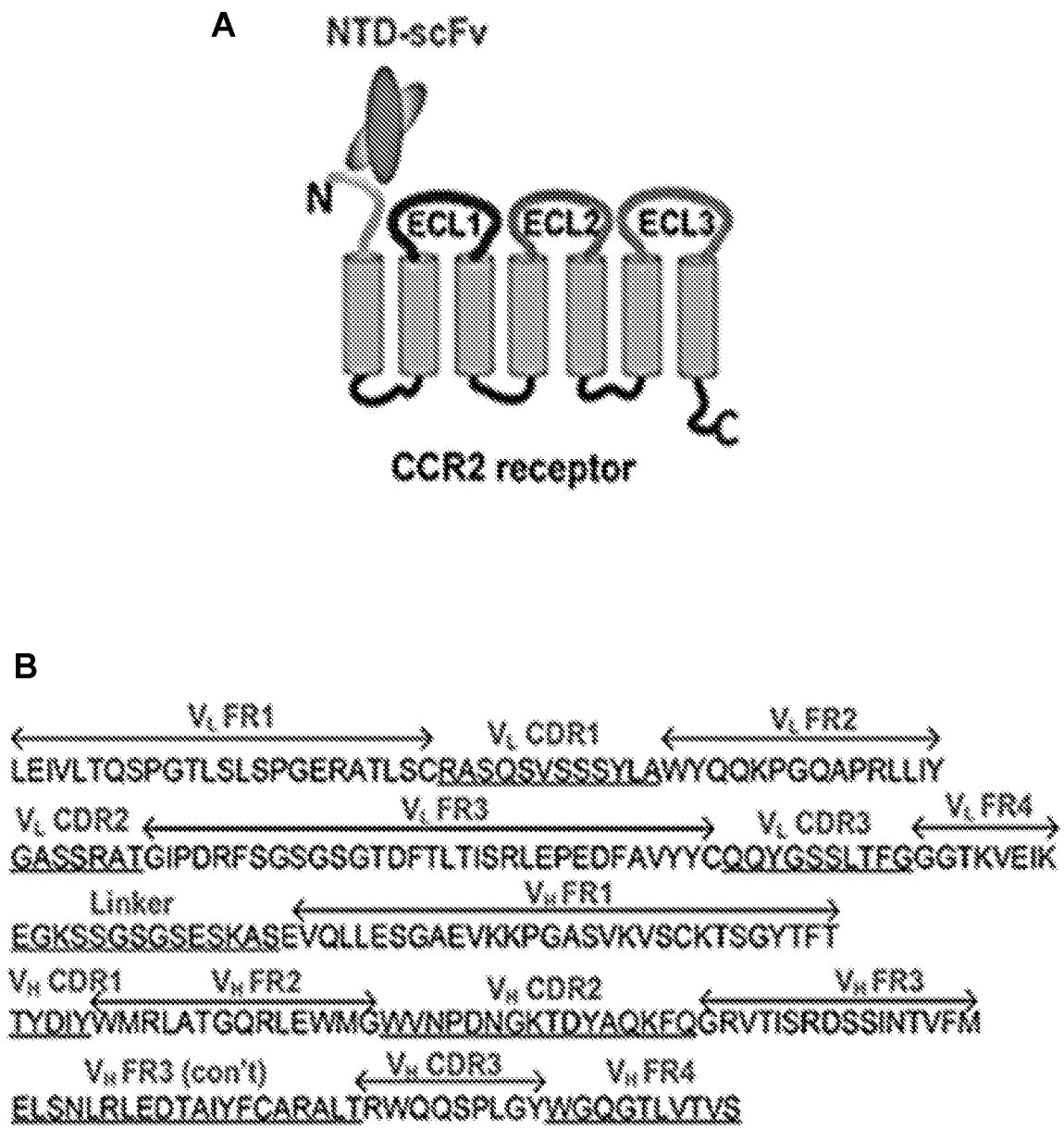
FIG. 15. NTD-scFv (A) binds with high affinity to the N-terminal domain (NTD) of the CCR2 receptor. (B) Protein sequence of the NTD-scFv (SEQ ID NO:61; same as the sequence in SEQ ID NO:57 without the last S at the C-terminus). The framework regions (light ($V_L$ FR) and heavy chains ($V_H$ FR)) and complementarity determining regions (light ($V_L$ CDR) and heavy chains ($V_H$ CDR)) are highlighted.
Figure 16:
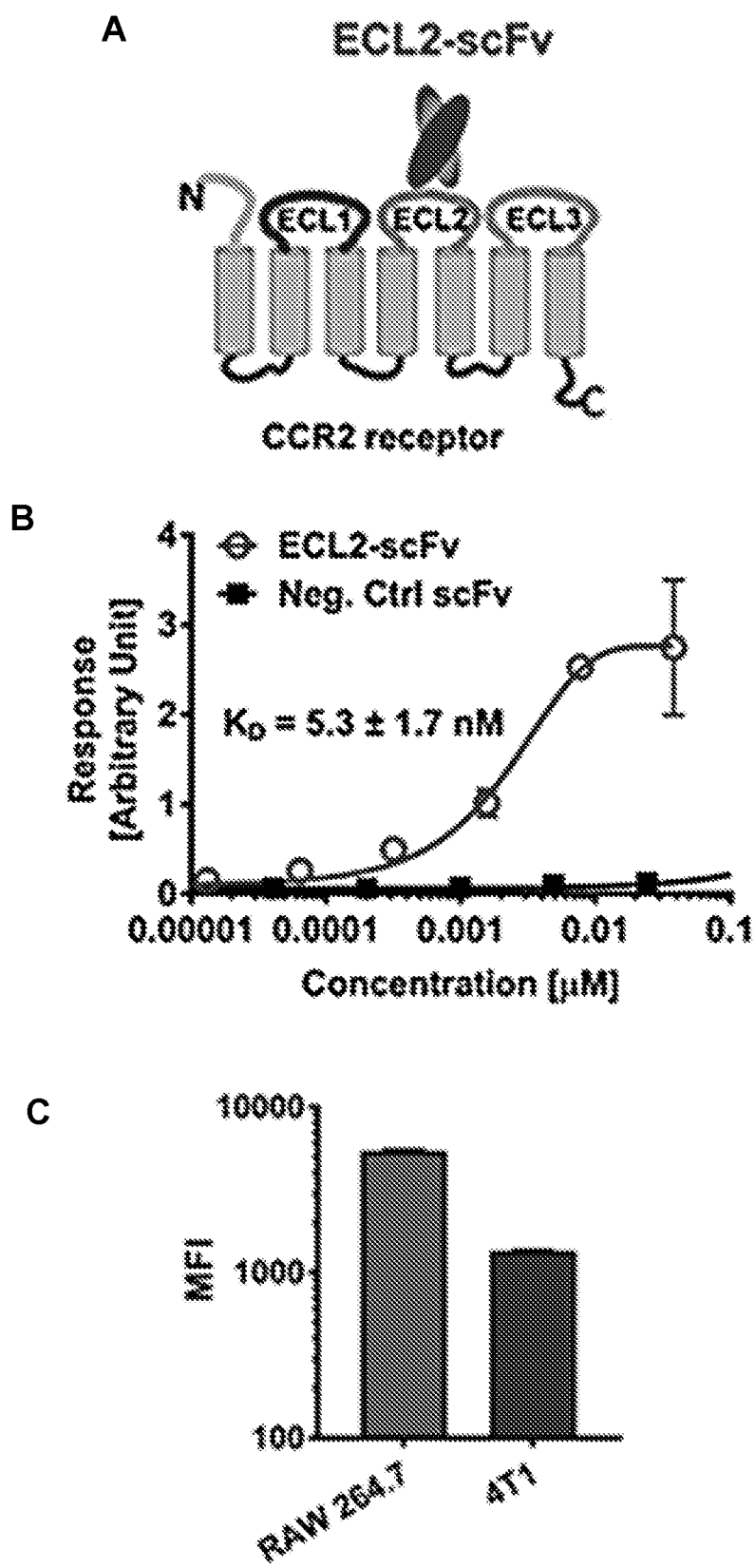
FIG. 16. ECL2-scFv binding to the ECL2 domain of the CCR2 chemokine receptor. (A,B) Binding affinity of the ECL2-scFv to the ECL2 domain is $K_D$=5.3 nM±1.7 nM, (C) ECL2-scFv binds both to RAW 264.7 cells and 4T1 breast cancer cells as analyzed by flow cytometry and expressed as mean fluorescence intensity (MFI).

This disclosure provides recombinantly expressed scFvs that specifically target the CCR2 NTD and the ECL2 as shown in FIGS. 15A, 15B and 16. Both scFvs bind to their respective targets in the low nanomolar range. The NTD-scFv has a binding affinity of KD=59.8±13.9 nM (FIG. 2) and the ECL2-scFv has a binding affinity of KD=5.3±1.7 nM (FIG. 16). Both scFvs bind to cells expressing CCR2 such as RAW 264.7 macrophages and MDA-MB-231 and 4T1 breast cancer cells (FIGS. 2E, F G & FIG. 16C). Furthermore, both scFvs are cross-reactive and bind to human CCR2, which is important for future clinical translation.

Method to Screen for scFv Binders Specifically Targeting the CCR2 ECL of Interest.

This disclosure describes the phage display screening approach used to identify novel scFvs against the remaining ECLs of CCR2, including ECL 1 and ECL3 (FIG. 1). Briefly, biotinylated peptides corresponding to ECL1 (AANEWVFGNIMCK-Biotin) (SEQ ID NO:20) and ECL3 (QESLGMSNCVID-KHLDQK-Biotin) (SEQ ID NO:21) of the murine CCR2 chemokine receptor will be captured on magnetic streptavidin-coated beads, and four affinity selection rounds will be performed. The biotinylated peptides will be custom synthesized by Abclonal (Woburn, MA).

The selection can be performed using a phage display library constructed from peripheral human blood lymphocytes expressing single-chain fragments of antibodies. First, the phage library was incubated with the biotinylated peptide corresponding to ECL1 or ECL3. The mixture is then incubated with magnetic streptavidin beads to bind the biotinylated peptides along with the bound phages. After several PBS washes, glycine (pH 2) is used to compete off the bound phages. After neutralizing with Tris buffer, TG1 *E. coli* cells are infected with the phages and allowed to grow at 37° C. for 1 h. The mixture is plated onto carbenicillin-containing agar plates and grown overnight at 30° C. The TG1 *E. coli* cells are scraped off the plate and grown in suspension culture for isolation of phages that are used for the $2^{nd}$ round of selection. This is repeated for the $3^{rd}$ and $4^{th}$ round of selection. With each round, the stringency of the conditions is enhanced. To identify CCR2 ECL binders, single bacterial colonies will be picked after the fourth round of selection for phage amplification followed by a phage ELISA. Clones yielding a signal above background will be sequenced and further analyzed with regard to binding affinity.

Simultaneous Targeting of the NTD and ECL2 Domains of CCR2 Mediates Synergistic M1 Macrophage Polarization.

Figure 17:
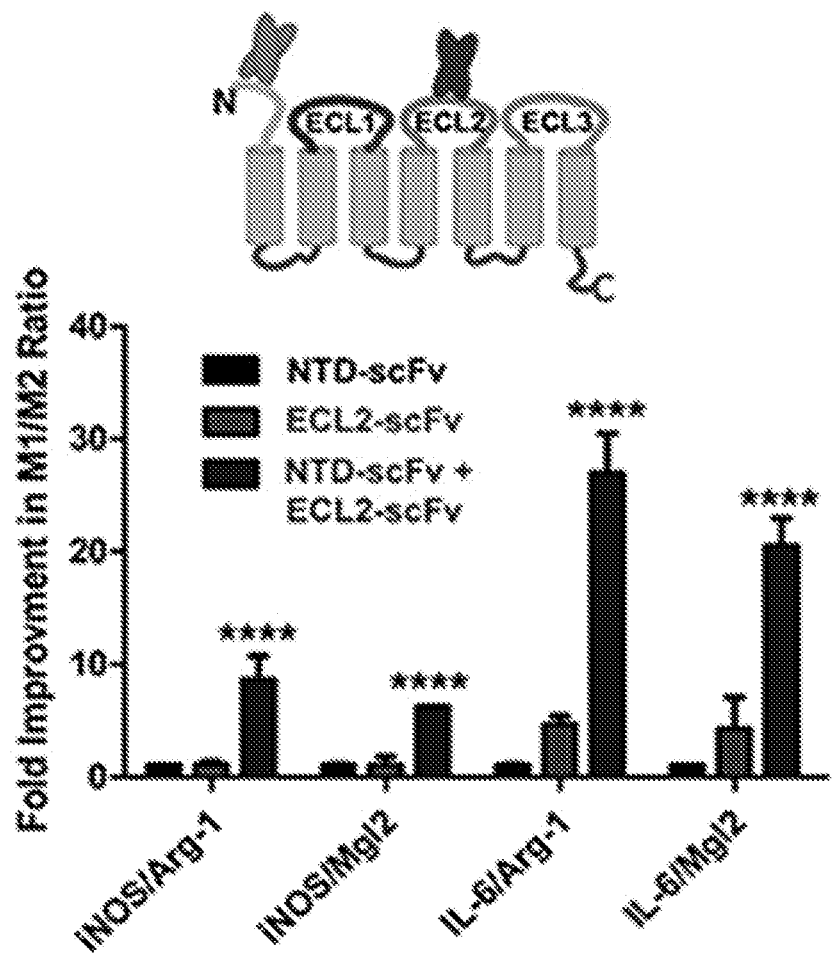
FIG. 17. Simultaneous targeting and blocking of the NTD and ECL2 of the CCR2 chemokine receptor enhances M1 macrophage polarization by up to ~30-fold (A). Data are represented as mean±sd, n=3 with ****$p<0.0001$ by one-way Anova followed by Tukey's post-test. (B) In all M1/M2 ratios tested (iNOS/Arg-1, iNOS/Mgl2, IL-6/Arg-1, IL-6 Mgl2), simultaneous targeting of the NTD and the ECL2 domain led to synergistic enhancement of M1 macrophage polarization as compared to blocking only the NTD or the ECL2 domain in RAW 264.7 macrophages. (C) Combination indices for the combined effects of NTD-scFv and ECL2-scFv in RAW 264.7. (D) Isobolograms indicate synergistic effects of M1 macrophage polarization when bone marrow-derived macrophages (BMDM) were treated with a combination of NTD-scFv and ECL2-scFv (represented as the dots that are all below the isobole). The results in BMDMs showed similar trends to RAW 264.7 cells.
Figure 17:
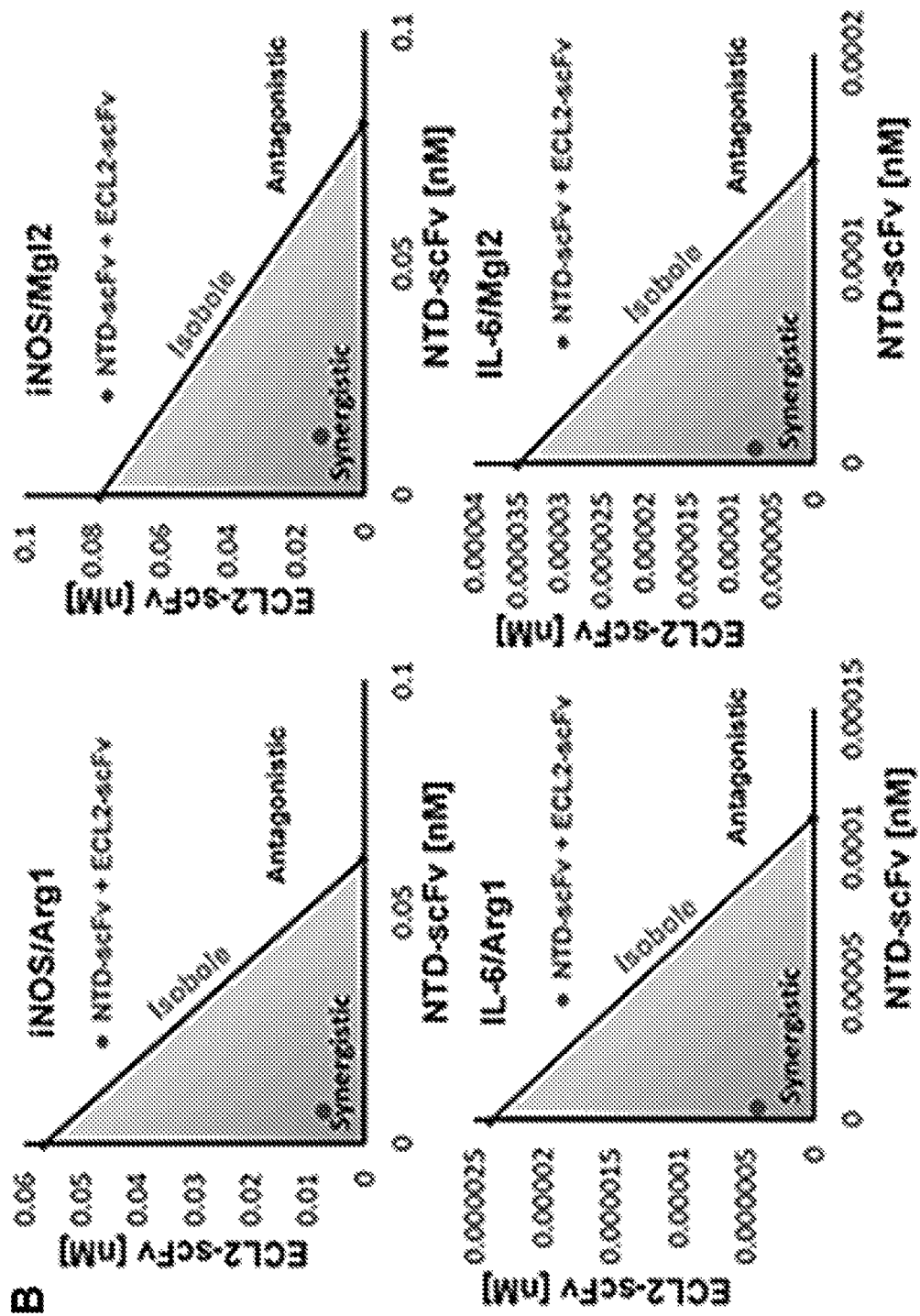
Figure 17:
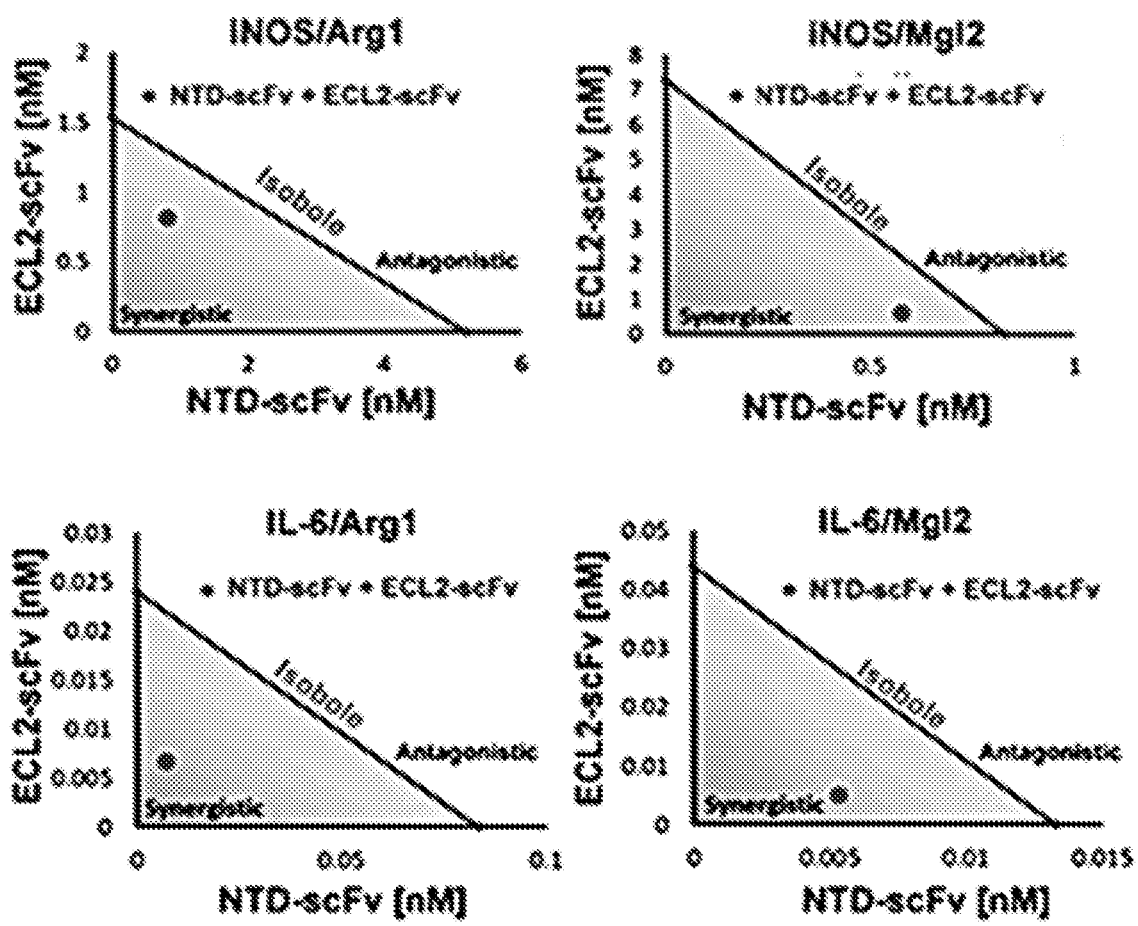

To assess the effects of the anti-CCR2 scFvs on macrophage polarization, RAW 264.7 and bone marrow-derived macrophages (BMDMs) were treated with NTD-scFv and ECL2-scFv. Inducible nitric oxide synthase (iNOS) and interleukin 6 (IL-6) were used as M1 markers. Arginase 1 (Arg1) and macrophage galactose N-acetyl-galactosamine-specific lectin 2 (Mgl2) were used as M2 markers. Preliminary data indicate that simultaneous targeting and blocking of the NTD and ECL2 using the recently developed anti-CCR2 scFvs synergistically increases macrophage polarization to the M1 phenotype by ~6-9-fold (by iNOS/Arg1 and iNOS/Mgl2) and ~20-30-fold as expressed by the M1/M2 marker ratio (IL-6/Arg1 and IL-6/Mgl2) (FIG. 17). To determine whether these changes were additive, synergistic, or antagonistic, the combination indices (CI) were calculated for NTD-scFv and ECL2-scFv by treating cells with a combination of NTD-scFv and ECL2-scFv. CI was calculated by: $CI=(C_{A,X}/IC_{X,A})+(C_{B,X}/IC_{X,B})$, where $C_{A,X}$ and $C_{B,X}$ are the concentration of drug A (in this case NTD-scFv) and B (here, ECL2-scFv) used in combination to achieve x % drug effect. $IC_{X,A}$ and $IC_{X,B}$ are the concentrations for the single scFvs to achieve the same effect. CI<1 indicates synergy, CI=1 indicates additivity, and CI>1 indicates antagonism. As shown in FIG. 17, the computed CI values were all far below 1, indicating that, at the ratios tested, simultaneous NTD and ECL2 blockade led to synergistic M1 macrophage polarization. These studies were performed in RAW 264.7 cells (FIG. 17A, B, C), but similar results were found for bone marrow-derived macrophages isolated from BALB/c mice (FIG. 17D). As shown by the isobolograms, the M1 polarization effects occurred at lower doses when NTD-scFv was used in combination with ECL2-scFv. As displayed in FIGS. 17B and D the dots (that represent NTD-scFv and ECL2-scFv combined) are all below the isobole. This indicates that the combined effects of NTD-scFv and ECL2-scFv were synergistic (FIGS. 17B and D).

NTD-scFv Inhibits Macrophage Migration.

Monocytes, macrophages, and breast cancer cells express CCR2 and migrate along the CCR2/CCL2 chemotaxis gradient. RAW 267.4 cells were incubated with increasing concentrations of NTD-scFv, with CCL2 serving as the chemoattractant in the basolateral chamber of transwells. NTD-scFv (FIG. 3) inhibited ~75% of RAW 264.7 macrophage migration. These data suggest that the NTD-scFv is specific for the CCL2/CCR2 pathway and act as a CCR2 antagonist. NTD-scFv demonstrated ~40-60% higher inhibition of macrophage migration than a commercially available CCR2-targeted antibody.

NTD-scFv Also Inhibits Breast Cancer Cell Migration.

Figure 3:
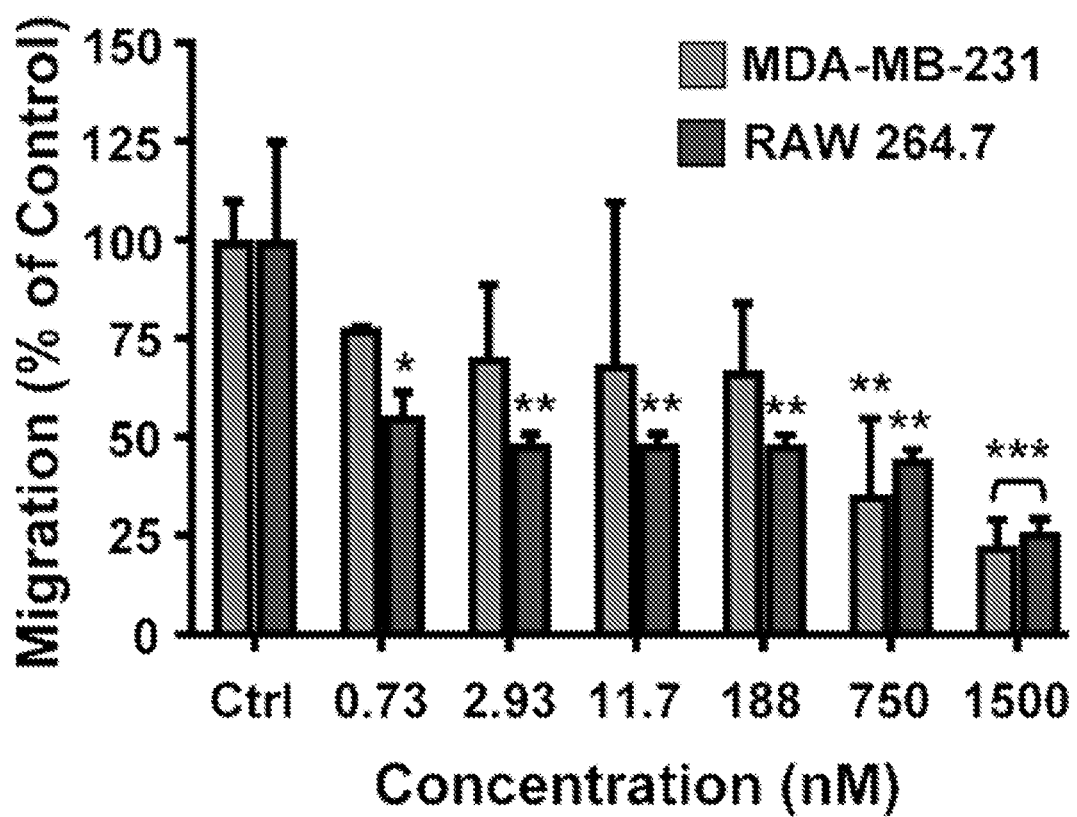
FIG. 3. Effect of free, monomeric 58C-scFv on cellular migration. Transwell migration assay performed with MDA-MB-231 cells and RAW 264.7 cells incubated with increasing concentrations of 58C-scFv. Data are presented as mean±sd (n=3), *p<0.05, p<0.01, *p<0.001 with one-way ANOVA followed by Dunnett's post-test.

CCR2 has also been shown to be expressed on many different types of cancer cells, including breast cancer cells. More importantly, studies have shown that CCR2 mediates breast cancer migration and also contributes to tumor growth and metastatic spread. Thus, inhibiting CCR2/CCL2 mediated breast cancer migration can help to inhibit tumor growth. As shown in FIG. 3, NTD-scFv inhibited migration of MDA-MB-231 breast cancer cells by approximately 75% at the highest concentration tested.

Testing Dual, Triple, and Quadruple Combinations of Anti-CCR2-scFvs.

Figure 18:
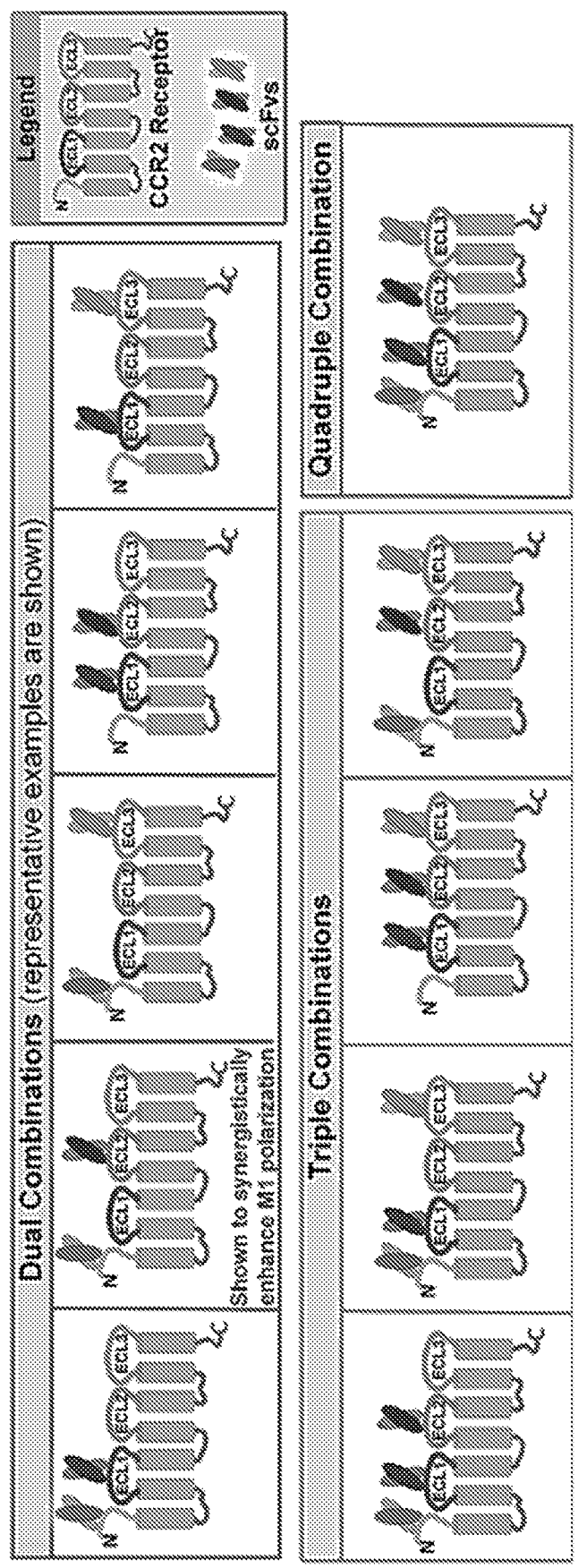
FIG. 18. Proposed scFv combinations to be tested for synergistic, antagonistic, and additive effects on M1 macrophage polarization and cellular migration. Schematics showing dual, triple, and quadruple combinations of scFvs targeting different domains and extracellular loops of CCR2. Proposed combinations for evaluating the effects on inducing M1 macrophage polarization and the effects on inhibiting cellular migration.

After assessing the effects of single scFvs blocking ECL1 and ECL3, we will test how different dual, triple, and quadruple combinations of scFvs affect M1 macrophage polarization and migration. The different scFv combinations are shown in FIG. 18. For the dual combinations, the list is not exhaustive and shows representative examples.

Tumor Treatment with Unmodified NTD-scFv.

Figure 19:
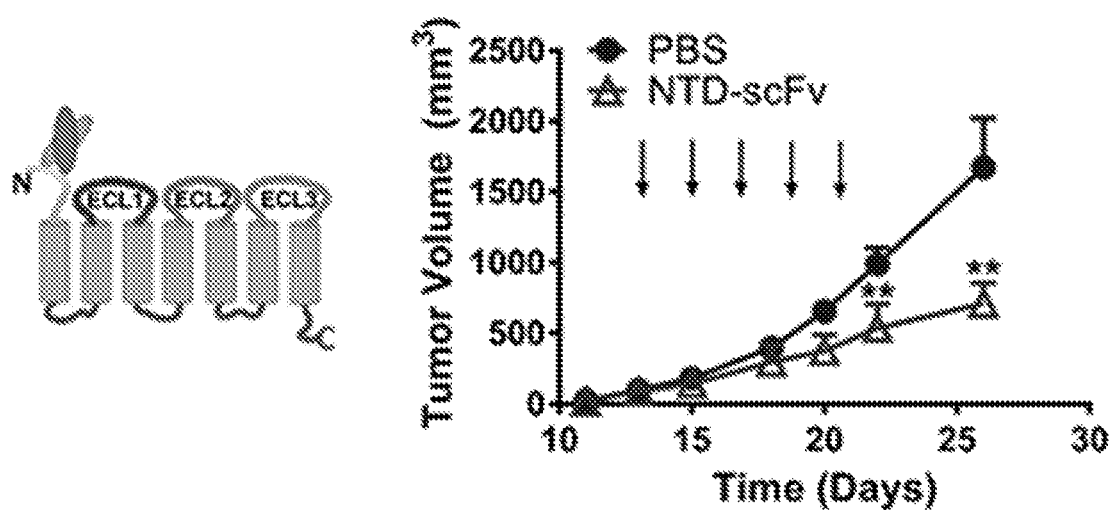
FIG. 19. Tumor size of BALB/C mice treated with unpegylated NTD-scFv (n=5) at a dose of 1.25 mg/kg is significantly smaller than the tumor size of mice treated with PBS (n=4). Arrows indicate time of dosing. Data are represented as mean±sd, **$p<0.01$ by two-tailed Student's t-test.

To assess the therapeutic efficacy of the NTD-scFv, female BALB/c mice harboring 4T1 breast cancer cells in the mammary fat pad were treated with NTD-scFv when the tumor sizes reached 150 mm³. The NTD-scFv was administered via tail vein injection. Mice received five doses of NTD-scFv at two-day intervals at 1.25 mg/kg. PBS-treated mice served as controls. As shown in FIG. 19, tumors in female BALB/c mice treated with NTD-scFv were significantly smaller than mice treated with PBS. These results are highly encouraging because they were performed with the unmodified NTD-scFv, which is eliminated quickly after systemic administration and which shows low tumor deposition (FIG. 20).

Site-Specific PEGylation to Enhance Tumor Deposition of Anti-CCR2 NTD-scFv.

Figure 20:
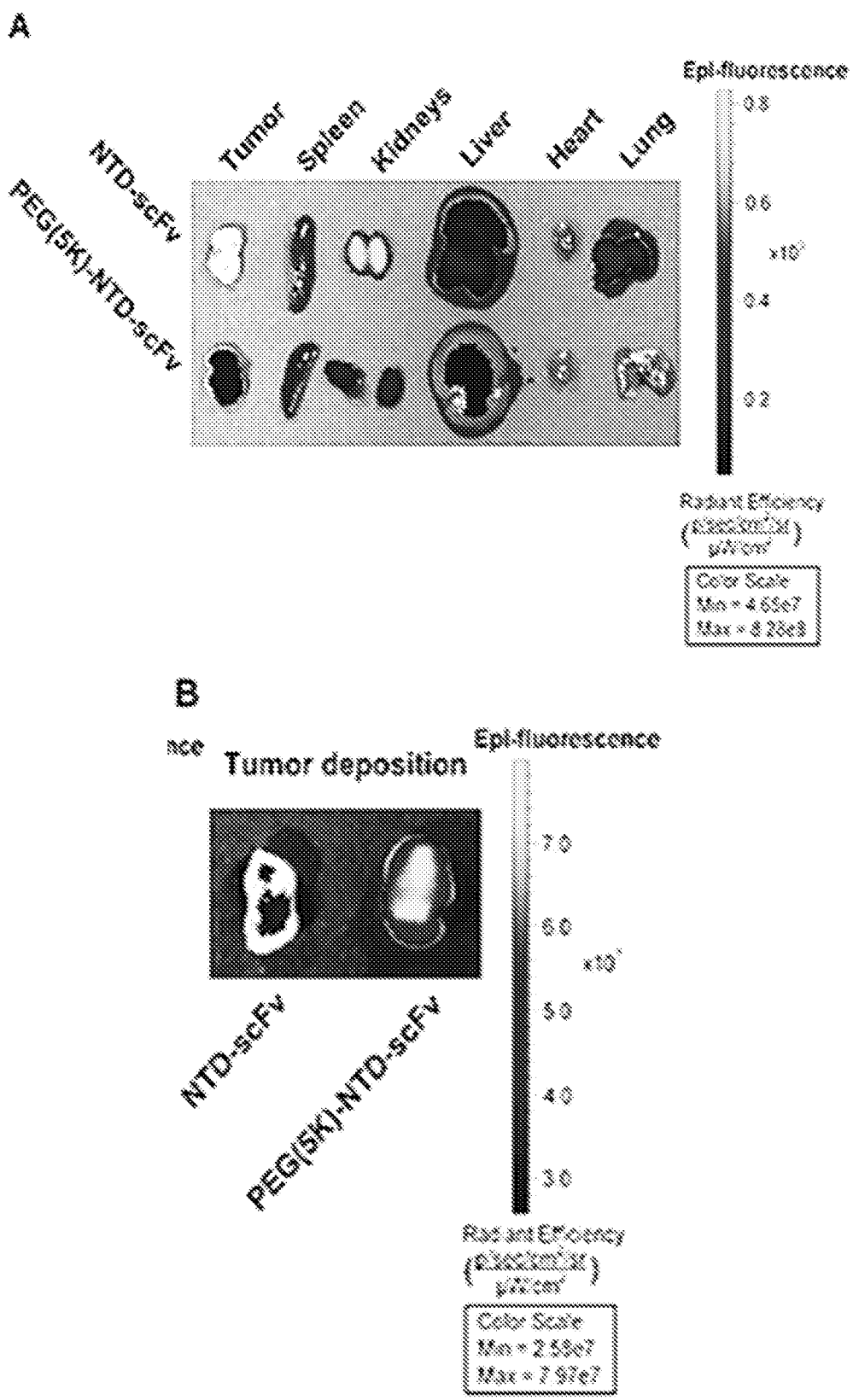
FIG. 20. Biodistribution of PEG(5K)-NTD-scFv and NTD-scFv (labeled with DyLight 650) in tumored BALB/C mice. (A,B) PEGylation enhances deposition of fluorescently labeled PEG(5K)-NTD-scFv compared to unmodified fluorescently labeled NTD-scFv. (C) In vivo biodistribution of NTD-scFv and PEG(5K)-NTD-scFv expressed as % injected dose (ID). Data are presented as mean±sd (n=3). N.D.=not detectable.
Figure 20:
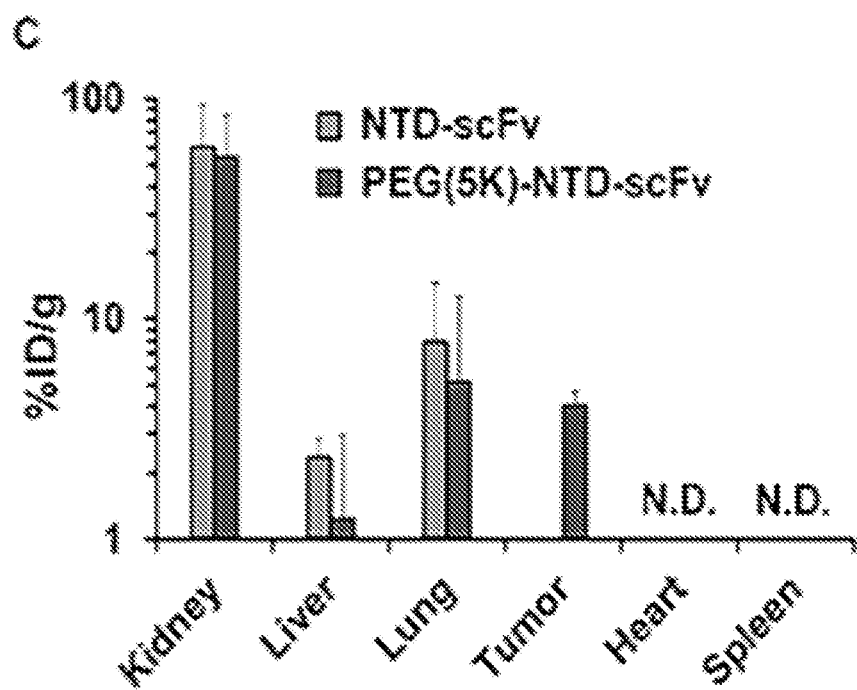

Non-pegylated NTD-scFv shows low deposition in the tumor (FIG. 20). PEGylation of proteins have been shown to enhance the circulatory half-life and tumor deposition. Further, PEGylating of proteins can be carried out to enhance their circulatory half-life and improve bioavailability. To enhance the tumor deposition of the NTD-scFv without masking its binding site to CCR2, the NTD-scFv was modified to contain a cysteine at the C-terminus for attachment to PEG(5K)-maleimide (Sigma Aldrich). The cysteine was introduced into the NTD-scFv via site-directed mutagenesis at the C-terminus, and the correct sequence confirmed through Sanger sequencing. The cysteine-modified NTD-scFv was added to a PEG(5K)-maleimide solution at a 1:5 molar ratio of NTD-scFv to PEG(5K)-maleimide to ensure complete PEGylation. Excess PEG was removed using a 10 kDa molecular weight cut-off column. When administered into BALB/c mice via tail vein injection, PEG(5K)-NTD-scFv showed significantly higher tumor deposition (4.0±0.2% of injected dose) compared to unPEGylated NTD-scFv (FIG. 20A, C). While NTD-scFv does accumulate in the tumor as displayed in FIG. 20B, the deposition is so minimal that it cannot be detected relative to the high signals found in the kidneys (FIG. 20A, B). Both PEG(5K)-NTD-scFv and the unpegylated NTD-scFv showed high deposition in the kidneys which is indicative of fast renal clearance (FIG. 20A, B).

PEG(40K) Significantly Enhances Circulatory Half-Life of the Anti-CCR2 NTD-scFv.

Figure 21:
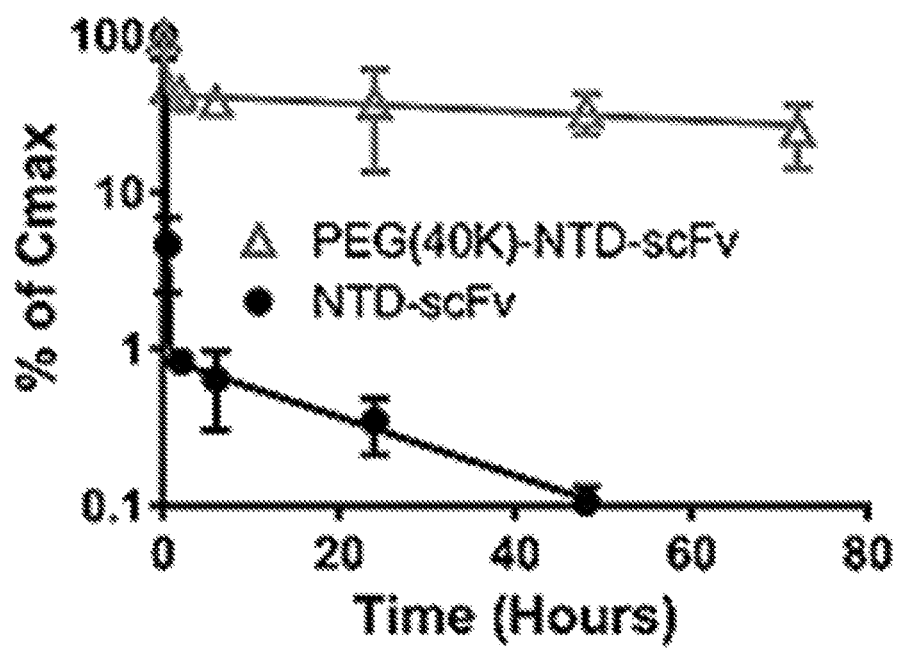

When attaching PEG(40K)-maleimide to the NTD-scFv a 7-fold greater elimination half-life was obtained ($t_{1/2}$ ($\beta$)=111h) compared to unmodified NTD-scFv, which has an elimination half-life of $t_{1/2}$ ($\beta$)=16h (FIG. 21). The distribution half-life of PEG(40K)-NTD-scFv ($t_{1/2}$ ($\alpha$)=0.12h) was 11-fold greater than that of NTD-scFv ($t_{1/2}$ ($\alpha$)=0.01h). Since the PEG(40K) shows longer circulation compared to a PEG(5K), we expect that the PEG(40K)-NTD-scFv will result in enhanced tumor deposition compared to the PEG (5K)-NTD-scFv and unmodified NTD-scFv.

Figure 22:
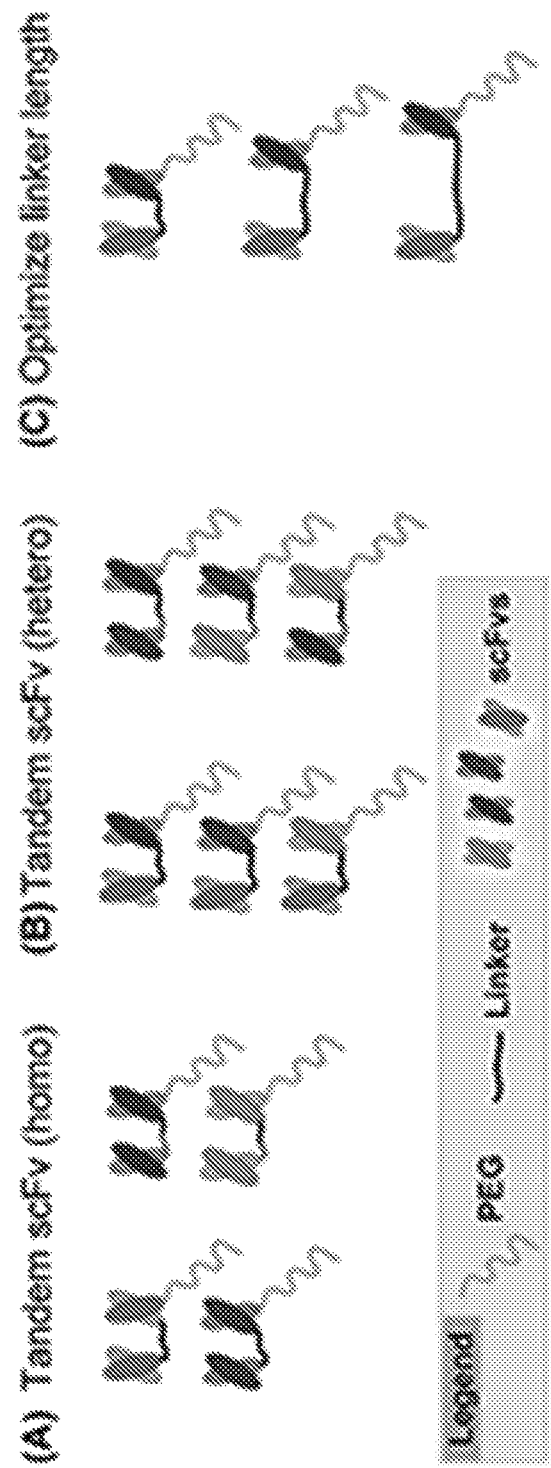
FIG. 22. Homo and hetero tandem scFvs obtain bivalent targeting ligands (A,B). To optimize binding affinity linker length will vary (C). Pegylation will be used to enhance circulatory half-life and tumor deposition.

Tandem scFvs are created by linking two scFvs into a single polypeptide that is separated by a (GSGSGS)n (SEQ ID NO:59) linker (FIG. 22A, B). Tandem scFvs are PEGylated using the procedure described above to enhance circulatory half-life and tumor deposition (FIG. 20). Further, the linker length can be varied to optimize binding affinity to CCR2 (FIG. 22C).

Figure 23:
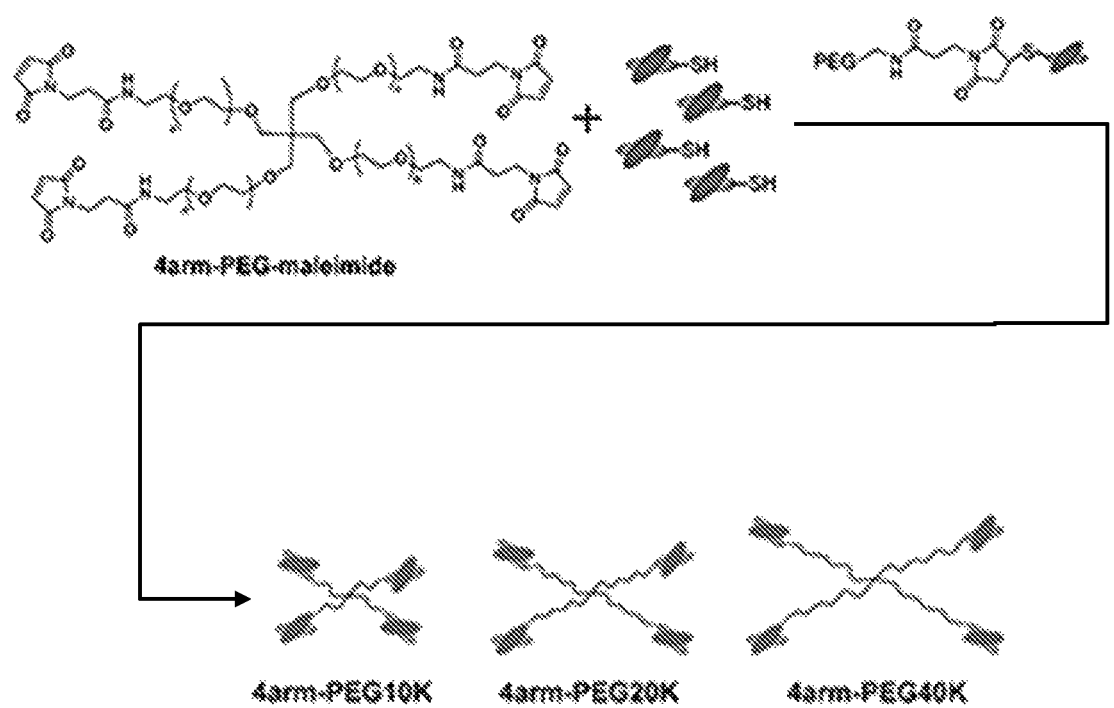
FIG. 23. Synthesis of 4arm-PEG10K-scFvs, 4arm-PEG20K-scFvs, and 4arm-PEG40K-scFvs.
Figure 24:
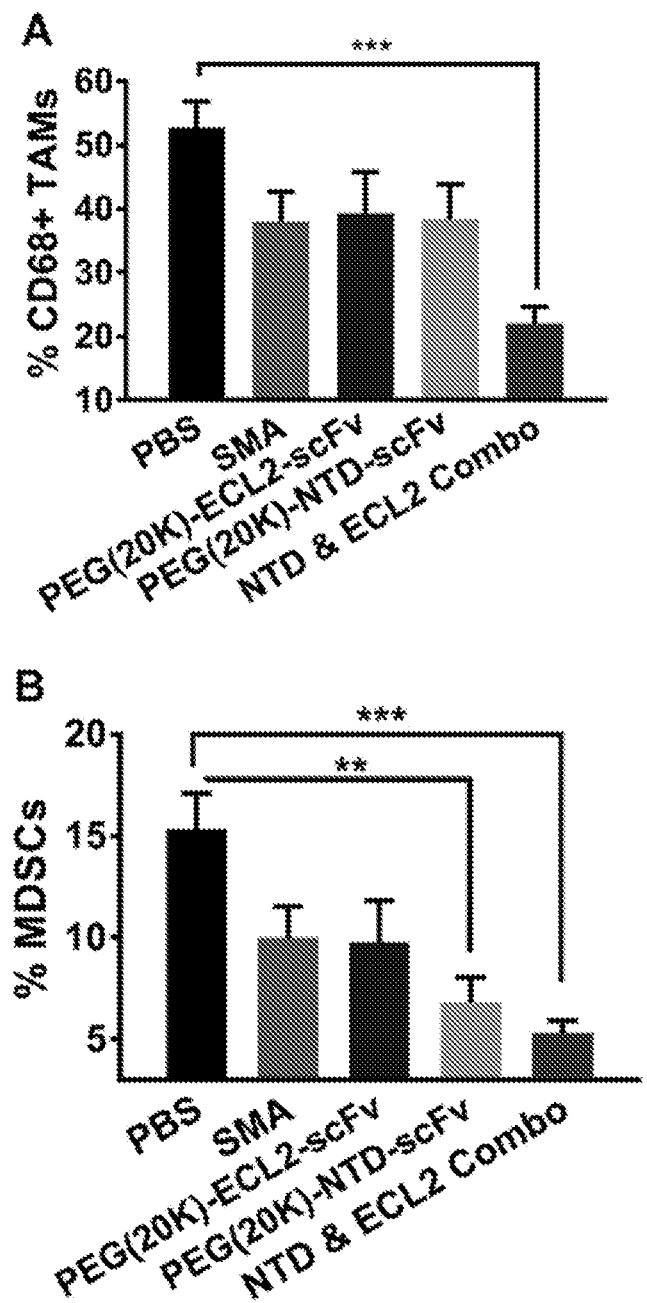
FIG. 24. Single cell suspension from the harvested tumors following dual epitope blocking were analyzed by flow cytometry. The cells were stained for (A) CD68+ TAMs, (B) MDSCs, (C) MHC class II macrophages (M1), and (D) CD206+ macrophages (M2). Data is shown for TAMs, MDSCs, and M2-Macrophages and increased M1-Macrophages in triple-negative breast cancer (TNBCs).
Figure 24:
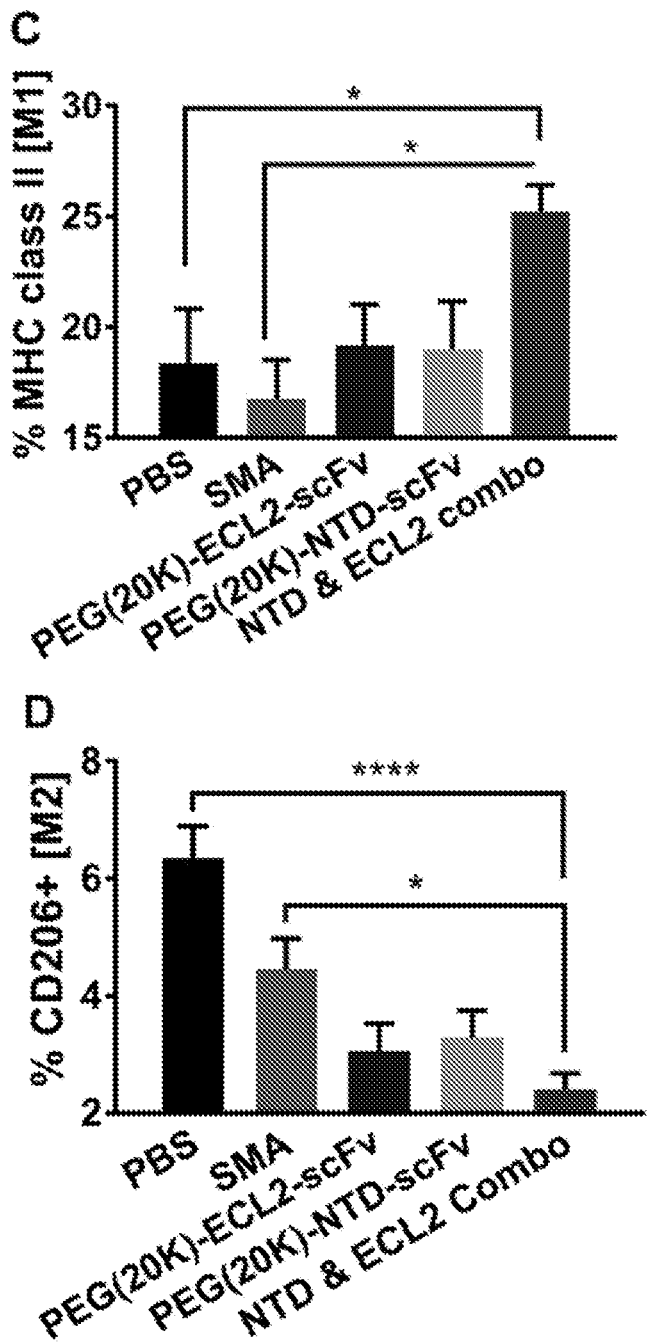

Additionally, the scFvs can be conjugated to 4arm-PEG10K, 4arm-PEG20K, and 4-arm-PEG40K (FIG. 23). The 4arm-PEG40K allows the synthesis of multivalent anti-CCR2 scFvs which can further lead to an increase in binding affinity and efficacy.

Example 3

This example demonstrates synergistic action of antibodies directed to N-terminal domain and ECL2 domain of CCR2. scFv 58C directed to the N-terminal domain and scFv 4h directed to the ECL2 of CCR2 were used.

At study completion, the tumors were harvested, digested, and single cell suspensions stained for immune cells. Dual-epitope blocking of CCR2 reduced TAMs, MDSCs, and M2-Macrophages and increased M1-Macrophages in triple-negative breast cancer (TNBCs). Co-dosing of the pegylated NTD- and ECL2-scFv (NTD & ECL2 Combo) resulted in significant decreases in myeloid-derived suppressor cells (MDSCs) by ~3-fold, CD68+ TAMs by ~2.5-fold, M2-like macrophages by ~2.6-fold, and an increase in MHC class II$^{hi}$ M1-like macrophages by ~1.4-fold compared to PBS-treated animals (FIG. 24A-D). The effects of the small molecule CCR2 antagonist (SMA, RS 504393) were not significant compared to control mice treated with PBS (FIG. 24A-D).

We observed that dual-epitope scFv combination treatment outperforms small molecule CCR2 antagonist (SMA) and decreased tumor-associated macrophages (TAMs), myeloid-derived suppressor cells (MDSCs), and M2-macrophages and increased M1-macrophages. Single cell suspension from the harvested tumors were analyzed by flow cytometry. The cells were stained for (A) CD68+ TAMs, (B) MDSCs, (C) MHC class II macrophages (M1), and (D) CD206+ macrophages (M2).

Treatment groups included: PBS, CCR2 small molecule antagonist (SMA), PEG(20K)-ECL2-scFv, PEG(20K)-NTD-scFv, and NTD & ECL2 combination (co-dosing of PEG(20K)-ECL2-scFv and PEG(20K)-NTD-scFv), with *$p<0.05$, $p<0.01$, and *$p<0.001$ by one-way ANOVA followed by Tukey's post-test.

Figure 25:
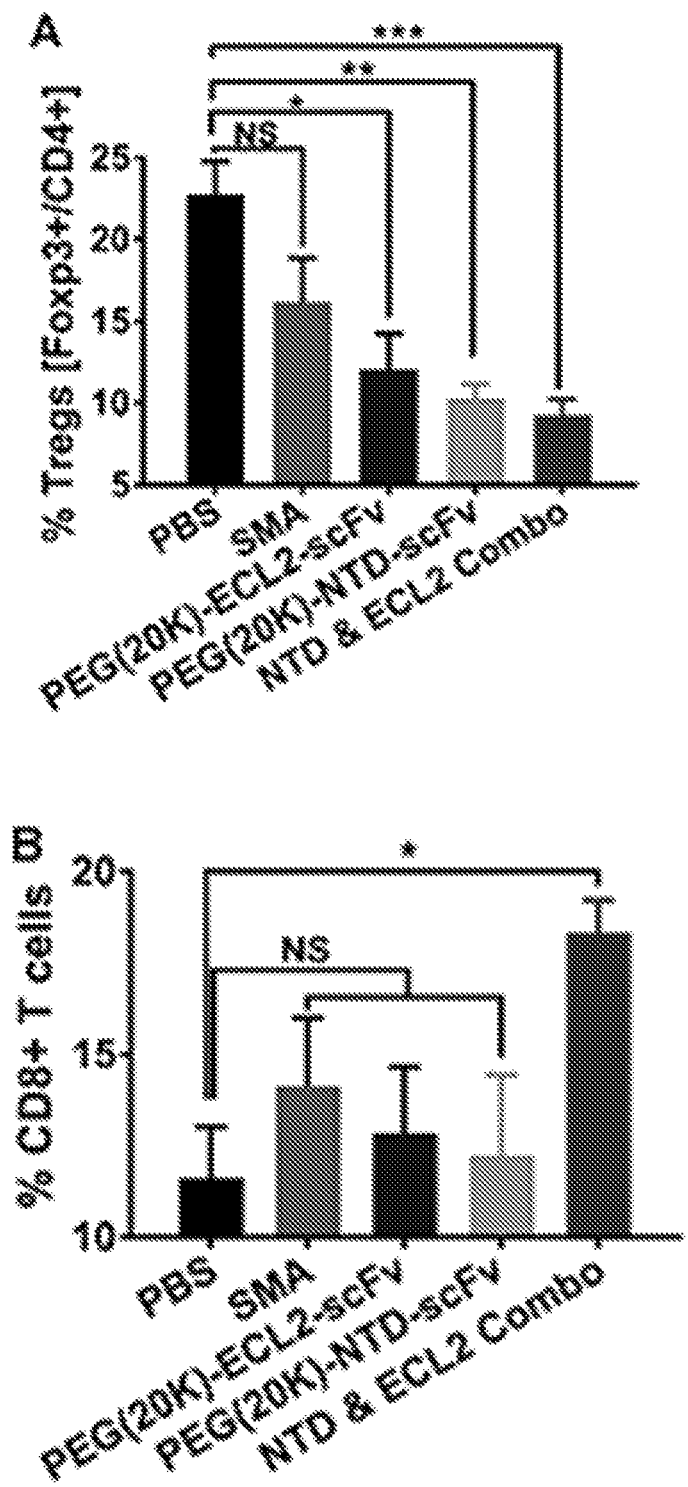
FIG. 25. Dual-epitope scFv combo treatment outperforms small molecule CCR2 antagonist (SMA) and decreases immunosuppressive $CD4^+FoxP3^+$ Tregs, and increases cytotoxic CD8+ and CD4+ T cells. Single cell suspension from the harvested tumors were analyzed by flow cytometry. The cells were stained for (A) Foxp3+/CD4+ Tregs, (B) CD4+ T cells, and (C) CD8+ T cells. Treatment groups included: PBS, CCR2-small molecule antagonist (SMA), PEG(20K)-ECL2-scFv, PEG(20K)-NTD-scFv, and NTD & ECL2 combo, *$p<0.05$, $p<0.01$, and *$p<0.001$ by one-way ANOVA followed by Tukey's post-test, NS=not significant.
Figure 25:
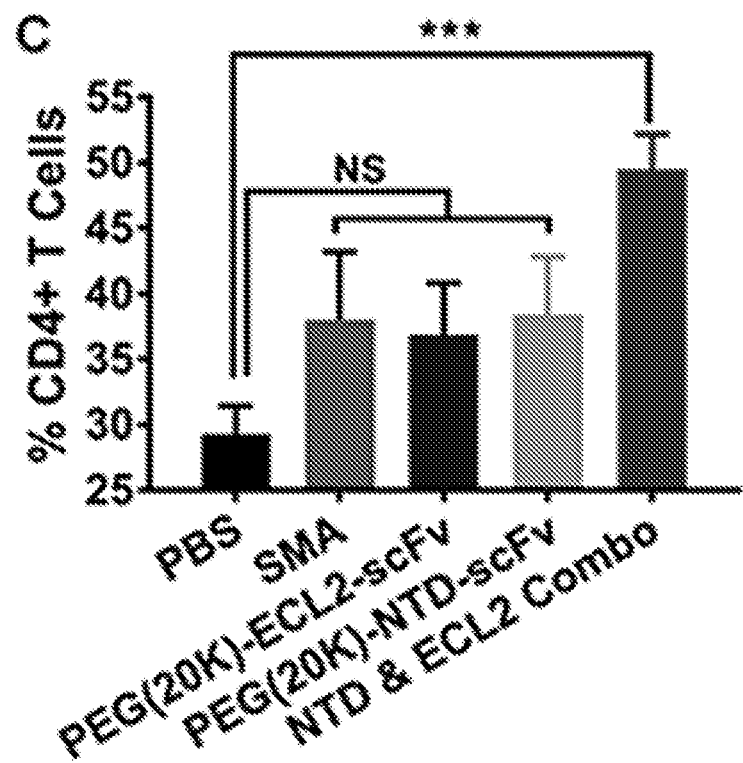

Further, we observed that dual-epitope targeting strategy restores anti-tumor immunity. Compared to the small molecule CCR2 antagonist and the other formulations tested, dual-epitope therapy showed the strongest reduction in immunosuppressive CD4$^+$FoxP3$^{+-}$Tregs (~2.5-fold decrease, FIG. 25A)). The dual-epitope combination therapy also significantly increased cytotoxic CD8+ T cells and CD4+ T cells in the tumor tissue (FIG. 25B, C). While mice treated with the small molecule antagonist (SMA) and the individual scFvs against ECL2 and against NTD slightly decreased immunosuppressive Tregs and increasing cytotoxic CD8+ T cells and CD4+ T cells, no statistically significant reduction compared to PBS treated mice were found. This indicates that dual-epitope combination therapy is superior to conventional targeting approaches and can favorably restore anti-tumor immunity.

Figure 26:
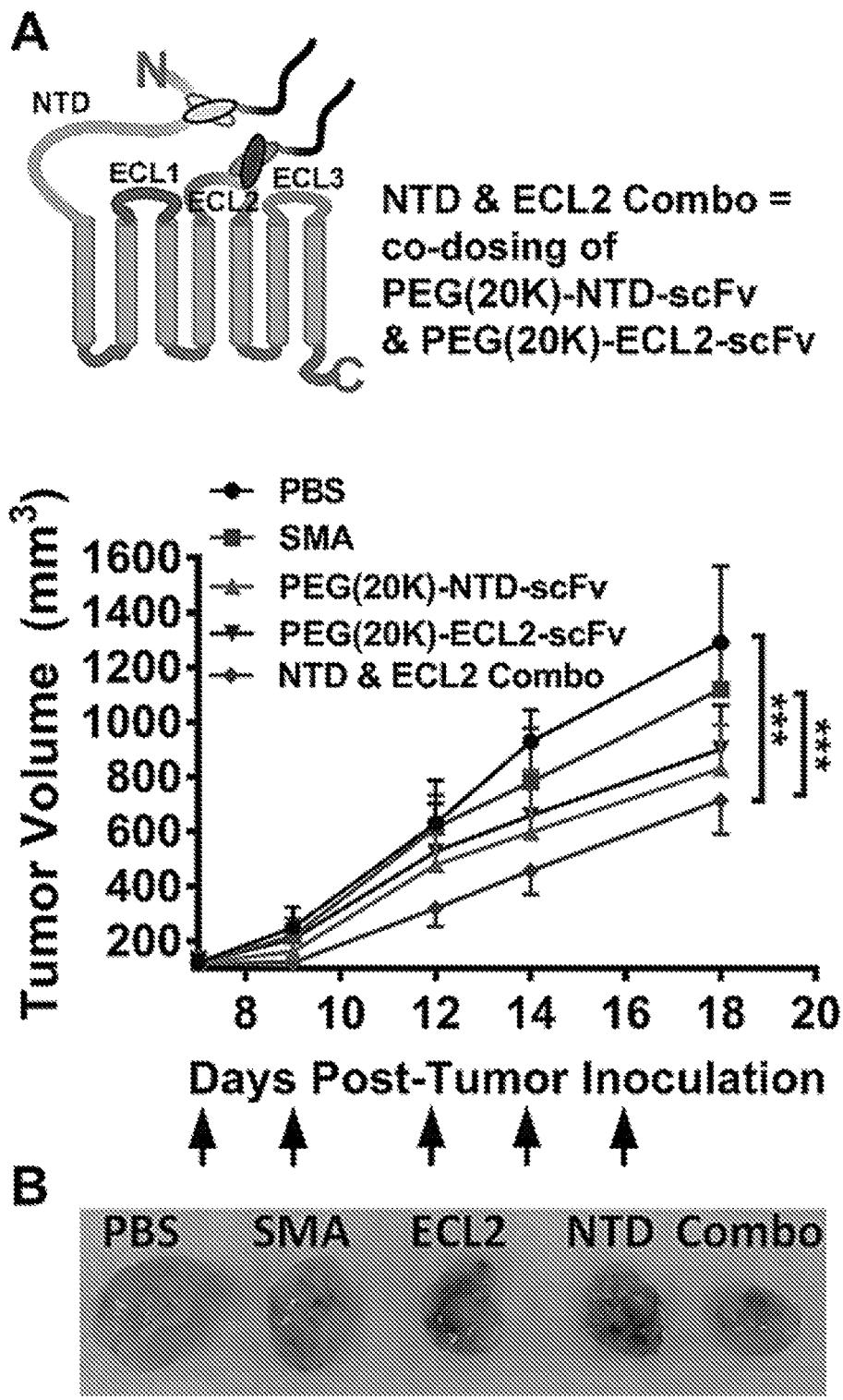
FIG. 26. Tumor sizes in BALB/C mice treated with PBS, CCR2-small molecule antagonist (SMA) at 2 mg/kg, PEG (20K)-NTD-scFv, PEG(20K)-ECL2-scFv, and PEG(20K)-NTD-scFv & PEG(20K)-ECL2-svFv combo at 1 mg/kg; (n=10) (A, B). Black arrows indicate time of dosing. Data are represented as mean±sd, *$p<0.05$ and ***$p<0.001$ by one-way ANOVA followed by Tukey's post-test.

Further, we evaluated the effect of dual epitope blocking of CCCR2 on tumor growth. TNBCs were injected into the mammary fat pads of female BALB/c mice. Treatment of tumored mice started on days 7, 9, 12, 14, 16, and 18. To enhance the circulation half-life of the NTD-scFv and ECL2-scFv, we used site-directed mutagenesis to introduce a cysteine at the C-terminus of the scFvs for covalent attachment of a PEG-maleimide with molecular weight of 20 kDa. Animals (n=10 per group) were systemically (via tail vein injection) treated with (1) PBS, (2) CCR2-small molecule antagonist (SMA), (3) PEG(20K)-NTD-scFv, (4) PEG(20K)-ECL2-scFv, and (5) a NTD and ECL2 combo (co-dosing of PEG(20K)-NTD-scFv and PEG(20K)-ECL2-scFv). The NTD and ECL2 combination demonstrated highest reduction in tumor volume, followed by single PEG (20K)-NTD-scFv or PEG(20K)-ECL2-scFv treatment (FIG. 26A, B). The small molecule CCR2 antagonist (SMA), RS 504393, had the weakest effect on tumor growth.

Although the present disclosure has been described using specific embodiments and examples, routine modifications will be apparent to those skilled in the art and such modifications are intended to be within the scope of the disclosure and the claims.

REFERENCES

1. Pittet, M. J.; *Eur J Immunol* 2011, 41, (9), 2519-22.
2. Talbot, J.; *Arthritis Rheumatol* 2015, 67, (7), 1751-9.
3. Heck, S.; *Int Arch Allergy Immunol* 2015, 168, (4), 241-52.
4. Italiani, P.; *Front Immunol* 2014, 5, (1), 514.
5. Classen, A.; *Macrophage activation: classical versus alternative.* 2009; Vol. 531, p 29-43.
6. Lyamina, S. V.; *Bulletin of Experimental Biology and Medicine* 2012, 152, (4), 548-551.
7. Yamane, K.; *Febs Open Bio* 2016, 6, (9), 945-953.
8. Egawa, M.; *Immunity* 2013, 38, (3), 570-80.
9. Martinez, F. O.; *F1000Prime Rep* 2014, 6, (13), 13.
10. Mantovani, A.; *Trends in Immunology* 2002, 23, (11), 549-555.
11. Messmer, M. N.; *Cancer Immunol Immunother* 2015, 64, (1), 1-13.
12. Yoshikawa, K.; *Cancer Sci* 2012, 103, (11), 2012-20.
13. Condeelis, J.; *Cell* 2006, 124, (2), 263-6.
14. Li, N.; *Cancer Biol Ther* 2015, 16, (2), 297-306.
15. Roca, H.; *J. Biol. Chem.* 2009, 284, (49), 34342-54.
16. Monteclaro, F. S.; *J. Biol. Chem.* 1997, 272, (37), 23186-23190.
17. Prossnitz, E. R.; *Biochemistry* 1999, 38, (8), 2240-7.
18. Han, K. H.; *J. Biol. Chem.* 1999, 274, (45), 32055-62.
19. Nywening, T. M.; *Lancet Oncol* 2016, 17, (5), 651-62.
20. Sanford, D. E.; *Clin Cancer Res* 2013, 19, (13), 3404-15.
21. Gilbert, J.; *Am J Cardiol* 2011, 107, (6), 906-11.
22. Lim, S. Y.; *Oncotarget* 2016, 7, (19), 28697-710.
23. Wang-Gillam, A.; *Journal of Clinical Oncology* 2015, 33, (3).
24. Huang, R.; *Int J Mol Sci* 2015, 16, (10), 23587-603.

What is claimed is:

1. An antibody that is specific for the extracellular loop 2 domain of CCR2 comprising a variable light chain (VL) and a variable heavy chain (VH) wherein:
   a) the VL comprises CDRL1 denoted by the sequence SGSSSNIGSHTVN (SEQ ID NO: 47), CDRL2 denoted by the sequence RNNQRPS (SEQ ID NO:34), and CDRL3 denoted by the sequence AAWDDSLSGVV (SEQ ID NO:48), and the VH comprises CDRH1 denoted by the sequence NFYIH (SEQ ID NO:30), CDRH2 denoted by the sequence IINPSDGRTTYAQKFQG (SEQ ID NO:31), and CDRH3 denoted by the sequence GGHYSNYFGQPST (SEQ ID NO:49); or
   b) the VL comprises CDRL1 denoted by the sequence SGSSSNIGSNYVY (SEQ ID NO: 33), CDRL2 denoted by the sequence RNNQRPS (SEQ ID NO:34), and CDRL3 denoted by the sequence AAWDDTLIGPV (SEQ ID NO:50), and the VH comprises CDRH1 denoted by the sequence DAWMN (SEQ ID NO:51), CDRH2 denoted by the sequence RIRSKAGGGTTDSAAPVKD (SEQ ID NO:52), and CDRH3 denoted by the sequence EGY.

2. A pharmaceutical composition comprising an antibody that is specific for the N-terminal domain of CCR2 comprising a variable light chain (VL) and a variable heavy chain (VH) wherein:
   a) the VL comprises CDRL1 denoted by the sequence ILRSDFSVVTQRVY (SEQ ID NO:8), CDRL2 denoted by the sequence NSDSDKRLGS (SEQ ID NO:22), and CDRL3 denoted by the sequence VIWHNSAVV (SEQ ID NO:23), and the VH comprises CDRH1 denoted by the sequence SYWIG (SEQ ID NO:24), CDRH2, denoted by the sequence IIYPGDSDTRYSPSFOG (SEQ ID NO:25), and CDRH3, denoted by the sequence RPQYYDILTGWHAG (SEQ ID NO:26);
   b) the VL comprises CDRL1 denoted by the sequence SGSSSNIGNNYVS (SEQ ID NO: 27), CDRL2 denoted by the sequence GNNKRPS (SEQ ID NO:28), and CDRL3 denoted by the sequence ATWDDSLSAVV (SEQ ID NO:29), and the VH comprises CDRH1 denoted by the sequence NFYIH (SEQ ID NO:30), CDRH2 denoted by the sequence IINPSDGRTTYAQKFOG (SEQ ID NO:31), and CDRH3, denoted by the sequence GGHYSNYFGQ (SEQ ID NO:32);
   c) the VL comprises CDRL1 denoted by the sequence SGSSSNIGSNYVY (SEQ ID NO: 33), CDRL2, denoted by the sequence RNNQRPS (SEQ ID NO:34), and CDRL3, denoted by the sequence AAWDDSLNGVV (SEQ ID NO:35), and the VH comprises CDRH1 denoted by the sequence NFYIH (SEQ ID NO:30), CDRH2 denoted by the sequence IINPSDGRTTYAQKFQG (SEQ ID NO:31), and CDRH3 denoted by the sequence GGHYSNYFGQ (SEQ ID NO:32);
   d) the VL comprises CDRL1 denoted by the sequence KASGYTFTSYYMH (SEQ ID NO:36), CDRL2 denoted by the sequence NPSGGST (SEQ ID NO:37), and CDRL3 denoted by the sequence ARDGNWFDP (SEQ ID NO:38), and the VH comprises CDRH1 denoted by the sequence SSYLA (SEQ ID NO:39), CDRH2 denoted by the sequence IYGASSRATGIPDRESG (SEQ ID NO:40), and CDRH3 denoted by the sequence QYGSS (SEQ ID NO:41); or
   e) the VL comprises CDRL1 denoted by the sequence RASQSVSSSYLA (SEQ ID NO: 42), CDRL2 denoted by the sequence GASSRAT (SEQ ID NO:43), and CDRL3 denoted by the sequence QQYGSSLT (SEQ ID NO:44), and the VH comprises CDRH1 denoted by the sequence TYDIY (SEQ ID NO:9), CDRH2 denoted by the sequence WVNPDNGKTDYAQKFOG (SEQ ID NO:45), and CDRH3, denoted by the sequence ALTRWQQS (SEQ ID NO:46);
   and further comprising an antibody that is specific for the extracellular loop 2 domain of CCR2 comprising a variable light chain (VL) and a variable heavy chain (VH) wherein:
   f) the VL comprises CDRL1 denoted by the sequence SGSSSNIGSHTVN (SEQ ID NO: 47), CDRL2 denoted by the sequence RNNQRPS (SEQ ID NO:34), and CDRL3 denoted by the sequence AAWDD-SLSGVV (SEQ ID NO:48), and the VH comprises CDRH1 denoted by the sequence NFYIH (SEQ ID NO:30), CDRH2 denoted by the sequence IINPSDGRTTYAQKFQG (SEQ ID NO:31), and CDRH3 denoted by the sequence GGHYSNYFGQPST (SEQ ID NO:49); or g) the VL comprises CDRL1 denoted by the sequence SGSSSNIGSNYVY (SEQ ID NO: 33), CDRL2 denoted by the sequence RNNQRPS (SEQ ID NO:34), and CDRL3 denoted by the sequence AAWDDT-LIGPV (SEQ ID NO:50), and the VH comprises CDRH1 denoted by the sequence DAWMN (SEQ ID NO:51), CDRH2 denoted by the sequence RIRSK-AGGGTTDSAAPVKD (SEQ ID NO:52), and CDRH3 denoted by the sequence EGY.

3. A method for inhibiting growth of a tumor in an individual comprising administering to the individual a composition comprising an scFv that is specific for the N-terminal domain of CCR2 and an scFv that is specific for the extracellular loop 2 domain of CCR2, wherein the scFv that is specific for the N-terminal domain of CCR2 comprises a variable light chain (VL) and a variable heavy chain (VH) wherein:

a) the VL comprises CDRL1 denoted by the sequence ILRSDFSVVTQRVY (SEQ ID NO:8), CDRL2 denoted by the sequence NSDSDKRLGS (SEQ ID NO:22), and CDRL3 denoted by the sequence VIWHNSAVV (SEQ ID NO:23), and the VH comprises CDRH1 denoted by the sequence SYWIG (SEQ ID NO:24), CDRH2, denoted by the sequence IIYPGDSDTRYSPSFQG (SEQ ID NO:25), and CDRH3, denoted by the sequence RPQYYDILTGWHAG (SEQ ID NO:26);

b) the VL comprises CDRL1 denoted by the sequence SGSSSNIGNNYVS (SEQ ID NO: 27), CDRL2 denoted by the sequence GNNKRPS (SEQ ID NO:28), and CDRL3 denoted by the sequence ATWDDSLSAVV (SEQ ID NO:29), and the VH comprises CDRH1 denoted by the sequence NFYIH (SEQ ID NO:30), CDRH2 denoted by the sequence IINPSDGRTTYAQKFQG (SEQ ID NO:31), and CDRH3, denoted by the sequence GGHYSNYFGQ (SEQ ID NO:32);

c) the VL comprises CDRL1 denoted by the sequence SGSSSNIGSNYVY (SEQ ID NO: 33), CDRL2, denoted by the sequence RNNQRPS (SEQ ID NO:34), and CDRL3, denoted by the sequence AAWDDSLNGVV (SEQ ID NO:35), and the VH comprises CDRH1 denoted by the sequence NFYIH (SEQ ID NO:30), CDRH2 denoted by the sequence IINPSDGRTTYAQKFQG (SEQ ID NO:31), and CDRH3 denoted by the sequence GGHYSNYFGQ (SEQ ID NO:32);

d) the VL comprises CDRL1 denoted by the sequence KASGYTFTSYYMH (SEQ ID NO:36), CDRL2 denoted by the sequence NPSGGST (SEQ ID NO:37), and CDRL3 denoted by the sequence ARDGNWFDP (SEQ ID NO:38), and the VH comprises CDRH1 denoted by the sequence SSYLA (SEQ ID NO:39), CDRH2 denoted by the sequence IYGASSRATGIPDRFSG (SEQ ID NO:40), and CDRH3 denoted by the sequence QYGSS (SEQ ID NO:41); or e) the VL comprises CDRL1 denoted by the sequence RASQSVSSSYLA (SEQ ID NO: 42), CDRL2 denoted by the sequence GASSRAT (SEQ ID NO:43), and CDRL3 denoted by the sequence QQYGSSLT (SEQ ID NO:44), and the VH comprises CDRH1 denoted by the sequence TYDIY (SEQ ID NO:9), CDRH2 denoted by the sequence WVNPDNGKTDYAQKFQG (SEQ ID NO:45), and CDRH3, denoted by the sequence ALTRWQQS (SEQ ID NO:46), and wherein the scFv that is specific for the extracellular loop 2 domain of CCR2 comprises a variable light chain (VL) and a variable heavy chain (VH) wherein:

a) the VL comprises CDRL1 denoted by the sequence SGSSSNIGSHTVN (SEQ ID NO: 47), CDRL2 denoted by the sequence RNNQRPS (SEQ ID NO:34), and CDRL3 denoted by the sequence AAWDDSLSGVV (SEQ ID NO:48), and the VH comprises CDRH1 denoted by the sequence NFYIH (SEQ ID NO:30), CDRH2 denoted by the sequence IINPSDGRTTYAQKFQG (SEQ ID NO:31), and CDRH3 denoted by the sequence GGHYSNYFGQPST (SEQ ID NO:49); or b) the VL comprises CDRL1 denoted by the sequence SGSSSNIGSNYVY (SEQ ID NO: 33), CDRL2 denoted by the sequence RNNQRPS (SEQ ID NO:34), and CDRL3 denoted by the sequence AAWDDTLIGPV (SEQ ID NO:50), and the VH comprises CDRH1 denoted by the sequence DAWMN (SEQ ID NO:51), CDRH2 denoted by the sequence RIRSKAGGGTTDSAAPVKD (SEQ ID NO:52), and CDRH3 denoted by the sequence EGY.

4. The method of claim 3, wherein the scFv that is specific for the N-terminal domain of CCR2 and the scFv that is specific for the extracellular loop 2 domain of CCR2 have a synergistic action with respect to one or more of the following: inhibition of tumor growth, reduction of TAMs, reduction of MDSCs, reduction of M2-macrophages, reduction of Foxp3+/CD4+ Tregs, increase in M1-macrophages, increase in CD8+ T cells, and increase in CD4+ T cells.

5. The antibody of claim 1, wherein the antibody is a scFv.

6. The antibody of claim 1, wherein the antibody attenuates the migratory properties of CCR2 expressing cells.

7. The antibody of claim 6, wherein the antibody is PEGylated.

8. A pharmaceutical composition comprising an antibody of claim 1.

* * * * *